US012780880B2

(12) United States Patent
Hikichi et al.

(10) Patent No.: US 12,780,880 B2
(45) Date of Patent: Nov. 3, 2026

(54) SARS-COV-2 PROTEIN-DERIVED PEPTIDE AND VACCINE CONTAINING SAME

(71) Applicants: ONCOTHERAPY SCIENCE, INC., Kawasaki (JP); CANCER PRECISION MEDICINE, INC., Kawasaki (JP)

(72) Inventors: Tetsuro Hikichi, Kawasaki (JP); Kazuma Kiyotani, Kawasaki (JP); Yusuke Nakamura, Kawasaki (JP)

(73) Assignees: ONCOTHERAPY SCIENCE, INC., Kawasaki (JP); CANCER PRECISION MEDICINE, INC., Kawasaki (JP)

( * ) Notice: Subject to any disclaimer, the term of this patent is extended or adjusted under 35 U.S.C. 154(b) by 767 days.

(21) Appl. No.: 18/029,374

(22) PCT Filed: Sep. 29, 2021

(86) PCT No.: PCT/JP2021/035967

§ 371 (c)(1),
(2) Date: Mar. 29, 2023

(87) PCT Pub. No.: WO2022/071435

PCT Pub. Date: Apr. 7, 2022

(65) Prior Publication Data

US 2023/0357328 A1 Nov. 9, 2023

Related U.S. Application Data

(60) Provisional application No. 63/236,927, filed on Aug. 25, 2021.

(30) Foreign Application Priority Data

Sep. 30, 2020 (JP) ................................ 2020-164630
Apr. 30, 2021 (WO) .................. PCT/JP2021/017159

(51) Int. Cl.

| | |
|---|---|
| ***C12Q 1/02*** | (2006.01) |
| ***A61K 40/11*** | (2025.01) |
| ***A61K 40/32*** | (2025.01) |
| ***A61K 40/46*** | (2025.01) |
| ***C07K 14/165*** | (2006.01) |
| ***C07K 16/102*** | (2026.01) |
| ***C12N 5/078*** | (2010.01) |
| ***C12N 5/0783*** | (2010.01) |

(52) U.S. Cl.

CPC ............ *C07K 14/165* (2013.01); *A61K 40/11* (2025.01); *A61K 40/32* (2025.01); *A61K 40/46* (2025.01); *C07K 16/102* (2026.01); *C12N 5/0638* (2013.01); *C12Q 1/025* (2013.01)

(58) Field of Classification Search

None

See application file for complete search history.

(56) References Cited

U.S. PATENT DOCUMENTS

| | | | | |
|---|---|---|---|---|
| 10,973,909 B1 * | 4/2021 | Csiszovszki ......... | C07K 14/005 |
| 11,414,700 B2 * | 8/2022 | Perera .................. | C12Q 1/6886 |
| 2006/0257852 A1 | 11/2006 | Rappuoli et al. | |
| 2023/0083931 A1 * | 3/2023 | Gaynor .................. | A61K 39/12 424/186.1 |
| 2023/0190915 A1 * | 6/2023 | De Groot ................ | A61P 31/14 424/221.1 |

FOREIGN PATENT DOCUMENTS

| | | |
|---|---|---|
| CN | 111440229 A | 7/2020 |
| CN | 112034174 A | 12/2020 |
| EP | 3091074 A | 11/2016 |
| WO | 2004/092360 A2 | 10/2004 |
| WO | 2015/075939 A | 5/2015 |

OTHER PUBLICATIONS

Kared et al. (BioRxiv Oct. 2020).*
Dionne et al. (Cancer Immunological Therapy, 2004, vol. 53, p. 307-314).*
Qamar, et al; Designing of a next generation multiepitope based vaccine (MEV) against SARS-COV-2: Immunoinformatics and in silico approaches; PLOS ONE; Dec. 22, 2020; 15(12):e0244176; 36 pgs.
Akhand, et al; Genome based evolutionary lineage of SARS-CoV-2 towards the development of novel chimeric vaccine; Infection, Genetics and Evolution; Nov. 2020; 85:104517; 20 pgs.
Berg, et al; Mandated Bacillus Calmette-Guerin (BCG) vaccination predicts flattened curves for the spread of COVID-19; Sci. Adv.; Aug. 5, 2020; 6(32):eabc1463; 7 pgs.
Bussmann, et al; Antigenic and cellular localization analysis of the severe acute respiratory syndrome coronavirus nucleocapsid protein using monoclonal antibodies; Virus Research; Dec. 2006; 122 (1-2); pp. 119-126.

(Continued)

*Primary Examiner* — Agnieszka Boesen
(74) *Attorney, Agent, or Firm* — Kilpatrick Townsend & Stockton LLP

(57) ABSTRACT

The present invention provides epitope peptides which are derived from SARS-CoV-2 proteins and have the ability to induce cytotoxic T cells. The present invention also provides polynucleotides encoding the peptides, antigen-presenting cells that present the peptides, and cytotoxic T cells that target the peptides, and methods of inducing the antigen-presenting cells or CTLs. The present invention further provides compositions and pharmaceutical compositions containing them as active ingredients. Moreover, the present invention provides methods of treating and/or preventing coronavirus infectious diseases, and/or suppressing the aggravation of coronavirus infectious diseases by using the peptides, polynucleotides, antigen-presenting cells, cytotoxic T cells, or pharmaceutical compositions of the present invention. The present invention also provides methods of inducing an immune response against coronavirus infection. Furthermore, the present invention provides methods of examining the history of coronavirus infection by detecting TCR sequences of a subject.

7 Claims, 7 Drawing Sheets

Specification includes a Sequence Listing.

(56) References Cited

OTHER PUBLICATIONS

Crooke, et al.; Immunoinformatic identification of B cell and T cell epitopes in the SARS-CoV-2 proteome; Scientific Reports; Aug. 25, 2020; 10(1):14179; 15 pgs.
Giamarellos-Bourboulis, et al.; Activate: Randomized Clinical Trial of BCG Vaccination against infection in the Elderly; Cell; Oct. 15, 2020; 183(2); pp. 315-323; e9.
Grifoni, et al; A Sequence Homology and Bioinformatic Approach Can Predict Candidate Targets for Immune Responses to SARS-CoV-2; Cell Host & Microbe; Apr. 8, 2020;27(4) pp. 671-680; e2.
Hoffmann, et al; SARS-CoV-2 Cell Entry Depends on ACE2 and TMPRSS2 and is Blocked by a Clinically Proven Protease Inhibitor; Cell; Apr. 16, 2020;181(2); pp. 271-280; e8.
Ibarrondo, et al; Rapid Decay of Anti-SARS-CoV-2 Antibodies in Persons with Mild COVID-19; N. Engl. J. Med.; Sep. 10, 2020; 383(11); 2 pgs.
Jeyanathan, et al; Immunological considerations for COVID-19 vaccine strategies; Nat. Rev. Immunol.; Oct. 2020; 20(10); pp. 615-632.
Kiyotani, et al; Bioinformatic prediction of potential T cell epitopes for SARS-Cov-2; J. Human Genetics; May 6, 2020; 65; pp. 569-575.
Le Bert, et al; SARS-CoV-2-specific T cell Immunity in cases of COVID-19 and SARS, and uninfected controls; Nature; Aug. 2020.; 584(7821); pp. 457-462.
Long, et al; Clinical and immunological assessment of asymptomatic SARS-CoV-2 infections; Nature Medicine; Aug. 2020.; 26(8); pp. 1200-1211.
Marchi, et al; Characterization of antibody response in asymptomatic and symptomatic SARS-CoV-2 infection; PLOS ONE; Jul. 2, 2021;16(7):e0253977; 18 pgs.
Miyazaki, et al; Highly restricted T-cell receptor repertoire in the CD8+ T-cell response against an HIV-1 epitope with a stereotypic amino acid substitution; AIDS; Mar. 27, 2009; 23(6); pp. 651-660.
Netea, et al; Trained Immunity: a Tool for Reducing Susceptibility to and the Severity of SARS-CoV-2 Infection; Cell; May 28, 2020;181(5); pp. 969-977.
Qamar, et al; Designing of a next generation multiepitope based vaccine (MEV) against SARS-CoV-2: Immunoinformatics and in silico approaches; PLOS ONE; Dec. 22, 2020; 159(12):e0244176; 36 pgs.
Tanaka, et al; Single-Cell Analysis of T-Cell Receptor Repertoire of HTLV-1 Tax-Specific Cytotoxic T Cells in Allogeneic Transplant Recipients with Adult T-Cell Leukemia/Lymphoma; Cancer Research; Aug. 1, 2010; 70(15); pp. 6181-6192.
Toyoshima, et al; SARS-CoV-2 genomic variations associated with mortality rate of COVID-19; J. Human Genetics; Dec. 2020; 65(12); pp. 1075-1082.
Wu, et al; A new coronavirus associated with human respiratory disease in China; Nature; Mar. 2020; 579(7798); pp. 265-269.
Zheng, et al; Functional exhaustion of antiviral lymphocytes in COVID-19 patients; Cellular & Molecular Immunology; May 2020; 17(5); pp. 533-535.
Zhong, et al; CTL Recognition of a Protective Immunodominant Influenza A Virus Nucleoprotein Epitope Utilizes a Highly Restricted Vβ but Diverse Vα Repertoire: Functional and Structural Implications; J. Mol. Biol.; Sep. 14, 2007; 372(2); pp. 535-548.
Kiyotani, et al.; U.S. Appl. No. 18/270,590; SARS-COV-2 Protein-Derived Peptide and Vaccine Containing Same; filed Jun. 30, 2023.
National Cancer Center; Brightpath Biotherapeutics; Identification of Candidate Peptides for COVID-19 Vaccine Towards the Development of Innovative Vaccines Characterized by its Induction of Cellular Immunity; Press release; 2020; www.ncc.go.jp/jp/information/pr_release/2020/0730/index.html.
Kanduc, "From Anti-SARS-CoV-2 Immune Responses to COVID-19 via Molecular Mimicry", Antibodies, Jul. 16, 2020; 9(3):33, 12 pages.
Kubo et al., "Definition of Specific Peptide Motifs for Four Major HLA-A Alleles," J Immunol. Apr. 15, 1994;152(8):3913-24.
Kondo et al., "Prominent Roles of Secondary Anchor Residues in Peptide Binding to HLA-A24 Human Class I Molecules," J Immunol. Nov. 1, 1995;155(9):4307-12.
Rammensee et al., "MHC ligands and peptide motifs: first listing," Immunogenetics. 1995;41(4):178-228.
Falk et al., "Allele-specific motifs revealed by sequencing of self-peptides eluted from MHC molecules," Nature. May 23, 1991;351(6324):290-6.
Zaremba et al., "Identification of an Enhancer Agonist Cytotoxic T Lymphocyte Peptide from Human Carcinoembryonic Antigen," Cancer Res. Oct. 15, 1997;57(20):4570-7.
Gao et al., "Predicting the Immunogenicity of T cell epitopes: From HIV to SARS-CoV-2." BioRxiv, May 15, 2020, 22 pages.
Lin et al., "Epitope-based peptide vaccines predicted against novel coronavirus disease caused by SARS-CoV-2," Virus Research, Oct. 15, 2020, 288:198082, 10 pages.
Feng et al., "Multi-epitope vaccine design using an immunoinformatics approach for 2019 novel coronavirus SARS-CoV-2)," BioRxiv, Jun. 30, 2020, 34 pages.
Qamar, et al; Designing of a next generation multiepitope based vaccine (MEV) against SARS-COV-2 : Immunoinformatics and in silico approaches; bioRxiv preprint doi: https://doi.org/10.1101/2020.02.28.970343; Mar. 2, 2020; 55 pgs.

* cited by examiner

SARS-COV-2 PROTEIN-DERIVED PEPTIDE AND VACCINE CONTAINING SAME

The present application is a national stage entry under 35 U.S.C. § 371 of International Patent Application No. PCT/JP2021/035967, filed Sep. 29, 2021, which claims priority to U.S. Provisional Patent Application No. 63/236,927, filed Aug. 25, 2021, International Application No. PCT/JP2021/017159, filed Apr. 30, 2021, and Japanese Patent Application No. 2020-164630 filed on Sep. 30, 2020, the disclosures of which are herein incorporated by reference in their entirety for all purposes.

TECHNICAL FIELD

The present invention relates to the field of biological science, more specifically to the field of prevention of virus infectious diseases. In particular, the present invention relates to novel peptides that are effective as vaccines for preventing infection, methods for either or both of preventing and treating infectious diseases using the peptide(s), and pharmaceutical compositions comprising the peptide(s).

BACKGROUND ART

The respiratory infectious disease (Coronavirus Disease 2019: COVID-19) caused by infection with the novel coronavirus (Severe Acute Respiratory Syndrome Coronavirus 2: SARS-CoV-2) has spread around the world since it was first reported in Wuhan, China.

According to the report from the World Health Organization (WHO), as of September 2020, the number of infected people exceeded 27 million and the number of deaths reached 890 thousand. Moreover, as of April 2021, the number of infected people exceeded 120 million and the number of deaths reached 2.8 million. Effective means for stopping the spread of infection include preventive vaccination; however, there is no vaccine against COVID-19 that has been put to practical use.

It has been previously known that BCG vaccine has a preventive effect even against infectious diseases other than tuberculosis. A recent study has also reported that BCG vaccination of elderly people aged 65 years and older showed a suppressive effect on infectious diseases (NPL 1: Giamarellos-Bourboulis E J et al., Cell 2020, Online ahead of print).

An association has been suggested between suppression of fatality rates or growth rates of deaths in COVID-19 and BCG vaccination (NPL 2: Toyoshima Y et al., J Hum Genet 2020, Online ahead of print; NPL 3: Berg M K et al., Science Advances 2020, Online ahead of print).

In the human defense mechanism against viral infection, innate immune responses led by immune cells (such as macrophages, NK cells, and neutrophils) work first, and then antigen-specific immune responses are developed by acquired immunity (humoral immunity and cellular immunity) led by B cells and T cells. After BCG vaccination, the activity of transcribing inflammatory cytokines is enhanced in immune cells, and infection with a virus in this state (trained immunity) triggers rapid release of inflammatory cytokines in the body. This is presumed to result in humoral immune responses by activated B cells and cellular immune responses by T cells suppressing viral proliferation (NPL 4: Netea M G et al., Cell 2020, 181(5): 969-977).

It is the spike protein that plays a central function in the entry of SARS-CoV-2 into human cells (NPL 5: Hoffmann M et al., Cell 2020, 181(2): 271-280). Most of the vaccines against COVID-19 currently under research and development are primarily aimed at inducing neutralizing antibodies (inducing humoral immunity) against the spike protein of SARS-CoV-2 (NPL 6: Jeyanathan M et al., Nat Rev Immunol 2020, Online ahead of print). However, repeated proliferation of SARS-CoV-2 may cause mutations in its viral genome. When a mutation occurs in the gene encoding the spike protein, vaccine-induced neutralizing antibodies may become ineffective. Moreover, studies conducted on people who had recovered from COVID-19 suggest that neutralizing antibodies induced in the human body may be short-lived (NPL 7: Ibarrondo F J et al., N Engl J Med 2020, 383(11): 1085-1087; NPL 8: Long Q X et al., Nat Med 2020, 26(8): 1200-1204). Accordingly, there are concerns that problems remain in the development of vaccines aimed at inducing humoral immunity by neutralizing antibodies.

Cellular immunity by T cells is also very important as a defense reaction against infectious diseases. Cytotoxic T lymphocytes (CTLs) are CD8-positive T cells and are induced by presentation of viral antigens (epitope peptides derived from viral proteins) by dendritic cells (DCs). Then, CTLs recognize epitope peptides presented on human leukocyte antigen (HLA) class I molecules expressed on the surface of virus-infected cells and kill these cells. This action destroys the infected cells, where viral particles are replicated, and results in suppression of viral proliferation. Compared to neutralizing antibodies, which mainly inhibit new infection of cells with replicated viral particles, CTLs, which target the replication process itself of viral particles, have a more direct effect in preventing viral proliferation. Accordingly, CTLs are considered to play a role in eliminating viruses from the living body and suppressing aggravation of infectious diseases. The report that the peripheral blood of patients with severe COVID-19 shows a marked decrease in CD8-positive T cells compared to healthy individuals suggests that CTLs are an important factor in suppressing aggravation of COVID-19 (NPL 9: Zheng M et al., Cell Mol Immunol 2020, 17(5): 533-535).

Furthermore, part of CTLs are known to remain in the body as memory T cells for a long time. In 2003, the SARS-CoV epidemic occurred and more than 8,000 people were infected. Because of the fact that, 17 years after the epidemic, CTLs against SARS-CoV were still detected in the blood of people who had recovered (NPL 10: Le Bert N et al., Nature 2020, 584(7821): 457-462), CTLs against SARS-CoV-2 may also remain in the body for a long time after being induced.

Accordingly, a vaccine aimed at eliciting cellular immunity can be an effective preventive measure against COVID-19. It is considered that CTLs induced by a vaccine comprising an epitope peptide derived from a SARS-CoV-2 protein remain in the body as memory T cells and show cytotoxic activity against virus-infected cells rapidly after SARS-CoV-2 infection, leading to suppression of aggravation of COVID-19. Thus, it is desired to identify an epitope peptide derived from a SARS-CoV-2 protein that can induce CTLs in the human body.

Candidate epitope peptides determined based on bioinformatics have been reported; however, it has not been verified whether or not they actually bind to an HLA and have the ability to induce CTLs, and no epitope peptide has been identified (NPL 11: Grifoni A et al., Cell Host Microbe 2020, 27(4): 671-680; NPL12: Crooke S N et al., Sci Rep 2020, 10(1): 14179).

Furthermore, in taking measures to stop the spread of SARS-CoV-2 infection, it is important to accurately understand each individual's history of infection. Currently, it has become mainstream to perform an antibody test in order to examine the history of infection; however, antibody titers may be very low in asymptomatic people and infected people showing only mild symptoms (see NPL 13: Marchi S et al., PLoS One 2021, 16(7): e0253977; NPL 8: Long Q X et al., Nat Med 2020, 26(8): 1200-1204). Such facts may limit antibody tests, and a new testing method is desired. In addition to humoral immunity, led by antibodies, cellular immunity, led by T cells, also plays an important role in controlling viral infection. Cytotoxic T lymphocytes (CTLs) recognize, through their T cell receptors (TCRs), viral protein-derived peptides presented on major histocompatibility complex (MHC) class I molecules on the surface of virus-infected cells, and then injure these cells. The T cell response to viral infection is considered to be manifested as, e.g., a marked increase or decrease in a particular TCR in comprehensive analysis of TCRs derived from peripheral blood T cells. TCRs derived from SARS-CoV-2-specific CTLs may serve as important markers for understanding SARS-CoV-2 infection.

CITATION LIST

Non-Patent Literature

[NPL 1] Giamarellos-Bourboulis E J et al., Cell 2020, Online ahead of print (Volume 183, Issue 2, 2020, Pages 315-323.e9)

[NPL 2] Toyoshima Y et al., J Hum Genet 2020, Online ahead of print (65, pages 1075-1082, 2020)

[NPL 3] Berg M K et al., Science Advances 2020, Online ahead of print (Vol 6, No. 32: eabc1463, 2020)

[NPL 4] Netea M G et al., Cell 2020, 181(5):969-977

[NPL 5] Hoffmann M et al., Cell 2020, 181(2):271-280

[NPL 6] Jeyanathan M et al., Nat Rev Immunol 2020, Online ahead of print (20, 615-632, 2020)

[NPL 7] Ibarrondo F J et al., N Engl J Med 2020, 383(11): 1085-1087

[NPL 8] Long Q X et al., Nat Med 2020, 26(8):1200-1204

[NPL 9] Zheng M et al., Cell Mol Immunol 2020, 17(5): 533-535

[NPL 10] Le Bert N et al., Nature 2020, 584(7821):457-462

[NPL 11] Grifoni A et al., Cell Host Microbe 2020, 27(4): 671-680

[NPL 12] Crooke S N et al., Sci Rep 2020, 10(1):14179

[NPL 13] Marchi S et al., PLoS One 2021, 16(7): e0253977

SUMMARY OF INVENTION

The present invention provides epitope peptides that bind to HLA-A*24:02 or HLA-A*02:01 and have the ability to induce CTLs, which are selected from peptides derived from four structural proteins and six non-structural proteins that SARS-CoV-2 (reference sequence: GenBank accession number MN908947 (SEQ ID NO: 16)) has.

The four structural proteins specifically refer to the following proteins:

spike protein (reference sequence: GenBank accession number QHD43416 (SEQ ID NO: 17)); envelope protein (reference sequence: GenBank accession number QHD43418 (SEQ ID NO: 18)); matrix protein (reference sequence: GenBank accession number QHD43419 (SEQ ID NO: 19)); and nucleoprotein (reference sequence: GenBank accession number QHD43423 (SEQ ID NO: 20)).

On the other hand, the six non-structural proteins specifically refer to the following proteins:

ORF1ab (reference sequence: GenBank accession number QHD43415 (SEQ ID NO: 21)); ORF3a (reference sequence: GenBank accession number QHD43417 (SEQ ID NO: 22)); ORF6

(reference sequence: GenBank accession number QHD43420 (SEQ ID NO: 23)); ORF7a (reference sequence: GenBank accession number QHD43421 (SEQ ID NO: 24)); ORF8

(reference sequence: GenBank accession number QHD43422 (SEQ ID NO: 25)); and ORF10

(reference sequence: GenBank accession number QHI42199 (SEQ ID NO: 26)).

The epitope peptides of the present invention are demonstrated to be able to induce specific and potent immune responses against COVID-19 targeting HLA-A*24:02-positive individuals, who constitute a large population in Asian countries including Japan, or targeting HLA-A*02:01-positive individuals, who constitute a large population in Europe and the United States (Cao K et al., Hum Immunol 2001, 62(9): 1009-1030; Gonzalez-Galarza F F et al., Nucleic Acids Res 2020, 48(D1): D783-D788).

Since the amino acid sequences of the epitope peptides provided in the present invention have low similarity to those derived from human proteins, creation of highly safe vaccines that are less likely to cause unexpected side reactions can be expected. On the other hand, since those amino acid sequences are commonly found in SARS-CoV and MERS-CoV, which were epidemic in the past, they may also be found in proteins of new types of coronaviruses that will emerge in the future. Accordingly, vaccines comprising such epitope peptide can be effective against not only the current SARS-CoV-2 but also coronavirus infectious diseases that will be prevalent in the future.

The present invention also provides compositions comprising one or more types of peptides of the present invention, one or more types of polynucleotides encoding one or more types of peptides of the present invention, APCs of the present invention, exosomes presenting peptides of the present invention, and/or CTLs of the present invention. The compositions of the present invention are preferably pharmaceutical compositions. The pharmaceutical compositions of the present invention can be used for treating and/or preventing coronavirus infectious diseases, as well as suppressing aggravation. They can also be used for inducing an immune response against coronavirus infection. When administered to a subject, a peptide of the present invention is presented on the surface of an APC, and as a result CTLs targeting the peptide are induced. Therefore, another objective of the present invention is to provide compositions inducing CTLs, wherein the compositions comprise one or more types of peptides of the present invention, one or more types of polynucleotides encoding one or more types of peptides of the present invention, APCs of the present invention, and/or exosomes presenting peptides of the present invention.

A further objective of the present invention is to provide methods of inducing APCs having CTL-inducing ability, wherein the methods comprise a step of contacting one or more types of peptides of the present invention with an APC, or a step of introducing a polynucleotide encoding any one peptide of the present invention into an APC.

The present invention further provides a method of inducing CTLs, comprising a step of co-culturing a CD8-positive T cell with an APC that presents on its surface a complex of an HLA antigen and a peptide of the present invention, a step of co-culturing a CD8-positive T cell with an exosome that presents on its surface a complex of an HLA antigen and a peptide of the present invention, or a step of introducing into a CD8-positive T cell a vector comprising a polynucleotide encoding each subunit of a T cell receptor (TCR) capable of binding to a peptide of the present invention presented by an HLA antigen on a cell surface.

A further objective of the present invention is to provide isolated APCs that present on their surface a complex of an HLA antigen and a peptide of the present invention. The present invention further provides isolated CTLs targeting a peptide of the present invention. These APCs and CTLs can be used in immunotherapy for coronavirus infectious diseases.

Another objective of the present invention is to provide methods of inducing an immune response against coronavirus infection in a subject, wherein the methods comprise a step of administering to the subject a peptide(s) of the present invention, a polynucleotide(s) encoding the peptide(s), an APC(s) of the present invention, an exosome(s) presenting a peptide(s) of the present invention, and/or a CTL(s) of the present invention. Another objective of the present invention is to provide methods of treating and/or preventing coronavirus infectious disease, as well as suppressing aggravation in a subject, wherein the methods comprise a step of administering to the subject a peptide(s) of the present invention, a polynucleotide(s) encoding the peptide(s), an APC(s) of the present invention, an exosome(s) presenting a peptide(s) of the present invention, and/or a CTL(s) of the present invention.

The present invention also relates to TCRs expressed by T cells that recognize a SARS-CoV-2 protein-derived peptide. TCR is a protein molecule consisting of a dimer of an α chain and a 3 chain. Human T cells recognize peptides presented on MHC class I (also known as human leukocyte antigen, HLA) molecules through TCRs. As a result, T cell proliferation, differentiation, cytokine production, cytotoxic substance (perform and granzymes) secretion and the like are induced.

The TCRα gene comprises Vα, Jα, and Cα genes. The TCRβ gene comprises Vβ, Dβ, Jβ, and Cβ genes. The regions determining the specificity of TCR for a peptide are called complementarity determining regions (CDRs), which include CDR1, CDR2, and CDR3. Of these, CDR3 contacts a peptide directly, and therefore its amino acid sequence is very important in determining specificity. In the TCR c chain, V-J corresponds to CDR3, and in the TCR β chain, V-D and D-J correspond to CDR3. Insertion and deletion of nucleotides generate their diversity.

SARS-CoV-2 infection or vaccination may selectively increase T cells that recognize SARS-CoV-2 protein-derived peptides. For the purpose of examining such an immune response in the form of an altered frequency of detection of a particular TCR in the peripheral blood, the amino acid sequences of TCRs shown herein (in particular, CDR3 amino acid sequences), which have been identified from T cells recognizing SARS-CoV-2 protein-derived peptides, are of great use. That is, an objective of the present invention is to provide methods of knowing the immune response of a subject to SARS-CoV-2, the method comprising determining the detection frequency of TCRs in the peripheral blood of the subject.

In addition to the above, other objects and features of the present invention will become more fully apparent when the following detailed description is read in conjunction with the accompanying figures and examples. However, it is to be understood that both the foregoing summary of the present invention and the following detailed description are of exemplified embodiments, and not restrictive of the present invention or other alternate embodiments of the present invention. In particular, while the present invention is described herein with reference to a number of specific embodiments, it will be appreciated that the description is illustrative of the present invention and is not constructed as limiting of the present invention. Various modifications and applications may occur to those who are skilled in the art, without departing from the spirit and the scope of the present invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

FIG. 6-2 shows the continuation of FIG. 6-1.

DESCRIPTION OF EMBODIMENTS

Figure 1:
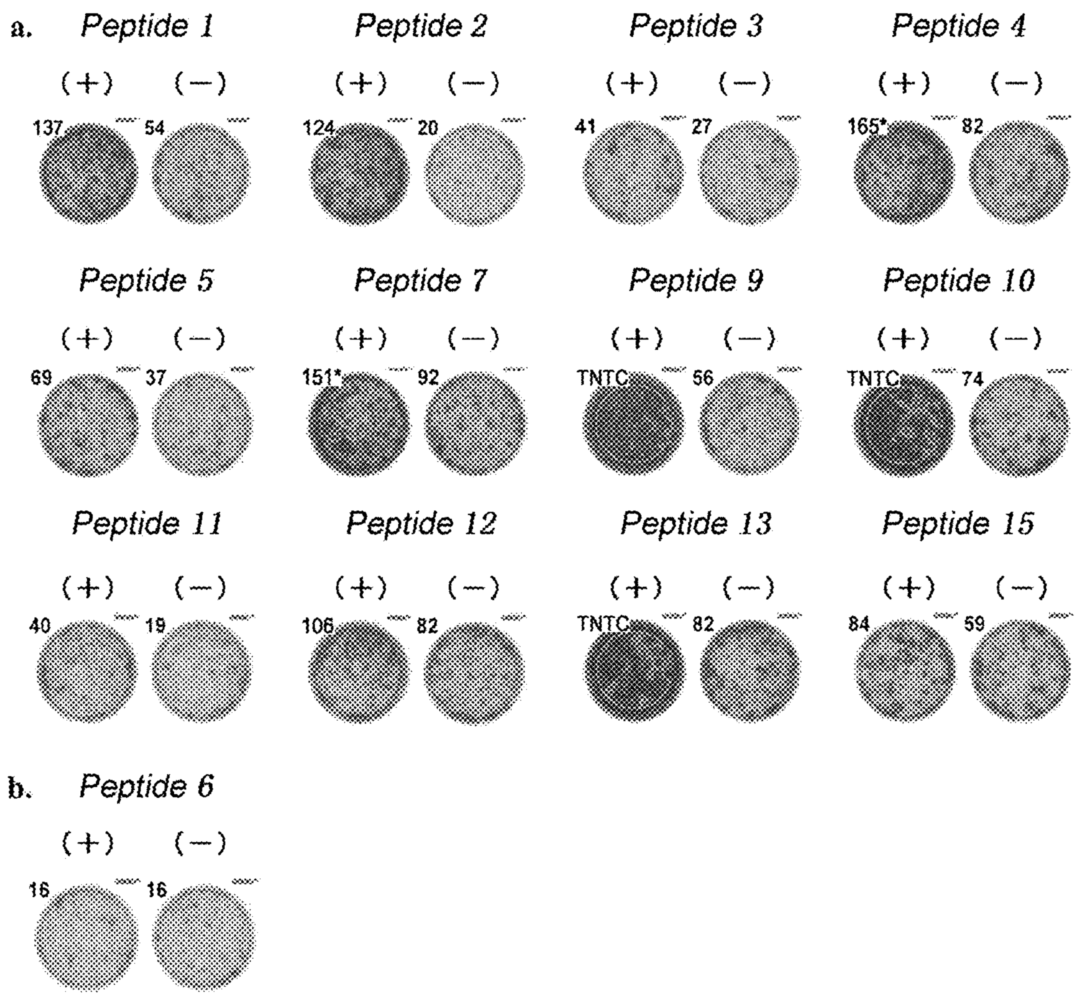
FIG. 1 is composed of images showing the results of IFN-γ enzyme-linked immunospot (ELISPOT) assays performed using cells induced with peptides derived from SARS-CoV-2 proteins. In the figure, "(+)" indicates IFN-γ production for HLA-A*24:02-expressing target cells (TISI cells) pulsed with a peptide of interest, and "(−)" indicates IFN-γ production for TISI cells not pulsed with any peptide (negative control). It can be seen by comparison with the negative control that peptide-specific IFN-γ production was observed for Peptide 1 (SEQ ID NO: 1), Peptide 2 (SEQ ID NO: 2), Peptide 3 (SEQ ID NO: 3), Peptide 4 (SEQ ID NO: 4), Peptide 5 (SEQ ID NO: 5), Peptide 7 (SEQ ID NO: 7), Peptide 9 (SEQ ID NO: 9), Peptide 10 (SEQ ID NO: 10), Peptide 11 (SEQ ID NO: 11), Peptide 12 (SEQ ID NO: 12), Peptide 13 (SEQ ID NO: 13) and Peptide 15 (SEQ ID NO: 15) (FIG. 1*a*). On the other hand, Peptide 6 (SEQ ID NO: 6) is shown as an example of typical negative data for which no peptide-specific IFN-γ production was observed (FIG. 1*b*).

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

I. Definitions

The words "a", "an", and "the" as used herein mean "at least one" unless otherwise specifically indicated.

The terms "isolated" and "purified" used in relation with a substance (for example, peptide, antibody, polynucleotide or such) indicate that the substance does not substantially contain at least one substance that may else be included in a natural source. Thus, an isolated or purified peptide refers to a peptide that does not substantially contain another cellular material, for example, carbohydrate, lipid and other contaminating proteins from the cell or tissue source from which the peptide is derived. When the peptide is chemically synthesized, an isolated or purified peptide refers to a peptide that does not substantially contain a precursor substance or another chemical substance. The phrase "does not substantially contain a cellular material" includes peptide preparations in which the peptide is separated from cellular components of the cells from which it is isolated or recombinantly produced. Thus, a peptide that does not substantially contain a cellular material encompasses peptide preparations that contain less than about 30%, 20%, 10%, or 5%, 3%, 2% or 1% (dry weight basis) of other cellular materials. When the peptide is recombinantly produced, an isolated or purified peptide does not substantially contain culture medium, which encompasses peptide preparations that contain culture medium less than about 20%, 10%, or 5%, 3%, 2% or 1% (dry weight basis) of the volume of the peptide preparation. When the peptide is chemically synthesized, an isolated or purified peptide does not substantially contain a precursor substance or other chemical substances, which encompasses peptide preparations that contain a precursor substance or other chemical substances less than about 30%, 20%, 10%, 5%, 3%, 2% or 1% (dry weight basis) of the volume of the peptide preparation. That a particular peptide preparation is an isolated or purified peptide can be confirmed, for example, by the appearance of a single band following sodium dodecyl sulfate (SDS)-polyacrylamide gel electrophoresis and Coomassie Brillliant Blue staining or such of the gel. In a preferred embodiment, the peptides and polynucleotides of the present invention are isolated or purified.

The terms "polypeptide", "peptide", "protein" and "protein" are used interchangeably herein, and refer to polymers of amino acid residues. These terms are applied to also non-naturally occurring amino acid polymers comprising one or more non-naturally occurring amino acid residues, in addition to naturally occurring amino acid polymers. Non-naturally occurring amino acids include amino acid analogs, amino acid mimetics, and such.

The term "amino acid" as used herein refers to naturally occurring amino acids, as well as amino acid analogs and amino acid mimetics that function similarly to the naturally occurring amino acids. Naturally occurring amino acids are those encoded by the genetic code, as well as those modified after translation in cells (e.g., hydroxyproline, gamma-carboxyglutamate, and O-phosphoserine, etc.). The phrase "amino acid analog" refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine sulfoxide, methionine methyl sulfonium, and such). The phrase "amino acid mimetic" refers to chemical compounds that have different structures but similar functions to general amino acids. Amino acids can be either L-amino acids or D-amino acids, and the peptides of the present invention are preferably L-amino acid polymers.

The terms "polynucleotide", "oligonucleotide" and "nucleic acid" are used interchangeably herein, and refer to a polymer of nucleotides.

The term "composition" used in the present specification is intended to encompass products that include specified ingredients in specified amounts, and any products generated directly or indirectly from combination of specified ingredients in the specified amounts. When the composition is a pharmaceutical composition, the term "composition" is intended to encompass products including active ingredient(s) and inert ingredient(s), as well as any products generated directly or indirectly from combination, complexation or aggregation of any two or more ingredients, from dissociation of one or more ingredients, or from other types of reactions or interactions of one or more ingredients. Thus, the pharmaceutical compositions of the present invention encompass any compositions made by admixing compounds or cells of the present invention with a pharmaceutically or physiologically acceptable carrier. Without being limited thereto, the terms "pharmaceutically acceptable carrier" or "physiologically acceptable carrier" used in the present specification include liquid or solid bulking agents, diluents, excipients, solvents, and encapsulation materials; and mean pharmaceutically or physiologically acceptable materials, compositions, substances or media.

Unless otherwise specified, the term "virus infectious disease" refers to a coronavirus infectious disease; and examples of coronaviruses include SARS-CoV-2, MERS-CoV, SARS-CoV and such, without being limited thereto. In an exemplary embodiment, the "coronavirus infectious disease" is SARS-CoV-2 infectious disease in an HLA-A24- or HLA-A02-positive subject.

Unless otherwise specified, the terms "cytotoxic T lymphocyte", "cytotoxic T cell" and "CTL" are used interchangeably herein. Unless otherwise specifically indicated, they refer to a sub-group of T lymphocytes that can recognize non-self cells (for example, tumor/cancer cells, virus-infected cells) and induce the death of such cells.

Unless otherwise specified, the term "HLA-A24" refers to the HLA-A24 type which includes subtypes such as HLA-A*24:01, HLA-A*24:02, HLA-A*24:03, HLA-A*24:04, HLA-A*24:07, HLA-A*24:08, HLA-A*24:20, HLA-A*24:25 and HLA-A*24:88.

Unless otherwise specified, the term "HLA-A02 (or HLA-A2)" refers to the HLA-A02 type which includes subtypes such as HLA-A*02:01, HLA-A*02:02, A*02:03, A*02:04, A*02:05, A*02:06, A*02:07, A*02:10, A*02:11, A*02:13, A*02:16, A*02:18, A*02:19, A*02:28 and A*02:50.

Unless otherwise specified, the term "coronavirus protein" refers to a protein consisting of the full-length amino acid sequence of each protein encoded by coronavirus genome sequences. Preferred examples include structural and non-structural proteins of SARS-CoV-2. Moreover, examples of coronaviruses include, but are not limited to, SARS-CoV-2, MERS-CoV, and SARS-CoV. The genome sequence (reference sequence) of each of these coronaviruses and the amino acid sequences of coronavirus proteins encoded by it can be obtained with, for example, the following Genbank accession numbers:

SARS-CoV-2: MN908947

MERS-CoV: JX869059

SARS-CoV: Tor2: AY274119, BJO1: AY278488, or GZ02: AY390556

Unless otherwise specified, the term "SARS-CoV-2 protein" refers to a protein consisting of the full-length amino acid sequence of each protein encoded by the SARS-CoV-2 genome sequence, and includes the four structural proteins and six non-structural proteins that SARS-CoV-2 has. The four structural sequences and six non-structural proteins are listed in Table 1. In the table, as for the non-structural protein orf1ab, two ORFs in the reference sequence, 266 . . . 13468 and 13468 . . . 21555, are linked to form a single ORF by ribosomal frameshifting.

TABLE 1

| | Protein | Reference Sequence: GenBank accession number | Coding Sequence (CDS) in Genome Sequence (MN908947.3) | Amino Acid Sequence (SEQ ID NO) |
|---|---|---|---|---|
| Four Structural Proteins | Spike Protein | QHD43416 | 21563 . . . 25384 | 17 |
| | Envelope Protein | QHD43418 | 26245 . . . 26472 | 18 |
| | Matrix Protein | QHD43419 | 26523 . . . 27191 | 19 |
| | Nucleoprotein | QHD43423 | 28274 . . . 29533 | 20 |
| Six Non-structural Proteins | ORF1ab | QHD43415 | 266 . . . 13468, 13468 . . . 21555 | 21 |
| | ORF3a | QHD43417 | 25393 . . . 26220 | 22 |
| | ORF6 | QHD43420 | 27202 . . . 27387 | 23 |
| | ORF7a | QHD43421 | 27394 . . . 27759 | 24 |
| | ORF8 | QHD43422 | 27894 . . . 28259 | 25 |
| | ORF10 | QHI42199 | 29558 . . . 29674 | 26 |

Unless otherwise specified, the terms "coronavirus-infected cells", "virus-infected cells", and "infected cells" are herein used interchangeably, and refer to cells infected with a coronavirus unless otherwise specifically indicated. Examples of coronaviruses include, but are not limited to, SARS-CoV-2, MERS-CoV, and SARS-CoV.

As used herein, the term "infection" includes viral entry and/or viral proliferation in cells or body tissues, and disease conditions resulting from viral entry and viral proliferation. The entry by viral life cycle and the proliferation stage of viral life cycle include, but are not limited to, binding of the viral particle to a cell, introduction of the viral genetic information into the cell, expression of viral proteins, production of new viral particles, and release of the viral particles from the cell.

In the context of a subject or patient, the phrase "HLA antigen of a subject (or patient) is HLA-A24 or HLA-A02" used herein refers to that a subject or patient has the HLA-A24 or HLA-A02 antigen gene homozygously or heterozygously as the MHC (Major Histocompatibility Complex) Class I molecule, and that the HLA-A24 or HLA-A02 antigen is expressed in the cells of the subject or patient as the HLA antigen.

As long as the methods and compositions of the present invention are useful in the context of coronavirus infectious disease "treatment", the treatment is considered "efficacious" when it achieves clinical advantages, for example, alleviation of clinical symptoms of coronavirus infectious disease, suppression of aggravation in a subject. Fever, cough, chills, rigors, myalgia and the like are commonly known as main symptoms of coronavirus infectious diseases. It is considered that many infected patients have mild symptoms and recover within about one to two weeks. However, part of patients show symptoms of respiratory distress and may have marked dyspnea, hypoxia, or even acute respiratory distress syndrome (ARDS). According to recent reports, particularly in SARS-CoV-2-infected patients, unique symptoms such as dysosmia and dysgeusia have also been observed in patients with relatively mild symptoms. On the other hand, thrombi and cytokine storms in severely ill patients are known to result in aggravation. When treatment is applied prophylactically, the term "efficacious" means that the treatment retards or prevents development of a coronavirus infectious disease, or prevents or alleviates the clinical symptoms of a coronavirus infectious disease. Effectiveness is determined in relation to any known method for diagnosing or treating a coronavirus infectious disease. For example, when any of the specific symptoms mentioned above is suppressed, the effectiveness of the treatment or prevention is indicated.

As long as the methods and compositions of the present invention are useful in the context of coronavirus infectious disease "prevention (prophylaxis)", the term "prevention (prophylaxis)" herein includes any work that eases the load of disease-associated mortality or morbidity. Prevention (Prophylaxis) can be carried out at the "primary, secondary and tertiary prevention (prophylaxis) levels". Whereas the primary prevention (prophylaxis) avoids the development of a disease, prevention (prophylaxis) at the secondary and tertiary levels encompasses prevention (prophylaxis) of disease progression and appearance of symptoms, as well as workings intended to reduce adverse effects of the existing disease by restoring functions and reducing disease-associated complications. Alternately, prevention (prophylaxis) can include alleviation of severity of a specific disorder, for example, extensive preventive therapy intended to reduce clinical symptoms such as fever, breathlessness, and upper respiratory infection.

In the context of the present invention, the treatment and/or prevention (prophylaxis) and/or the suppression of aggravation of coronavirus infectious diseases includes retarding the development of or ameliorating at least one symptom of coronavirus infectious diseases. It also includes inhibition of viral proliferation in coronavirus-infected cells. Effective treatment and/or prevention (prophylaxis) of coronavirus infectious diseases reduces mortality, improves the prognosis of individuals affected with coronavirus infectious diseases, and alleviates symptoms associated with coronavirus infectious diseases. For example, alleviation or improvement of symptoms constitutes effective treatment and/or prevention (prophylaxis), and includes 10%, 20%, 30% or more alleviation or stable conditions of symptoms.

In the present invention, inhibition of viral proliferation includes inhibition of the viral replication process in infected cells. When each viral protein expressed in the viral replication process is presented as an antigen in virus-infected cells, CTLs induced by the peptide of the present invention injure cellular functions (gene replication and protein translation) of the infected cells by their cytotoxic activity. Alternatively, the CTLs destroy the infected cells themselves. As a result, the replication process of viral particles, which relies on the cellular functions of the infected cells, is inhibited and viral proliferation is inhibited.

Furthermore, in the present invention, suppression of aggravation means suppression of the worsening or progression of any symptom associated with coronavirus infections. Specifically, the progression of respiratory distress symptoms that requires interventional treatment such as oxygen inhalation or placement of a ventilator or extracorporeal membrane oxygenation (ECMO) is a typical example of aggravation in coronavirus infectious diseases. Thus, stopping, prevention, or alleviation of the progression (worsening) of those symptoms is included in the suppression of aggravation in the present invention.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an "antibody" herein is used in the broadest sense and specifically covers intact monoclonal antibodies, polyclonal antibodies, multispecific antibodies (e.g., bispecific antibodies) formed from two or more intact antibodies, and antibody fragments so long as they exhibit the desired biological activity. An "antibody" may be antibodies of all classes (e.g., IgA, IgD, IgE, IgG and IgM).

The present invention relates to TCRs expressed by T cells that recognize a SARS-CoV-2-derived peptide. TCR is a protein molecule consisting of a dimer of an α chain and a β chain. Human T cells recognize peptides presented on MHC class I (also known as human leukocyte antigen, HLA) molecules through TCRs. As a result, T cell proliferation, differentiation, cytokine production, cytotoxic substance (perform and granzymes) secretion and the like are induced.

The TCR-α gene comprises Vα, Jα and Cα genes. The TCR-β gene comprises Vβ, Dβ, Jβ and Cβ genes. The regions determining the specificity of TCR for a peptide are called complementarity determining regions (CDRs), which include CDR1, CDR2, and CDR3. Of these, CDR3 contacts a peptide directly, and therefore its amino acid sequence is very important in determining the antigen recognition specificity of TCR. In the TCR-α chain, V-J corresponds to CDR3, and in the TCR-β chain, V-D and D-J correspond to CDR3. Insertion and deletion of nucleotides generate their diversity.

In the present invention, a TCR refers to a protein molecule that is expressed on a T cell and consists of a dimer of an α chain and a 3 chain. In the present invention, a T cell is a human T cell and can be a human T cell that recognizes a SARS-CoV-2-derived peptide.

Furthermore, in the present invention, a TCR refers to a molecule that is expressed on a T cell, recognizes through itself a peptide presented on a MHC class I (also known as human leukocyte antigen, HLA) molecule, and induces, e.g., T cell proliferation, differentiation, cytokine production, and secretion of cytotoxic substances (perform and granzymes).

The TCR-α gene comprises Vα, Jα and Cα genes. The TCR-3 gene comprises Vβ, Dβ, Jβ and Cβ genes. The regions determining the specificity of TCR for a peptide are called complementarity determining regions (CDRs), which include CDR1, CDR2 and CDR3. Of these, CDR3 contacts a peptide directly, and therefore its amino acid sequence is very important in determining the antigen recognition specificity of TCR. In the TCR-α chain, V-J corresponds to CDR3, and in the TCR-β chain, V-D and D-J correspond to CDR3. Insertion and deletion of nucleotides generate their diversity.

In the present invention, a TCR is expressed on a T cell and may have CDR sequences that specifically recognize a SARS-CoV-2-derived peptide.

In the present invention, a "history of coronavirus infection" means that a subject has been previously infected with a coronavirus, particularly SARS-CoV-2. Even when a subject was previously infected but asymptomatic, the previous infection can be confirmed by detecting the TCRs of the present invention. Moreover, a subject who is currently infected means that the infection was previously established. Thus, a subject who is currently infected has a previous history of coronavirus infection. COVID-19 means a "novel coronavirus infectious disease (COVID-19 infection)" definitively diagnosed by physicians.

Unless otherwise specified, the technical terms and scientific terms used herein all have the same meanings as terms commonly understood by one of ordinary skill in the art to which the present invention belongs.

II. Peptides

HLA-A24 is an allele commonly seen in Asians, and HLA-A02 is an allele commonly seen in Caucasians (Sette A, Sidney J., Immunogenetics 1999, 50: 201-12; Cao K et al., Hum Immunol 2001, 62(9): 1009-1030; Gonzalez-Galarza F F et al., Nucleic Acids Res 2020, 48(D1): D783-D788). Thus, an effective method of treating coronavirus infectious diseases for a great population of Asians or Caucasians can be provided by providing SARS-CoV-2 protein-derived CTL-inducing peptides restricted to HLA-A24 or HLA-A02. Thus, the present invention provides SARS-CoV-2 protein-derived peptides that are capable of inducing CTLs in an HLA-A24- or HLA-A02-restrictive manner.

The peptides of the present invention are SARS-CoV-2 protein-derived peptides that are capable of inducing CTLs in an HLA-A24- or HLA-A02-restrictive manner. Peptides capable of inducing CTLs in an HLA-A24-restrictive manner include peptides having the amino acid sequence selected from among SEQ ID NOs: 1, 2, 3, 4, 5, 7, 9, 10, 11, 12, 13 and 15. Peptides capable of inducing CTLs in an HLA-A02-restrictive manner include peptides having the amino acid sequence selected from among SEQ ID NOs: 1, 2, 4, 7, 10, 12 and 13.

CTLs having a cytotoxic activity specific to these peptides can be established by in vitro stimulation of T cells by dendritic cells pulsed with these peptides. The established CTLs show a specific cytotoxic activity against target cells pulsed with each of the peptides.

CTLs are induced following presentation of coronavirus antigens (epitope peptides derived from coronavirus proteins) and then recognize epitope peptides presented on human leukocyte antigen (HLA) class I molecules expressed on the surface of coronavirus-infected cells to kill these cells. Thus, coronavirus antigens are excellent targets for immunotherapy. Therefore, the peptides of the present invention can be suitably used for immunotherapy of coronavirus infectious diseases. A preferred peptide is a nonapeptide (a peptide consisting of 9 amino acid residues) or a decapeptide (a peptide consisting of 10 amino acid residues), and it is more preferably a peptide consisting of the amino acid sequence selected from among SEQ ID NOs: 1, 2, 3, 4, 5, 7, 9, 10, 11, 12, 13 and 15. For example, a peptide having the amino acid sequence of SEQ ID NO: 1, 2, 4, 7, 10, 12 or 13 is suitable for induction of CTLs that show a specific cytotoxic activity against coronavirus-infected cells having HLA-A24 or HLA-02, and can be suitably used for immunotherapy of coronavirus infectious disease for HLA-A24- or HLA-A02-positive patients. In a more preferred embodiment, the peptide of the present invention is a peptide consisting of the amino acid sequence selected from among SEQ ID NOs: 1, 2, 3, 4, 5, 7, 9, 10, 11, 12, 13 and 15 for HLA-A24-positive patients, and a peptide consisting of the amino acid sequence selected from among SEQ ID NOs: 1, 2, 4, 7, 10, 12 and 13 for HLA-A02-positive patients.

For the peptides of the present invention, an additional amino acid residue(s) can be made to adjoin the amino acid sequence of the peptide of the present invention, as long as the resultant peptides retain the CTL-inducing ability of the original peptide. The additional amino acid residue(s) may be composed of any types of amino acid(s), as long as they do not impair the CTL-inducing ability of the original peptide. Therefore, the peptides of the present invention encompass peptides having CTL-inducing ability, comprising the amino acid sequence selected from among SEQ ID NOs: 1, 2, 3, 4, 5, 7, 9, 10, 11, 12, 13 and 15. Such peptides are, for example, less than about 40 amino acids, in many cases less than about 20 amino acids, and usually less than about 15 amino acids. Therefore, if the original peptide is a nonapeptide, the peptide of the present invention encompasses peptides that are 10 amino-acid long or 11-40 amino-acid long, which are produced by adjoining additional amino acid(s) to the peptide. Furthermore, if the original peptide is a decapeptide, the peptide of the present invention encompasses peptides that are 11-40 amino-acid long. Such a peptide can be, for example, a peptide that is 11-20 amino-acid long or a peptide that is 11-15 amino-acid long. A preferred example of an additional amino acid residue(s) is an amino acid residue(s) adjacent to the amino acid sequence of the peptide of the present invention in the full-length amino acid sequence of each protein encoded by a genome sequence of SARS-CoV-2 (for example, SEQ ID NOs: 17-26). Therefore, the peptides of the present invention encompass peptides comprising the amino acid sequence selected from among SEQ ID NOs: 1, 2, 3, 4, 5, 7, 9, 10, 11, 12, 13 and 15, and wherein the peptides are peptide fragments of SARS-CoV-2 protein and have CTL-inducing ability.

In general, modifications of one, two or more amino acids in a certain peptide do not affect the functions of the peptide, or in some cases even enhance the desired functions of the original peptide. In fact, modified peptides (i.e., peptides composed of the amino acid sequence in which one, two or several amino acid residues are modified (i.e., substituted, deleted, inserted, and/or added) compared to the original reference sequence) are known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention can be peptides comprising the amino acid sequence in which one, two or several amino acids are substituted, deleted, inserted and/or added to the amino acid sequence selected from among SEQ ID NOs: 1, 2, 3, 4, 5, 7, 9, 10, 11, 12, 13 and 15 and having CTL-inducing ability.

One skilled in the art can recognize that individual substitutions to an amino acid sequence that alter a single amino acid or a small percentage of amino acids tend to result in the conservation of the properties of the original amino acid side chain(s). Accordingly, those are frequently referred to as "conservative substitutions" or "conservative modifications"; and modification of a protein by "conservative substitution" or "conservative modification" may result in a modified protein that has similar functions as the original protein. Tables of conservative substitutions presenting functionally similar amino acids are well known in the art. Examples of amino acid side chain characteristics that functionally resemble include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also encompassed in peptides of the present invention. However, peptides of the present invention are not restricted thereto and can include non-conservative modifications, so long as the modified peptide retains the CTL-inducing ability of the original peptide. Furthermore, modified peptides do not exclude CTL inducible peptides derived from polymorphic variants, interspecies homologues, and alleles of SARS-CoV-2 proteins.

So long as a peptide retains the CTL-inducing ability of an original peptide, one can modify (i.e., substitute, delete, insert and/or add) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably 15% or less, even more preferably 10% or less or 1 to 5%.

When used in the context of immunotherapy, peptides of the present invention should be presented on the surface of a cell or exosome, preferably as a complex with an HLA antigen. Therefore, it is preferable that the peptides of the present invention possess high binding affinity to the HLA antigen. To that end, the peptides can be modified by substitution, deletion, insertion, and/or addition of the amino acid residues to yield a modified peptide having improved binding affinity. Since the regularity of the sequences of peptides displayed by binding to HLA antigens is already known (Falk, et al., Immunogenetics 1994 40 232-41; Chujoh, et al., Tissue Antigens 1998: 52: 501-9; Takiguchi, et al., Tissue Antigens 2000: 55: 296-302), modifications based on such regularity can be introduced into the peptides of the present invention.

For example, in peptides having binding affinity for HLA Class I, the second amino acid from the N terminus and the C-terminal amino acid are generally anchor residues involved in the binding to HLA Class I (Rammensee H G, et al., Immunogenetics. 1995; 41(4): 178-228).

For example, peptides having high HLA-A24-binding affinity tend to have the second amino acid from the N terminus substituted with phenylalanine, tyrosine, methionine, or tryptophan. Similarly, peptides in which the C-terminal amino acid has been substituted with phenylalanine, leucine, isoleucine, tryptophan, or methionine tend to have high HLA-A24-binding affinity. Thus, in order to enhance HLA-A24-binding affinity, it may be desirable to substitute the second amino acid from the N terminus with phenylalanine, tyrosine, methionine, or tryptophan and/or to substitute the C-terminal amino acid with phenylalanine, leucine, isoleucine, tryptophan, or methionine. Accordingly, the present invention encompasses peptides having an amino acid sequence selected from those of SEQ ID NOs: 1, 2, 3, 4, 5, 7, 9, 10, 11, 12, 13, and 15 in which the second amino acid from the N terminus has been substituted with phenylalanine, tyrosine, methionine or tryptophan and/or the C terminus has been substituted with phenylalanine, leucine, isoleucine, tryptophan, or methionine.

Similarly, the present invention encompasses peptides comprising an amino acid sequence in which one, two, or several amino acids are substituted, deleted, inserted, and/or added in the sequences of SEQ ID NOs: 1, 2, 3, 4, 5, 7, 9, 10, 11, 12, 13, and 15, which peptides have one or both of the features: (a) the second amino acid from the N terminus is phenylalanine, tyrosine, methionine or tryptophan; and (b) the C-terminal amino acid is phenylalanine, leucine, isoleucine, tryptophan or methionine. In a preferred embodiment, the peptides of the present invention comprise an amino acid sequence comprising one or both of the substitution of the second amino acid from the N terminus with phenylalanine, tyrosine, methionine or tryptophan; and the substitution of the C-terminal amino acid with phenylalanine, leucine, isoleucine, tryptophan or methionine, in the amino acid sequences of SEQ ID NOs: 1, 2, 3, 4, 5, 7, 9, 10, 11, 12, 13 and 15.

Likewise, peptides having high HLA-A02-binding affinity tend to have the second amino acid from the N terminus substituted with leucine or methionine and/or the C-terminal amino acid substituted with valine or leucine. Thus, in order to enhance HLA-A02-binding affinity, it may be desirable to substitute the second amino acid from the N terminus with leucine or methionine and/or to substitute the C-terminal amino acid with valine or leucine. Accordingly, the present invention encompasses peptides having an amino acid sequence selected from those of SEQ ID NOs: 1, 2, 4, 7, 10, 12 and 13 in which the second amino acid from the N terminus has been substituted with leucine or methionine and/or the C-terminus has been substituted with valine or leucine.

Similarly, the present invention encompasses peptides comprising an amino acid sequence in which one, two, or several amino acids are substituted, deleted, inserted, and/or added in the sequences of SEQ ID NOs: 1, 2, 4, 7, 10, 12 and 13, which peptides have one or both of the features: (a) the second amino acid from the N terminus is leucine or methionine; and (b) the C-terminal amino acid is valine or leucine. In a preferred embodiment, the peptides of the present invention comprise an amino acid sequence comprising one or both of the substitution of the second amino acid from the N terminus with leucine or methionine; and the substitution of the C-terminal amino acid with valine or leucine, in the amino acid sequences of SEQ ID NOs: 1, 2, 4, 7, 10, 12 and 13.

Substitution(s) may be introduced into amino acid(s) not only at the terminus/termini, but also at a position(s) of potential T cell receptor (TCR) recognition site(s) of the peptides. Several research studies have demonstrated that a peptide that has amino acid substitutions, such as CAP1, $p53_{(264-272)}$, Her-2/$neu_{(369-377)}$ or $gp100_{(209-217)}$, may have equal to or better activity than that of the original peptide (Zaremba et al. Cancer Res. 57, 4570-4577, 1997; T. K. Hoffmann et al. J Immunol. (2002) February 1, 168(3): 1338-47; S. O. Dionne et al. Cancer Immunol immunother. (2003) 52: 199-206; and S. O. Dionne et al. Cancer Immunology, Immunotherapy (2004) 53, 307-14).

The present invention also contemplates that one, two or several amino acids can be added to the N terminus and/or C terminus of the peptides of the present invention (for example, peptides consisting of the amino acid sequence selected from among SEQ ID NOs: 1, 2, 3, 4, 5, 7, 9, 10, 11, 12, 13 and 15). Such modified peptides that retain CTL-inducing ability are also included in the present invention. For example, when a peptide in which one, two or several amino acids are added to the N terminus and/or C terminus of a peptide consisting of the amino acid sequence of SEQ ID NO: 1, 2, 3, 4, 5, 7, 9, 10, 11, 12, 13 or 15 is contacted with an APC(s), it is incorporated into the APC(s) and processed to become a peptide consisting of the amino acid sequence of SEQ ID NO: 1, 2, 3, 4, 5, 7, 9, 10, 11, 12, 13 or 15. It can then induce CTLs through presentation on the cell surface of an APC via the antigen presentation pathway.

However, when the amino acid sequence of a peptide is identical to a portion of the amino acid sequence of an endogenous or exogenous protein having a different function, side effects such as autoimmune disorders and/or allergic symptoms against specific substances may be induced. Therefore, it is preferable to perform homology searches using available databases to avoid situations in which the amino acid sequence of the peptide matches the amino acid sequence of another protein. When it becomes clear from the homology searches that no peptide exists with as few as 1 or 2 amino acid differences as compared to the objective peptide, the objective peptide can be modified in order to increase its binding affinity with HLA antigens, and/or increase its CTL-inducing ability without danger of such side effects.

Peptides in which one, two or several amino acids of a peptide of the present invention are modified are predicted to be able to retain CTL-inducing ability of the original peptide; however, it is preferable to verify the CTL-inducing ability of the modified peptides. Herein, the "peptide having CTL-inducing ability (CTL inducibility)" refers to a peptide that induces CTLs through APCs stimulated with the peptide. "CTL induction" includes induction of differentiation into CTLs, induction of CTL activation, induction of CTL proliferation, induction of CTL's cytotoxic activity, induction of CTL-mediated dissolution of target cells, and induction of increase of IFN-gamma production of CTLs.

The CTL-inducing ability can be confirmed by inducing and stimulating APCs that retain an HLA antigen (for example, B lymphocytes, macrophages, and dendritic cells) with a peptide, and mixing it with CD8-positive T cells; and then measuring IFN-gamma released by CTLs against the target cells. For the APCs, human peripheral blood mononuclear leukocyte-derived dendritic cells can be preferably used. As a reaction system, transgenic animals generated to express an HLA antigen can be used. Alternatively, for example, the target cells may be radio-labelled with $^{51}Cr$ or such, and the cytotoxic activity of the peptide-induced CTLs may be calculated from the radioactivity emitted from the target cells. Alternatively, in the presence of peptide-stimulated APCs, it is possible to evaluate the CTL-inducing ability by measuring the IFN-gamma produced and released by CTLs, and visualizing the inhibition zone on the media using anti-IFN-gamma monoclonal antibodies.

In addition to the modifications above, the peptides of the present invention can be linked to other peptides as long as the resultant linked peptide retains the CTL-inducing ability. An example of an appropriate peptide to be linked with the peptides of the present invention includes other CTL-inducing peptide derived from coronavirus proteins. Further, the peptides of the present invention can also be linked with each other. Suitable linkers for use in linking peptides are known in the art, and for example, linkers such as AAY (P. M. Daftarian et al., J Trans Med 2007, 5:26), AAA, NKRK (SEQ ID NO: 27) (R. P. M. Sutmuller et al., J Immunol. 2000, 165: 7308-15), or K (S. Ota et al., Can Res. 62, 1471-6, K. S. Kawamura et al., J Immunol. 2002, 168: 5709-15) can be used. Peptides can be linked in various arrangements (for example, catenulate, repeated, etc.), and one can also link three or more peptides.

The peptides of the present invention can also be linked to other substances as long as the resultant linked peptide retains the CTL-inducing ability. Examples of an appropriate substance to be linked with a peptide of the present invention include, for example, a peptide, a lipid, a sugar or sugar chain, an acetyl group, and a naturally-occurring or synthetic polymer. The peptides of the present invention can be modified by glycosylation, side-chain oxidation, phosphorylation or such, as long as their CTL-inducing ability is not impaired. One can also perform such types of modifications to confer additional functions (for example, targeting function and delivery function) or to stabilize the peptide.

For example, to increase the in vivo stability of a peptide, it is known in the art to introduce D-amino acids, amino acid mimetics or non-naturally occurring amino acids, and this concept may also be applied to peptides of the present invention. Peptide stability can be assayed by several methods. For example, stability can be tested by using a peptidase as well as various biological media such as human plasma and serum (see, e.g., Verhoef et al., Eur J Drug Metab Pharmacokin 1986, 11: 291-302).

Further, as stated above, among the modified peptides in which one, two, or several amino acid residues have been substituted, deleted, inserted and/or added, those having the same or higher activity as compared to original peptides can be screened for or selected. Thus, the present invention also provides methods of screening for or selecting modified peptides that have the same or higher activity than that of the original peptide. Specifically, the present invention provides a method of screening for a peptide having CTL-inducing ability, wherein the method comprises the steps of:

(a) generating candidate sequences consisting of an amino acid sequence in which one, two, or several amino acid residues are substituted, deleted, inserted and/or added to the original amino acid sequence consisting of the amino acid sequence selected from among SEQ ID NOs: 1, 2, 3, 4, 5, 7, 9, 10, 11, 12, 13 and 15;
(b) selecting from among the candidate sequences generated in (a), a candidate sequence that does not have a significant homology (sequence identity) with any known human gene product;
(c) contacting a peptide consisting of the candidate sequence selected in (b) with APCs;
(d) contacting the APCs of (c) with CD8-positive T cells; and
(e) selecting a peptide that has an equal to or higher CTL-inducing ability than that of a peptide consisting of the original amino acid sequence.

In an embodiment, APCs to be contacted with a peptide are APCs positive for either one of HLA-A02 or HLA-A24, or for both.

Herein, the peptide of the present invention is also described as a "SARS-CoV-2 peptide(s)" or a "SARS-CoV-2 polypeptide(s)".

In a certain embodiment of the present invention, a portion of TCR can also comprise one, two, or three complementarity determining regions (CDRs) of one or both of the α and β chains of the TCR. In a preferred embodiment, the portion of TCR comprises CDR3 of one or both of the α and β chains of the TCR. The amino acid sequences of the preferred CDR3 identified in the present invention are as follows:

CDR3 of a human T cell receptor α chain specified by any one of the amino acid sequences selected from the group consisting of SEQ ID NOs: 32, 34, 36, 38 and 40; and CDR3 of a human T cell receptor β chain specified by any one of the amino acid sequences selected from the group consisting of SEQ ID NOs: 33, 35, 37, 39 and 41.

In a certain embodiment of the present invention, the amino acid sequences of CDR3 of T cell receptor α and β chains can be combined, for example, as follows:

CDR3 of T cell receptor α chain CDR3 of T cell receptor 3 chain

SEQ ID NO: 32 SEQ ID NO: 33;

SEQ ID NO: 34 SEQ ID NO: 35;

SEQ ID NO: 36 SEQ ID NO: 37;

SEQ ID NO: 38 SEQ ID NO: 39; and

SEQ ID NO: 40 SEQ ID NO: 41.

Furthermore, CDR3s comprising conservative modifications are also included in the CDR3s in the present invention. However, the peptides of the present invention are not limited thereto, and may comprise non-conservative modifications as long as the modified CDR3 retains the function of the original CDR3.

In the present invention, when the same antigen recognition specificity as that of the TCR from which the original CDR3 is derived is conferred on a TCR to which a modified CDR3 is transplanted, it means that the original function of the CDR3 is retained in the modified CDR3. Such specific recognition can be confirmed by any known method, and preferred methods include, for example, tetramer assays using peptides administered to a subject who has acquired HLA molecules and TCRs (e.g., Altman et al. Science. 1996, 274, 94-6; McMichael et al. J Exp Med. 1998, 187, 1367-71) and ELISPOT assays. It can be confirmed by performing an ELISPOT assay that T cells expressing TCRs on their cell surface recognize cells by the TCRs, and that signals are transduced intracellularly and then cytokines such as IFN-γ are released from the T cells. Cytotoxic activity of T cells against target cells can be examined using methods well known in the art. Preferred methods include, for example, a chromium release assay using coronavirus-infected HLA-positive cells as a target cell.

III. Preparation of Peptides of the Present Invention

Well known techniques can be used to prepare peptides of the present invention. For example, recombinant DNA technology or chemical synthesis can be used to prepare peptides of the present invention. Peptides of the present invention can be synthesized individually, or as longer polypeptides including two or more peptides. Peptides of the present invention can be isolated from host cells or synthesis reaction products after they are produced in the host cells using recombinant DNA technology or after they are chemically synthesized. That is, peptides of the present invention can be purified or isolated so as not to substantially contain other host-cell proteins and fragments thereof, or any other chemical substances.

The peptides of the present invention may contain modifications, such as glycosylation, side chain oxidation, or phosphorylation provided such modifications do not destroy the biological activity of the original peptide. Other illustrative modifications include incorporation of D-amino acids or other amino acid mimetics that may be used, for example, to increase the serum half life of the peptides.

A peptide of the present invention can be obtained through chemical synthesis based on the selected amino acid sequence. Examples of conventional peptide synthesis methods that can be adapted to the synthesis include the methods described in the documents below:

(i) Peptide Synthesis, Interscience, New York, 1966;

(ii) The Proteins, Vol. 2, Academic Press, New York, 1976;

(iii) "Peptide Synthesis" (in Japanese), Maruzen Co., 1975;

(iv) "Basics and Experiment of Peptide Synthesis" (in Japanese), Maruzen Co., 1985;

(v) "Development of Pharmaceuticals" (in Japanese), Continued Vol. 14 (peptide synthesis), Hirokawa, 1991;

(vi) WO99/67288; and (vii) Barany G. & Merrifield R. B., Peptides Vol. 2, Solid Phase Peptide Synthesis, Academic Press, New York, 1980, 100-18.

Alternatively, the peptides of the present invention can be obtained adapting any known genetic engineering methods for producing peptides (e.g., Morrison J, J Bacteriology 1977, 132: 349-51; Clark-Curtiss & Curtiss, Methods in Enzymology (Wu et al.) 1983, 101: 347-62). For example, first, a suitable vector harboring a polynucleotide encoding the peptide of the present invention in an expressible form (e.g., downstream of a regulatory sequence corresponding to a promoter sequence) is prepared and transformed into a suitable host cell. The host cell is then cultured to produce the peptide of the present invention. The peptide of the present invention can also be produced in vitro using an in vitro translation system.

IV. Polynucleotides

The present invention also provides a polynucleotide which encodes any of the peptides of the present invention. These include polynucleotides derived from the naturally occurring SARS-CoV-2 gene (e.g., GenBank Accession No. MN908947 (SEQ ID NO: 16)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described above without altering the encoded polypeptide. Such nucleic acid variations are "silent variations", which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C and G, and T is replaced by U in an RNA.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (e.g., plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5.

V. Exosomes

The present invention further provides intracellular vesicles, referred to as exosomes, that present complexes formed between the peptides of the present invention and HLA antigens on their surface. Exosomes can be prepared, for example, using the methods detailed in JPH11-510507 and WO99/03499, and can be prepared using APCs obtained from patients who are subject to treatment and/or prevention (prophylaxis). The exosomes of the present invention can be inoculated as vaccines, in a fashion similar to the peptides of the present invention.

The type of the HLA antigens included in the above-described complexes must match that of the subject in need of treatment and/or prevention (prophylaxis). For example, HLA-A24 (for example, HLA-A*24:02) is an allele widely and generally seen in Asian countries including Japan, and HLA-A02 (for example, HLA-A*02:01) is an allele widely and generally seen in Europe and the United States. These HLA antigen types are considered to be suitable for treatment in Asian or Caucasian patients. Typically in clinic, it is possible to select an appropriate peptide that has a high level of binding affinity for a specific HLA antigen or that has CTL-inducing ability by antigen presentation mediated by a specific HLA antigen, by studying in advance the HLA antigen type of the patient in need of treatment.

The exosomes of the present invention present on their surface a complex of a peptide of the present invention and HLA-A24 or HLA-A02. When the HLA that forms a complex with a peptide of the present invention is HLA-A24, the peptide of the present invention is preferably a peptide having the amino acid sequence selected from among SEQ ID NOs: 1, 2, 3, 4, 5, 7, 9, 10, 11, 12, 13 and 15 or a modified peptide thereof, and more preferably a peptide consisting of the amino acid sequence selected from among SEQ ID NOs: 1, 2, 3, 4, 5, 7, 9, 10, 11, 12, 13 and or a modified peptide thereof.

When the HLA that forms a complex with a peptide of the present invention is HLA-A02, the peptide of the present invention is preferably a peptide having the amino acid sequence selected from among SEQ ID NOs: 1, 2, 4, 7, 10, 12 and 13 or a modified peptide thereof, and more preferably a peptide consisting of the amino acid sequence selected from among SEQ ID NOs: 1, 2, 4, 7, 10, 12 and 13 or a modified peptide thereof.

VI. Antigen-Presenting Cells (APCs)

The present invention further provides APCs that present on their surface complexes formed between HLA antigens and peptides of the present invention. Alternatively, the present invention provides APCs having on their cell surface complexes formed between HLA antigens and peptides of the present invention. The APCs of the present invention can be isolated APCs. When used in the context of cells (APCs, CTLs, etc.), the term "isolated" means that the cells are separated from another type of cells. The APCs of the present invention may be APCs induced from APCs derived from the patient to be subjected to treatment and/or prevention (prophylaxis), and can be administered as a vaccine by themselves or in combination with other drugs including a peptide(s), an exosome(s) or a CTL(s) of the present invention.

The APCs of the present invention are not limited to specific types of cells, and include cells known to present proteinaceous antigens on their cell surface so as to be recognized by lymphocytes, for example, dendritic cells (DCs), Langerhans cells, macrophages, B cells, and activated T cells. Since DC is a representative APC that has the strongest CTL-inducing activity among APCs, DCs can be preferably used as the APCs of the present invention.

For example, APCs of the present invention can be obtained by inducing DCs from peripheral blood monocytes and then stimulating them in vitro, ex vivo, or in vivo with the peptides of the present invention. When the peptide of the present invention is administered to a subject, APCs presenting the peptide of the present invention are induced in the body of the subject. Therefore, after the peptides of the present invention are administered to a subject, the APCs of the present invention can be obtained by collecting APCs from the subject. Alternatively, the APCs of the present invention can be obtained by contacting APCs collected from a subject with a peptide of the present invention.

In order to induce an immune response against coronavirus-infected cells in a subject, the APCs of the present invention can be administered to the subject by themselves or in combination with other drugs including peptide(s), exosome(s) or CTL(s) of the present invention. For example, the ex vivo administration can comprise the following steps of:

(a) collecting APCs from a first subject;

(b) contacting the APCs of step (a) with a peptide; and (c) administering the APCs of step (b) to a second subject.

The first subject and the second subject may be the same individual, or may be different individuals. When the first subject and the second subject are different individuals, it is preferable that the HLAs of the first subject and the second subject are of the same type. The APC obtained in step (b) above can be a vaccine for treatment and/or prevention (prophylaxis) of coronavirus infectious disease. In a certain embodiment, the methods of the present invention may further additionally comprise the step of collecting the APCs after step (b).

The APCs of the present invention obtained by a method such as described above have CTL-inducing ability. The term "CTL-inducing ability (CTL inducibility)" used in the context of an APC(s) refers to the ability of the APC to be able to induce a CTL(s) when placed in contact with a CD8-positive T cell(s). The CTL(s) induced by the APC of the present invention is a CTL(s) specific to SARS-CoV-2 protein and demonstrates a specific cytotoxic activity against SARS-CoV-2 infected cells.

In addition to the above-described methods, the APCs of the present invention can be prepared by introducing a polynucleotide encoding a peptide of the present invention into APCs in vitro. The polynucleotide to be introduced can be in the form of DNA or RNA. The method of introduction is not particularly limited, and examples thereof include various methods conventionally performed in the art such as lipofection, electroporation and the calcium phosphate method. More specifically, methods described in Cancer Res 1996, 56: 5672-7; J Immunol 1998, 161: 5607-13; J Exp Med 1996, 184: 465-72, and JP2000-509281 can be used. By introducing a polynucleotide encoding a peptide of the present invention into an APC, the polynucleotide is transcribed and translated in the cell, and then the produced peptide is processed by MHC Class I and proceeds through a presentation pathway to present the peptide of the present invention on the cell surface of the APC.

In a preferred embodiment, the APC of the present invention is an APC that presents on its cell surface a complex formed between a peptide of the present invention and HLA-A24 (more preferably HLA-A*24:02). When the HLA that forms a complex with a peptide of the present invention is HLA-A24, the peptide of the present invention is preferably a peptide having the amino acid sequence selected from among SEQ ID NOs: 1, 2, 3, 4, 5, 7, 9, 10, 11, 12, 13 and or a modified peptide thereof, and more preferably a peptide consisting of the amino acid sequence selected from among SEQ ID NOs: 1, 2, 3, 4, 5, 7, 9, 10, 11, 12, 13 and 15.

Alternatively, in a preferred embodiment, the APC of the present invention is an APC that presents on its cell surface a complex formed between a peptide of the present invention and HLA-A02 (more preferably HLA-A*02:01). When the HLA that forms a complex with a peptide of the present invention is HLA-A02, the peptide of the present invention is preferably a peptide having the amino acid sequence selected from among SEQ ID NOs: 1, 2, 4, 7, 10, 12 and 13 or a modified peptide thereof, and more preferably a peptide consisting of the amino acid sequence selected from among SEQ ID NOs: 1, 2, 4, 7, 10, 12 and 13.

The APC(s) of the present invention is preferably an APC(s) induced by a method comprising a step described (a) or (b) below:

(a) contacting an APC(s) expressing HLA-A24 (more preferably HLA-A*24:02) or HLA-A02 (more preferably HLA-A*02:01) with a peptide of the present invention; or (b) introducing a polynucleotide encoding a peptide of the present invention into an APC(s) expressing HLA-A24 (more preferably HLA-A*24:02) or HLA-A02 (more preferably HLA-A*02:01).

The peptide of the present invention to be contacted with the HLA-A24-expressing APC(s) is preferably a peptide having the amino acid sequence selected from among SEQ ID NOs: 1, 2, 3, 4, 5, 7, 9, 10, 11, 12, 13 and 15 or a modified peptide thereof, and more preferably a peptide consisting of the amino acid sequence selected from among SEQ ID NOs: 1, 2, 3, 4, 5, 7, 9, 10, 11, 12, 13 and 15. The peptide of the present invention to be contacted with the HLA-A02-expressing APC(s) is preferably a peptide having the amino acid sequence selected from among SEQ ID NOs: 1, 2, 4, 7, 10, 12 and 13 or a modified peptide thereof, and more preferably a peptide consisting of the amino acid sequence selected from among SEQ ID NOs: 1, 2, 4, 7, 10, 12 and 13.

The present invention provides use of a peptide of the present invention for the manufacture of a pharmaceutical composition that induces an APC(s) having CTL-inducing ability. In addition, the present invention provides a method or process of manufacturing a pharmaceutical composition that induces an APC(s) having CTL-inducing ability. Further, the present invention provides a peptide of the present invention for inducing an APC(s) having CTL-inducing ability.

VII. Cytotoxic T Lymphocytes (CTLs)

The CTL induced by a peptide of the present invention can be used as a vaccine in a similar manner to the peptide of the present invention for enhancing an immune response targeting coronavirus-infected cell in vivo. Thus, the present invention provides CTLs that are induced or activated by a peptide of the present invention. The CTLs of the present invention are CTLs that target a peptide of the present invention, and are capable of binding to a complex of a peptide of the present invention and an HLA antigen. Binding of a CTL to the complex is mediated via a T cell receptor (TCR) present on the cell surface of the CTL. The CTLs of the present invention can be isolated CTLs.

The CTLs of the present invention can be obtained by (1) administering a peptide of the present invention to a subject, (2) stimulating APCs and CD8-positive T cells, or peripheral blood mononuclear cells (PBMCs) derived from a subject with a peptide of the present invention in vitro, (3) contacting in vitro CD8-positive T cells or PBMCs with APCs or exosomes that present on their surface a complex of an HLA antigen and a peptide of the present invention, or (4) introducing into CD8-positive T cells a vector comprising a polynucleotide encoding each subunit of a T cell receptor (TCR) capable of binding to a peptide of the present invention presented on cell surface via an HLA antigen. The exosomes and APCs used in the method of (2) or (3) above can be prepared by methods described in the "V. Exosomes" and "VI. Antigen-presenting cells (APCs)" sections, respectively, and the details of the method of (4) above will be described in the "VIII. T cell receptor (TCR)" section. In a certain embodiment, the methods of the present invention may further additionally comprise the step of collecting induced CTLs after each step.

The CTLs of the present invention can be administered by themselves to patients who are subject to treatment and/or prevention (prophylaxis), or in combination with other drugs including peptide(s), APC(s) or exosome(s) of the present invention for the purpose of regulating effects. Further, the CTLs of the present invention can be CTLs induced from CD8-positive T cells derived from the patients who are subject to administration of the CTLs. The CTLs of the present invention act specifically on target cells that present the peptides of the present invention, for example, the same peptides used to induce the CTLs of the present invention. The target cells may be cells that endogenously express SARS-CoV-2 protein, such as coronavirus-infected cells, or cells transfected with the SARS-CoV-2 gene. Cells that present a peptide of the present invention on their cell surface due to stimulation by the peptide can become a target of attack by the CTLs of the present invention. The cells targeted by the CTLs of the present invention are preferably cells that are positive for HLA-A24 (more preferably HLA-A*24:02) or HLA-A02 (more preferably HLA-A*02:01).

In a preferred embodiment, the CTLs of the present invention target specifically cells that express both SARS-CoV-2 protein and HLA-A24 (more preferably HLA-A*24:02) or HLA-A02 (more preferably HLA-A*02:01). Herein, that the CTL "targets" cells refers to CTL recognition of cells that present on their cell surface a complex of HLA and a peptide of the present invention and demonstration of a cytotoxic activity against the cells. Further, "specifically target" refers to that the CTLs demonstrate a cytotoxic activity against those cells, but do not show a damaging activity to other cells. The expression "recognize cells" used in the context of CTLs refers to binding to a complex of HLA and a peptide of the present invention presented on cell surface via its TCR, and demonstrating a specific cytotoxic activity against the cell. Therefore, the CTLs of the present invention are preferably CTLs that can bind via TCR to a complex formed between a peptide of the present invention and HLA-A24 (more preferably HLA-A*24:02) or HLA-A02 (more preferably HLA-A*02:01) presented on cell surface.

Furthermore, the CTLs of the present invention are preferably CTLs induced by a method comprising a step described in (a) or (b) below:

(a) contacting in vitro CD8-positive T cells with APCs or exosomes that present on their surface a complex of a peptide of the present invention and HLA-A24 (more preferably HLA-A*24:02) or HLA-A02 (more preferably HLA-A*02:01); or (b) introducing into CD8-positive T cells a polynucleotide encoding each subunit of a TCR capable of binding to a peptide of the present invention presented on cell surface by HLA-A24 (more preferably HLA-A*24:02) or HLA-A02 (more preferably HLA-A*02:01).

VIII. T Cell Receptors (TCRs)

The present invention also provides compositions comprising a polynucleotide encoding each subunit of a TCR capable of binding to a peptide of the present invention presented on cell surface by an HLA antigen, and methods of using the same. The polynucleotide confers CD8-positive T cells with specificity against coronavirus-infected cells through expression of a TCR capable of binding to a peptide of the present invention presented on cell surface by an HLA antigen. Polynucleotides encoding an alpha chain(s) and a beta chain(s) can be identified as the TCR subunit of the CTL induced by a peptide of the present invention by using known methods in the art (WO2007/032255 and Morgan et al., J Immunol, 171, 3288 (2003)). For example, PCR methods are preferred for TCR analysis. Without being limited thereto, PCR primers for analysis may be, for example, 5'-R Primer (5'-gtctaccaggcattcgcttcat-3') (SEQ ID NO: 28) as a 5' side primer; and 3-TRa-C Primer (5'-tcagctggaccacagccgcagcgt-3') (SEQ ID NO: 29) specific to TCR-alpha-chain C-region, 3-TRb-C1 Primer (5'-tcagaaatcctttctcttgac-3') (SEQ ID NO: 30) specific to TCR-beta-chain C1-region or 3-TR-beta-C2 Primer (5'-ctagcctctggaatcctttctctt-3') (SEQ ID NO: 31) specific to TCR-beta-chain C2-region as 3' side primers. The TCRs formed by introducing the identified polynucleotides into CD8-positive T cells can bind with high binding affinity to the target cells that present a peptide of the present invention, and mediates efficient killing of the target cells presenting a peptide of the present invention in vivo and in vitro.

A polynucleotide encoding each TCR subunit can be incorporated into an appropriate vector, for example, retrovirus vector. These vectors are well known in the art. The polynucleotide or a vector comprising thereof in an expressible form can be introduced into a CD8-positive T cell, for example, a CD8-positive T cell derived from a patient. The present invention provides off-the-shelf compositions that allow rapid and easy production of modified T cells that have superior coronavirus-infected cell-killing properties by rapid modification of the patient's own T cells (or T cells derived from another subject).

Herein, a specific TCR is a TCR that can confer a specific cytotoxic activity against target cells by specifically recognizing a complex of a peptide of the present invention and an HLA antigen presented on the surface of the target cell when the TCR is present on the surface of a CD8-positive T cell. Specific recognition of the above-described complex can be confirmed by any known method, and preferable examples thereof include HLA multimer staining analysis using HLA molecules and peptides of the present invention and ELISPOT assay methods. Specific TCR-mediated recognition of target cell by T cell introduced with the above-described polynucleotide and signal transduction in the cell can be confirmed by carrying out an ELISPOT assay. When the above-described TCR is present on the surface of a CD8-positive T cell, whether the TCR can confer a target cell-specific cytotoxic activity against the CD8-positive T cell can also be confirmed by known methods. Preferable methods include, for example, measuring the cytotoxic activity against target cells by a chrome release assay method or such.

The present invention provides, in the context of HLA-A24, CTLs prepared by transforming CD8-positive T cells with a polynucleotide encoding each subunit of TCR that binds to, for example, a peptide having the amino acid sequence selected from among SEQ ID NOs: 1, 2, 3, 4, 5, 7, 9, 10, 11, 12, 13 and 15. The present invention provides, in the context of HLA-A02, CTLs prepared by transforming CD8-positive T cells with a polynucleotide encoding each subunit of TCR that binds to, for example, a peptide having the amino acid sequence selected from among SEQ ID NOs: 1, 2, 4, 7, 10, 12 and 13.

The transformed CTLs are capable of homing in vivo and may be propagated by a well-known in vitro culturing method (for example, Kawakami et al., J Immunol., 142, 3452-61 (1989)). The CTLs of the present invention can be used to form an immunogenic composition useful for disease treatment or prevention (prophylaxis) in a patient in need of treatment or prevention (prophylaxis) (the contents are incorporated herein for reference WO2006/031221).

The present invention relates to TCRs expressed by T cells that recognize a SARS-CoV-2-derived peptide. TCR is a protein molecule consisting of a dimer of an $\alpha$ chain and a $\beta$ chain. Human T cells recognize peptides presented on MHC class I (also known as human leukocyte antigen, HLA) molecules through TCRs. As a result, T cell proliferation, differentiation, cytokine production, cytotoxic substance (perform and granzymes) secretion and the like are induced.

The TCR-$\alpha$ gene comprises V$\alpha$, J$\alpha$ and C$\alpha$ genes. The TCR-$\beta$ gene comprises V$\beta$, D$\beta$, J$\beta$ and C$\beta$ genes. The regions determining the specificity of TCR for a peptide are called complementarity determining regions (CDRs), which include CDR1, CDR2 and CDR3. Of these, CDR3 contacts a peptide directly, and therefore its amino acid sequence is very important in determining the antigen recognition specificity of TCR. In the TCR-α chain, V-J corresponds to CDR3, and in the TCR-β chain, V-D and D-J correspond to CDR3. Insertion and deletion of nucleotides generate their diversity.

Alternatively, in a certain embodiment of the present invention, a portion of TCR can also comprise one, two, or three complementarity determining regions (CDRs) of one or both of the α and β chains of the TCR. In a preferred embodiment, the portion of TCR comprises CDR3 of one or both of the α and β chains of the TCR. The amino acid sequences of the preferred CDR3 identified in the present invention are as follows:

CDR3 of a human T cell receptor α chain specified by any one of the amino acid sequences selected from the group consisting of SEQ ID NOs: 32, 34, 36, 38 and 40; and CDR3 of a human T cell receptor β chain specified by any one of the amino acid sequences selected from the group consisting of SEQ ID NOs: 33, 35, 37, 39 and 41.

In a certain embodiment of the present invention, the amino acid sequences of CDR3 of T cell receptor α and β chains can be combined, for example, as follows:

CDR3 of T cell receptor α chain CDR3 of T cell receptor β chain

SEQ ID NO: 32 SEQ ID NO: 33;
SEQ ID NO: 34 SEQ ID NO: 35;
SEQ ID NO: 36 SEQ ID NO: 37;
SEQ ID NO: 38 SEQ ID NO: 39; and
SEQ ID NO: 40 SEQ ID NO: 41.

In a certain embodiment, α chain and β chain of TCR, TCR consisting of them, polynucleotides encoding them of the present invention may be isolated ones.

IX. Pharmaceutical Compositions

The present invention further provides compositions or pharmaceutical compositions, comprising at least one active ingredient selected from below:

(a) a peptide of the present invention;
(b) a polynucleotide encoding a peptide of the present invention in an expressible form;
(c) an APC of the present invention;
(d) an exosome of the present invention; and
(e) a CTL of the present invention.

The pharmaceutical compositions of the present invention can comprise as needed a carrier(s), an excipient(s) or such commonly used in pharmaceuticals without particular limitations, in addition to the active ingredient(s) described above. An example of a carrier that can be used in a pharmaceutical composition of the present invention includes sterilized water, physiological saline, phosphate buffer, culture fluid and such. Therefore, the present invention also provides pharmaceutical compositions, comprising at least one active ingredient selected from (a) to (e) below and a pharmaceutically acceptable carrier:

(a) a peptide of the present invention;
(b) a polynucleotide encoding a peptide of the present invention in an expressible form;
(c) an APC of the present invention;
(d) an exosome of the present invention; and
(e) a CTL of the present invention.

Further, the pharmaceutical compositions of the present invention can comprise, as needed, stabilizers, suspensions, preservatives, surfactants, solubilizing agents, pH adjusters, aggregation inhibitors and such.

The SARS-CoV-2 protein expression significantly upregulates in coronavirus-infected cells compared with coronavirus non-infected cells. Thus, a peptide of the present invention or a polynucleotide encoding the peptide can be used to any one of purposes selected from treatment, prevention (prophylaxis), and suppression of aggravation of coronavirus infectious disease, and combinations thereof. Therefore, the present invention provides pharmaceutical compositions for any one of purposes selected from treatment, prevention (prophylaxis), and suppression of aggravation of coronavirus infectious disease, or plurality of purposes, the pharmaceutical composition comprising one or more types of peptides or polynucleotides of the present invention as an active ingredient. Alternatively, the peptides of the present invention can be made to be presented on the surface of exosomes or APCs for use as pharmaceutical compositions. In addition, CTLs of the present invention targeting any one of the peptides of the present invention can also be used as an active ingredient of the pharmaceutical compositions of the present invention. The pharmaceutical compositions of the present invention may comprise a therapeutically effective amount or a pharmaceutically effective amount of the above-described active ingredient.

The pharmaceutical compositions of the present invention may also be used as a vaccine. In the context of the present invention, the term "vaccine" (also called "immunogenic composition") refers to a composition that has a function of inducing an immune response that leads to anti-infective action against coronavirus when inoculated into an animal. Thus, a pharmaceutical composition of the present invention can be used to induce an immune response that leads to anti-invective action against coronavirus. The immune response induced by a peptide, a polynucleotide, an APC, a CTL and a pharmaceutical composition of the present invention is not particularly limited as long as it is an immune response that leads to anti-infective action against coronavirus, and examples include induction of coronavirus-infected cell-specific CTLs and induction of coronavirus-infected cell-specific cytotoxic activity.

The pharmaceutical compositions of the present invention can be used for any one of treatment, prevention (prophylaxis), and suppression of aggravation of coronavirus infectious diseases, or combination thereof in human subjects or patients. The pharmaceutical compositions of the present invention can be used preferably to a subject positive for HLA-A24 or HLA-A02. Further, the pharmaceutical compositions of the present invention can be used preferably to treat and/or prevent coronavirus infectious diseases, and/or suppress aggravation in a subject having HLA-A24 or HLA-A02.

In another embodiment, the present invention provides use of an active ingredient selected from below in the manufacture of a pharmaceutical composition for either or both of treating and preventing coronavirus infectious disease:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

Alternatively, the present invention further provides an active ingredient selected from below for use in either or both of treating and preventing coronavirus infectious disease:

(a) a peptide of the present invention;

(b) a polynucleotide encoding a peptide of the present invention in an expressible form;

(c) an APC that presents a peptide of the present invention on its surface;

(d) an exosome that presents a peptide of the present invention on its surface; and (e) a CTL of the present invention.

Alternatively, the present invention further provides a method or process for manufacturing a pharmaceutical composition for either or both of treating and preventing coronavirus infectious disease, wherein the method or process comprises a step of formulating at least one active ingredient selected from below with a pharmaceutically or physiologically acceptable carrier:

(a) a peptide of the present invention;

(b) a polynucleotide encoding a peptide of the present invention in an expressible form;

(c) an APC that presents a peptide of the present invention on its surface;

(d) an exosome that presents a peptide of the present invention on its surface; and (e) a CTL of the present invention.

In another embodiment, the present invention further provides a method or process for manufacturing a pharmaceutical composition for either or both of treating and preventing coronavirus infectious disease, wherein the method or process comprises a step of mixing an active ingredient selected from below with a pharmaceutically or physiologically acceptable carrier:

(a) a peptide of the present invention;

(b) a polynucleotide encoding a peptide of the present invention in an expressible form;

(c) an APC that presents a peptide of the present invention on its surface;

(d) an exosome that presents a peptide of the present invention on its surface; and (e) a CTL of the present invention.

In another embodiment, the present invention further provides a method for either or both of treating and preventing coronavirus infectious disease, which comprises a step of administering to a subject at least one active ingredient selected from below:

(a) a peptide of the present invention;

(b) a polynucleotide encoding a peptide of the present invention in an expressible form;

(c) an APC that presents a peptide of the present invention on its surface;

(d) an exosome that presents a peptide of the present invention on its surface; and (e) a CTL of the present invention.

In the present invention, peptides having the amino acid sequence selected from among SEQ ID NOs: 1, 2, 3, 4, 5, 7, 9, 10, 11, 12, 13 and 15 are identified as HLA-A24-restricted epitope peptides that can induce a potent and specific immune response. Therefore, pharmaceutical compositions of the present invention comprising at least one peptide having the amino acid sequence selected from among SEQ ID NOs: 1, 2, 3, 4, 5, 7, 9, 10, 11, 12, 13 and 15 are suitable particularly for administration to a subject having HLA-A24 (for example, HLA-A*24:02) as an HLA antigen. The same applies to pharmaceutical compositions comprising a polynucleotide encoding any of these peptides (i.e., polynucleotides of the present invention), an APC or exosome that presents these peptides (i.e., APCs or exosomes of the present invention), or a CTL targeting these peptides (i.e., CTLs of the present invention). That is, pharmaceutical compositions comprising an active ingredient in association with a peptide having the amino acid sequence selected from among SEQ ID NOs: 1, 2, 3, 4, 5, 7, 9, 10, 11, 12, 13 and 15 are suitable for administration to subjects having HLA-A24 (i.e., HLA-A24-positive subjects). In a more preferred embodiment, the pharmaceutical composition of the present invention is a pharmaceutical composition that comprises a peptide having the amino acid sequence of SEQ ID NO: 1, 2, 4, 5, 7, 9, 10 or 13.

Similarly, in the present invention, peptides having the amino acid sequence selected from among SEQ ID NOs: 1, 2, 4, 7, 10, 12 and 13 are identified as HLA-A02-restricted epitope peptides that can induce a potent and specific immune response. Therefore, pharmaceutical compositions of the present invention comprising at least one peptide having the amino acid sequence selected from among SEQ ID NOs: 1, 2, 4, 7, 10, 12 and 13 are suitable particularly for administration to a subject having HLA-A02 (for example, HLA-A*02:01) as an HLA antigen. The same applies to pharmaceutical compositions comprising a polynucleotide encoding any of these peptides (i.e., polynucleotides of the present invention), an APC or exosome that presents these peptides (i.e., APCs or exosomes of the present invention), or a CTL targeting these peptides (i.e., CTLs of the present invention). That is, pharmaceutical compositions comprising an active ingredient in association with a peptide having the amino acid sequence selected from among SEQ ID NOs: 1, 2, 4, 7, 10, 12 and 13 are suitable for administration to subjects having HLA-A02 (i.e., HLA-A02-positive subjects). In a more preferred embodiment, the pharmaceutical composition of the present invention is a pharmaceutical composition that comprises a peptide having the amino acid sequence of SEQ ID NO: 1, 2, 10 or 13.

Coronavirus infectious diseases to be treated and/or prevented by pharmaceutical compositions of the present invention are not particularly limited as long as they are coronavirus infectious diseases, and coronaviruses include SARS-CoV-2, MERS-CoV, SARS-CoV, and such.

In addition to the active ingredients described above, the pharmaceutical compositions of the present invention can comprise the other peptides that have the ability to induce CTLs against coronavirus-infected cells (for example, the other coronavirus protein-derived CTL-inducing peptides), the other polynucleotides encoding the other peptides, the other cells that present the other peptides, or such.

The pharmaceutical compositions of the present invention may also optionally comprise the other therapeutic substances as an active ingredient, as long as they do not inhibit the anti-infective effects against coronavirus of the above-described active ingredients such as peptides of the present invention. For example, the pharmaceutical compositions of the present invention may optionally comprise anti-inflammatory compositions, analgesics, chemotherapeutics including antiviral agents, and the like. In addition to including the other therapeutic substances to a pharmaceutical composition of the present invention itself, one can also administer the pharmaceutical composition of the present invention sequentially or concurrently with one or more other pharmaceutical compositions. The dose of the pharmaceutical composition of the present invention and the other pharmaceutical compositions depend on, for example, the type of pharmaceutical composition used and the disease being treated, as well as the scheduling and routes of administration.

It should be understood that in consideration of the formulation type, the pharmaceutical composition of the present invention may include other components conventional in the art, in addition to the ingredients specifically mentioned herein.

The present invention also provides articles of manufacture or kits that comprise a pharmaceutical composition of the present invention. The articles of manufacture or kits of the present invention can include a container that houses the pharmaceutical composition of the present invention. An example of an appropriate container includes a bottle, a vial or a test tube, but is not limited thereto. The container may be formed of various materials such as glass or plastic. A label may be attached to the container, and the disease or disease state to which the pharmaceutical composition of the present invention should be used may be described in the label. The label may also indicate directions for administration and such.

The articles of manufacture or kits of the present invention may further comprise a second container that houses pharmaceutically acceptable diluents optionally, in addition to the container that houses the pharmaceutical composition of the present invention. The articles of manufacture or kits of the present invention may further comprise the other materials desirable from a commercial standpoint and the user's perspective, such as the other buffers, diluents, filters, injection needles, syringes, package inserts with instructions for use.

As needed, the pharmaceutical composition of the present invention can be provided in a pack or dispenser device that can contain one or more units of dosage forms containing active ingredients. The pack can include, for example, a metallic foil or a plastic foil such as a blister pack. Instructions for administration can be attached to the pack or dispenser device.

(1) Pharmaceutical Compositions Comprising Peptide(s) as an Active Ingredient

The pharmaceutical composition comprising a peptide of the present invention can be formulated by conventional formulation methods as needed. The pharmaceutical compositions of the present invention may comprise as needed in addition to the peptide of the present invention, carriers, excipients and such commonly used in pharmaceuticals without particular limitations. Examples of carriers that can be used in pharmaceutical compositions of the present invention include sterilized water (for example, water for injection), physiological saline, phosphate buffer, phosphate buffered saline, Tris buffered saline, 0.3% glycine, culture fluid, and such. Further, the pharmaceutical compositions of the present invention may comprise as needed stabilizers, suspensions, preservatives, surfactants, solubilizing agents, pH adjusters, aggregation inhibitors, and such. The pharmaceutical compositions of the present invention can induce specific immunity against coronavirus-infected cells, and thus can be applied for the purpose of treatment or prevention (prophylaxis) of coronavirus infectious diseases.

For example, the pharmaceutical compositions of the present invention can be prepared by dissolving in pharmaceutically or physiologically acceptable water-soluble carriers such as sterilized water (for example, water for injection), physiological saline, phosphate buffer, phosphate buffered saline, and Tris buffered saline and adding, as needed, stabilizers, suspensions, preservatives, surfactants, solubilizing agents, pH adjusters, aggregation inhibitors and such, and then sterilizing the peptide solution. The method of sterilizing a peptide solution is not particularly limited, and is preferably carried out by filtration sterilization. Filtration sterilization can be performed using, for example, a filtration sterilization filter of 0.22 micro-m or less in pore diameter. The filtration-sterilized peptide solution can be administered to a subject, for example, as an injection, without being limited thereto. The pharmaceutical compositions of the present invention may be prepared as a freeze-dried formulation by freeze-drying the above-described peptide solution. The freeze-dried formulation can be prepared by filling the peptide solution prepared as described above into an appropriate container such as an ampule, a vial or a plastic container, followed by freeze drying and encapsulation into the container with a wash-sterilized rubber plug or such after pressure recovery. The freeze-dried formulation can be administered to a subject after it is re-dissolved in pharmaceutically or physiologically acceptable water-soluble carriers such as sterilized water (for example, water for injection), physiological saline, phosphate buffer, phosphate buffered saline, Tris buffered saline and such before administration. Preferred examples of pharmaceutical compositions of the present invention include injections of such a filtration-sterilized peptide solution, and freeze-dried formulations that result from freeze-drying the peptide solution. The present invention further encompasses kits comprising such a freeze-dried formulation and re-dissolving solution. The present invention also encompasses kits comprising a container that houses the freeze-dried formulation, which is a pharmaceutical composition of the present invention, and a container that houses a re-dissolving solution thereof.

The pharmaceutical compositions of the present invention can comprise a combination of two or more types of the peptides of the present invention. The combination of peptides can take a cocktail form of mixed peptides, or can be conjugated with each other using standard techniques. For example, peptides can be chemically linked or expressed as single fusion polypeptide sequences. By administering a peptide of the present invention, the peptide is presented on APCs by an HLA antigen at a high density, and then subsequently CTLs that react specifically to a complex formed between the presented peptide and the HLA antigen are induced. Alternatively, APCs (for example, DCs) are removed from a subject, and subsequently stimulated with peptides of the present invention to obtain APCs that present any of the peptides of the present invention on their cell surface. These APCs are re-administered to a subject to induce CTLs in the subject, and as a result, the aggressiveness towards coronavirus-infected cells can be increased. Neutralizing antibodies may lose their ability to block infection (viral immune escape) due to a mutation in their target epitope. In general, the effect of an antigen mutation is particularly significant in monoclonal antibodies, which depend on a single epitope for antigen-binding specificity. On the other hand, when the pharmaceutical composition comprises multiple CTL epitopes (cocktail), even if any of the epitopes is mutated, CTLs recognizing other epitopes are effective. Mixing epitopes derived from multiple proteins is an effective strategy for avoiding a reduction in therapeutic effect due to viral immune escape.

The pharmaceutical compositions of the present invention may also comprise an adjuvant known for effectively establishing cellular immunity. An adjuvant refers to a compound that enhances the immune response against an antigen that has immunological activity when administered together (or successively) with the antigen. Known adjuvants described in literatures, for example, Clin Microbiol Rev 1994, 7: 277-89, can be used. Examples of a suitable adjuvant include aluminum salts (aluminum phosphate, aluminum hydroxide, aluminum oxyhydroxide and such), alum, cholera toxin, Salmonella toxin, Incomplete Freund's adjuvant (IFA), Complete Freund's adjuvant (CFA), ISCOMatrix, GM-CSF and other immunostimulatory cytokines, oligodeoxynucleotide containing the CpG motif (CpG7909 and such), oil-in-water emulsions, Saponin or its derivatives (QS21 and such), lipopolysaccharide such as Lipid A or its derivatives (MPL, RC529, GLA, E6020 and such), lipopeptides, lactoferrin, flagellin, double-stranded RNA or its derivatives (poli IC and such), bacterial DNA, imidazoquinolines (Imiquimod, R848 and such), C-type lectin ligand (trehalose-6,6'-dibehenate (TDB) and such), CD1d ligand (alpha-galactosylceramide and such), squalene emulsions (MF59, AS03, AF03 and such), PLGA, and such, without being limited thereto. In a certain embodiment, the pharmaceutical composition of the present invention may comprise an adjuvant in an amount sufficient to stimulate an immune response.

The adjuvant may be contained in another container separate from the pharmaceutical composition comprising a peptide of the present invention in the kits comprising the pharmaceutical composition of the present invention. In this case, the adjuvant and the pharmaceutical composition may be administered to a subject in succession, or mixed together immediately before administration to a subject. Such kits comprising a pharmaceutical composition comprising a peptide of the present invention and an adjuvant are also provided by the present invention. When the pharmaceutical composition of the present invention is a freeze-dried formulation, the kit can further comprise a re-dissolving solution. Further, the present invention provides kits comprising a container that houses a pharmaceutical composition of the present invention and a container that stores an adjuvant. The kit can further comprise as needed a container that stores the re-dissolving solution.

When an oil adjuvant is used as an adjuvant, the pharmaceutical composition of the present invention may be prepared as an emulsion. Emulsions can be prepared, for example, by mixing and stirring the peptide solution prepared as described above and an oil adjuvant. The peptide solution may be one that has been re-dissolved after freeze-drying. The emulsion may be either of the W/O-type emulsion and O/W-type emulsion, and the W/O-type emulsion is preferred for obtaining a high immune response-enhancing effect. IFA can be preferably used as an oil adjuvant, without being limited thereto. Preparation of an emulsion can be carried out immediately before administration to a subject, and in this case, the pharmaceutical composition of the present invention may be provided as a kit comprising the peptide solution of the present invention and an oil adjuvant. When the pharmaceutical composition of the present invention is a freeze-dried formulation, the kit can further comprise a re-dissolving solution.

Further, the pharmaceutical composition of the present invention may be a liposome formulation within which a peptide of the present invention is encapsulated, a granular formulation in which a peptide is bound to beads with several micrometers in diameter, or a formulation in which a lipid is bound to a peptide.

In another embodiment of the present invention, the peptide of the present invention may also be administered in the form of a pharmaceutically acceptable salt. Preferred examples of salts include salts with alkali metals (lithium, potassium, sodium and such), salts with alkaline-earth metals (calcium, magnesium and such), salts with other metals (copper, iron, zinc, manganese and such), salts with organic bases, salts with amines, salts with organic acids (acetic acid, formic acid, propionic acid, fumaric acid, maleic acid, succinic acid, tartaric acid, citric acid, malic acid, oxalic acid, benzoic acid, methanesulfonic acid and such), and salts with inorganic acids (hydrochloric acid, phosphoric acid, hydrobromic acid, sulfuric acid, nitric acid and such). Therefore, pharmaceutical compositions comprising a pharmaceutically acceptable salt of a peptide of the present invention are also encompassed by the present invention. Further, the "peptide of the present invention" also encompasses, in addition to the free peptide, pharmaceutically acceptable salts thereof.

In some embodiments, the pharmaceutical compositions of the present invention may further include a component which primes CTLs. Lipids have been identified as substances capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTLs when covalently attached to an appropriate peptide (see, e.g., Deres et al., Nature 1989, 342: 561-4).

Examples of methods for administering the peptides or pharmaceutical compositions of the present invention include oral, epidermal, subcutaneous, intramuscular, intraosseous, peritoneal, and intravenous injections, as well as systemic administration or local administration to the vicinity of the targeted sites, but are not limited thereto. A preferred administration method includes subcutaneous injection to the vicinity of lymph nodes such as the armpit or groin. The administration can be performed by single administration or boosted by multiple administrations. The peptides of the present invention can be administered to a subject in a therapeutically or pharmaceutically effective amount for treating coronavirus infectious disease or in a therapeutically or pharmaceutically effective amount for inducing immunity (more specifically CTLs) against coronavirus-infected cells. The dose of the peptides of the present invention can be appropriately adjusted according to the disease target for treatment or prevention (prophylaxis), the patient's age and weight, the method of administration and such. For each of the peptides of the present invention, the dose is usually 0.001 mg-1000 mg, for example, 0.01 mg-100 mg, for example, 0.1 mg-30 mg, for example, 0.1 mg-10 mg, for example, 0.5 mg-5 mg. The dosing interval can be once every several days to several months, and for example, the dosing can be done in a once-per-week interval. A skilled artisan can appropriately select a suitable dosage.

In a preferred embodiment, the pharmaceutical compositions of the present invention comprise a therapeutically effective amount of a peptide of the present invention and a pharmaceutically or physiologically acceptable carrier. In another embodiment, the pharmaceutical compositions of the present invention comprise a therapeutically effective amount of a peptide of the present invention, a pharmaceutically or physiologically acceptable carrier, and an adjuvant. The pharmaceutical compositions of the present invention can comprise 0.001 mg-1000 mg, preferably 0.01 mg-100 mg, more preferably 0.1 mg-30 mg, even more preferably 0.1 mg-10 mg, for example, 0.5 mg-5 mg of a peptide of the present invention. When a pharmaceutical composition of the present invention is an injection, it can comprise a peptide of the present invention at a concentration of 0.001 mg/ml-1000 mg/ml, preferably 0.01 mg/ml- 100 mg/ml, more preferably 0.1 mg/ml-30 mg/ml, even more preferably 0.1 mg/ml-10 mg/ml, for example, 0.5 mg/ml-5 mg/ml. In this case, for example, 0.1 to 5 ml, preferably 0.5 ml to 2 ml of the pharmaceutical composition of the present invention can be administered to a subject by injection. On the other hand, when a pharmacological composition of the present invention comprises an adjuvant, the adjuvant can be contained in an amount that is effective in enhancing the immune response of a subject against the peptide.

Further, the present invention provides methods of any one of purposes selected from treatment of, prevention (prophylaxis) of and suppression of aggravation of coronavirus infectious disease, or multiple purposes, which comprise administering to a subject a therapeutically effective amount of a peptide of the present invention or a pharmaceutical composition of the present invention. As described above, the peptides of the present invention can be administered to a subject in a single dose of usually 0.001 mg-1000 mg, for example, 0.01 mg-100 mg, for example, 0.1 mg-30 mg, for example, 0.1 mg-10 mg, or for example, 0.5 mg-5 mg. In a preferred embodiment, the peptides of the present invention are administered to a subject together with an adjuvant. Further, the dosing interval can be once every several days to several months, preferably once every several days to every month, for example, once every week or once every two weeks. On the other hand, when an adjuvant is administered with a peptide in the method of the present invention, the adjuvant can be administered in an amount that is effective in enhancing the immune response of a subject against the peptide.

(2) Pharmaceutical Compositions Containing Polynucleotides as the Active Ingredient The pharmaceutical compositions of the present invention can also contain polynucleotides encoding the peptides of the present invention in an expressible form. Herein, the phrase "in an expressible form" means that the polynucleotide, when introduced into a cell, will be expressed as a peptide of the present invention. In an exemplified embodiment, the sequence of the polynucleotide of the present invention includes regulatory elements necessary for expression of the peptide of the present invention. The polynucleotide(s) of the present invention can be equipped with a sequence necessary to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859, 5,589,466, 5,804,566, 5,739,118, 5,736,524, 5,679,647; and WO98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. For example, as a vector to express the peptide of the present invention, vaccinia virus can be used. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, Salmonella typhi vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide of the present invention into a patient can be either direct, in which case the patient can be directly exposed to a vector harboring the polynucleotide of the present invention, or indirect, in which case, cells are first transformed with the vector harboring the polynucleotide of the present invention in vitro, then the cells are transplanted into the patient. These two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215. Methods commonly known in the art of recombinant DNA technology which can also be used for the present invention are described in Ausubel et al., Current Protocols in Molecular Biology; John Wiley & Sons, N Y, 1993; and Krieger, Gene Transfer and Expression, A Laboratory Manual, Stockton Press, N Y, 1990. Administration may be performed by oral, intradermal, subcutaneous, or intravenous injection, and such. A systemic administration or a local administration to the vicinity of the targeted sites is used.

The administration can be performed by single administration or boosted by multiple administrations. The polynucleotides of the present invention can be administered to a subject in a therapeutically or pharmaceutically effective dose for treating coronavirus infectious disease or in a therapeutically or pharmaceutically effective dose for inducing immunity (more specifically CTLs) against coronavirus-infected cells. The dose of a polynucleotide in a suitable carrier or the dose of a polynucleotide in cells transformed with a polynucleotide encoding a peptide of the present invention can be appropriately adjusted according to the disease to be treated, the patient's age and weight, the method of administration and such, and this may be usually 0.001 mg-1000 mg, for example, 0.01 mg-100 mg, for example, 0.1 mg-30 mg, for example, 0.1 mg-10 mg, or for example, 0.5 mg-5 mg. The dosing interval can be once every several days to several months, and for example, the dosing can be done in a once-per-week interval. A skilled artisan can appropriately select a suitable dosage.

X. Methods of Using Peptides, Exosomes, APCs and CTLs

The peptides and polynucleotides of the present invention can be used to induce APCs and CTLs. CTLs can also be induced using the exosomes and APCs of the present invention. The peptides, polynucleotides, exosomes, and APCs can be used in combination with any other compound(s) as long as their CTL-inducing ability is not inhibited. Therefore, CTLs of the present invention can be induced using a pharmaceutical composition comprising any of the peptides, polynucleotides, APCs and exosomes of the present invention. Further, APCs of the present invention can be induced using a pharmaceutical composition comprising a peptide or polynucleotide of the present invention.

(1) Methods of Inducing APCs

The present invention provides methods of inducing APCs having CTL-inducing ability, using a peptide(s) or polynucleotide(s) of the present invention.

The methods of the present invention comprise a step of contacting an APC with a peptide of the present invention in vitro, ex vivo, or in vivo. For example, a method of contacting APCs with the peptide ex vivo may comprise the steps below:

(a) collecting APCs from a subject; and (b) contacting the APCs of step (a) with a peptide of the present invention.

The above-described APCs are not limited to a particular type of cell, and cells known to present a proteinaceous antigen on their cell surface to be recognized by lymphocytes, for example, DCs, Langerhans cells, macrophages, B cells, and activated T cells can be used. DCs have the most potent CTL-inducing ability among APCs, and thus it is preferable to use DCs. Any peptides of the present invention can be used by themselves or in combination with other peptides of the present invention. Further, peptides of the present invention can be used in combination with other CTL-inducing peptides (for example, other coronavirus protein-derived CTL-inducing peptides). In a certain embodiment, the methods of the present invention may further additionally comprise the step of collecting the APCs after step (b).

Meanwhile, when a peptide of the present invention is administered to a subject, APCs are contacted with the peptide in vivo, and as a result, APCs having a high CTL-inducing ability are induced in the body of the subject. Therefore, the methods of the present invention may comprise a step of administering a peptide of the present invention to a subject. Similarly, when a polynucleotide of the present invention is administered to a subject in an expressible form, a peptide of the present invention is expressed in vivo, the expressed peptide is contacted with APCs in vivo, and as a result APCs having a high CTL-inducing ability are induced in the body of the subject. Therefore, the present invention may also comprise a step of administering a polynucleotide of the present invention to a subject.

In order to induce APCs having CTL-inducing ability, the present invention may comprise a step of introducing a polynucleotide of the present invention into APCs. For example, the method may comprise the steps below:

(a) collecting APCs from a subject; and (b) introducing a polynucleotide encoding a peptide of the present invention into the APCs of step (a).

Step (b) can be performed as described in the above "VI. Antigen-presenting cells (APCs)" section.

Thus, in one embodiment, the present invention provides a method of inducing APCs having CTL-inducing ability, which comprises the step (a) or (b) below:

(a) contacting APCs with a peptide of the present invention; or (b) introducing a polynucleotide encoding a peptide of the present invention into APCs.

Furthermore, the present invention provides a method of preparing APCs having CTL-inducing ability, which comprises the step (a) or (b) below:

(a) contacting APCs with a peptide of the present invention; or (b) introducing a polynucleotide encoding a peptide of the present invention into APCs.

The above-described methods can be performed in vitro, ex vivo, or in vivo, and it is preferable to perform them in vitro or ex vivo. APCs used in the above-described methods may be derived from a subject scheduled for administration of the induced APCs, or they may be derived from a different subject. In a certain embodiment, the methods of the present invention may further additionally comprise the step of collecting the APCs after step (b).

When APCs derived from a subject (donor) different from the subject scheduled for administration are used, the subject of administration and the donor must have the identical HLA type. In the methods of the present invention, when a peptide having the amino acid sequence selected from among SEQ ID NOs: 1, 2, 3, 4, 5, 7, 9, 10, 11, 12, 13 and 15 or a modified peptide thereof is used as a peptide of the present invention, the HLA type is preferably HLA-A24 (more preferably HLA-A*24:02) in both the subject of administration and the donor. Alternatively, APCs used in the above-described methods are preferably APCs that express HLA-A24 (more preferably HLA-A*24:02).

When a peptide having the amino acid sequence selected from among SEQ ID NOs: 1, 2, 4, 7, 10, 12 and 13 or a modified peptide thereof is used as a peptide of the present invention, the HLA type is preferably HLA-A02 (more preferably HLA-A*02:01) in both the subject of administration and the donor. Alternatively, APCs used in the above-described methods are preferably APCs that express HLA-A02 (more preferably HLA-A*02:01). The APCs can be prepared using known methods from PBMCs after PBMCs are separated from blood collected from a donor by a specific gravity centrifugal method or such.

In another embodiment, the present invention also provides pharmaceutical compositions that comprise a peptide of the present invention or a polynucleotide encoding the peptide for inducing an APC(s) having CTL-inducing ability.

Alternatively, the present invention further provides use of a peptide of the present invention or a polynucleotide encoding the peptide in the manufacture of a pharmaceutical composition for inducing an APC(s) having CTL-inducing ability.

Alternatively, the present invention further provides peptides of the present invention or polynucleotides encoding the peptides for use in the induction of an APC(s) having CTL-inducing ability.

Alternatively, the present invention further provides methods or processes of manufacturing a pharmaceutical composition for inducing an APC(s), wherein the method or process comprises a step of formulating a peptide of the present invention or a polynucleotide encoding the peptide with a pharmaceutically or physiologically acceptable carrier.

In another embodiment, the present invention further provides methods or processes of manufacturing a pharmaceutical composition for inducing an APC(s) having CTL-inducing ability, wherein the method or process comprises a step of mixing a peptide of the present invention or a polynucleotide encoding the peptide with a pharmaceutically or physiologically acceptable carrier.

APCs induced by the methods of the present invention can induce CTLs specific to coronavirus protein (i.e., CTLs of the present invention).

(2) Methods of Inducing CTLs

The present invention also provides methods of inducing CTLs using peptides, polynucleotides, exosomes or APCs of the present invention.

When a peptide(s), a polynucleotide(s), an exosome(s) or an APC(s) of the present invention is administered to a subject, CTLs are induced in the body of the subject and the strength of the immune response targeting coronavirus-infected cells is enhanced. Therefore, the methods of the present invention may comprise a step of administering a peptide(s), a polynucleotide(s), an APC(s) or an exosome(s) of the present invention to a subject.

Alternatively, CTLs can be induced by using them in vitro or ex vivo. For example, the methods of the present invention may include the following steps:

(a) collecting APCs from a subject;

(b) contacting the APCs of step (a) with a peptide of the present invention; and (c) co-culturing the APCs of step (b) with CD8-positive T cells.

The induced CTLs may be returned to the subject afterwards.

The APCs to be co-cultured with the CD8-positive T cells in step (c) above can also be prepared by introducing into APCs a polynucleotide encoding a peptide of the present invention as described above in the "VI. Antigen-presenting cells (APCs)" section. However, the APCs to be used in the methods of the present invention are not limited thereto, and any APCs that present on their surface a complex of an HLA antigen and a peptide of the present invention can be used.

In the methods of the present invention, instead of such APCs, exosomes that present on their surface a complex of an HLA antigen and a peptide of the present invention can also be used. That is, the methods of the present invention can comprise a step of co-culturing with exosomes that present on their surface a complex of an HLA antigen and a peptide of the present invention. Such exosomes can be prepared by the above-described methods in the "V. Exosomes" section.

Further, CTLs can also be induced by introducing into a CD8-positive T cell a vector comprising a polynucleotide encoding each subunit of a TCR capable of binding to a peptide of the present invention presented by an HLA antigen on the cell surface. Such transformation can be carried out as described above in the "VIII. T cell receptors (TCRs)" section.

Accordingly, in one embodiment, the present invention provides methods of inducing CTLs, comprising a step selected from below:

(a) co-culturing CD8-positive T cells with APCs that present on their surface a complex of an HLA antigen and a peptide of present invention;

(b) co-culturing CD8-positive T cells with exosomes that present on their surface a complex of an HLA antigen and a peptide of present invention; and (c) introducing into CD8-positive T cells, a vector comprising a polynucleotide encoding each subunit of a TCR capable of binding to a peptide of the present invention presented by an HLA antigen on a cell surface.

The above-described methods can be performed in vitro, ex vivo, or in vivo, and it is preferable to perform them in vitro or ex vivo. When performed in vitro or ex vivo, in a certain embodiment, the methods of the present invention may comprise the step of collecting induced CTLs after any one of the steps. APCs or exosomes and CD8-positive T cells used in the above-described methods may be derived from a subject scheduled for administration of the induced CTLs, or they may be derived from a different subject. When APCs or exosomes and CD8-positive T cells derived from a subject (donor) different from the subject scheduled for administration are used, the subject of administration and the donor must have the identical HLA type. For example, when a peptide having the amino acid sequence selected from among SEQ ID NOs: 1, 2, 3, 4, 5, 7, 9, 10, 11, 12, 13 and 15 or a modified peptide thereof is used as peptides of the present invention, the HLA type in both the subject of administration and the donor is preferably HLA-A24 (more preferably HLA-A*24:02). Alternatively, APCs or exosomes used in the above-described methods are preferably APCs or exosomes that present on their surface a complex of HLA-A24 (more preferably HLA-A*24:02) and a peptide of the present invention (a peptide having the amino acid sequence selected from among SEQ ID NOs: 1, 2, 3, 4, 5, 7, 9, 10, 11, 12, 13 and 15 or a modified peptide thereof). In this case, the induced CTLs show a specific cytotoxic activity against cells that present a complex of HLA-A24 and a peptide of the present invention (for example, coronavirus-infected HLA-A24-positive cells).

When a peptide having the amino acid sequence selected from among SEQ ID NOs: 1, 2, 4, 7, 10, 12 and 13 or a modified peptide thereof is used as peptides of the present invention, the HLA type in both the subject of administration and the donor is preferably HLA-A02 (more preferably HLA-A*02:01). Alternatively, APCs or exosomes used in the above-described methods are preferably APCs or exosomes that present on their surface a complex of HLA-A02 (more preferably HLA-A*02:01) and a peptide of the present invention (a peptide having the amino acid sequence selected from among SEQ ID NOs: 1, 2, 4, 7, 10, 12 and 13 or a modified peptide thereof). In this case, the induced CTLs show a specific cytotoxic activity against cells that present a complex of HLA-A02 and a peptide of the present invention (for example, coronavirus-infected HLA-A02-positive cells).

In another embodiment, the present invention also provides compositions or pharmaceutical compositions for inducing CTLs, comprising at least one active ingredient selected from below:

(a) a peptide of the present invention;

(b) a polynucleotide encoding a peptide of the present invention in an expressible form;

(c) an APC that presents on its surface a peptide of the present invention; and (d) an exosome that presents on its surface a peptide of the present invention.

In another embodiment, the present invention also provides use of an active ingredient selected from below in the manufacture of compositions or pharmaceutical compositions for inducing CTLs:

(a) a peptide of the present invention;

(b) a polynucleotide encoding a peptide of the present invention in an expressible form;

(c) an APC that presents on its surface a peptide of the present invention; and (d) an exosome that presents on its surface a peptide of the present invention.

Alternatively, the present invention further provides an active ingredient selected from below for use in inducing CTLs:

(a) a peptide of the present invention;

(b) a polynucleotide encoding a peptide of the present invention in an expressible form;

(c) an APC that presents on its surface a peptide of the present invention; and (d) an exosome that presents on its surface a peptide of the present invention.

Alternatively, the present invention further provides a method or process for manufacturing a composition or pharmaceutical composition for inducing CTLs, which is a method or process that comprises a step of formulating an active ingredient selected from below with a pharmaceutically or physiologically acceptable carrier:

(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

In another embodiment, the present invention further provides a method or process for manufacturing a composition or pharmaceutical composition for inducing CTLs, which is a method or process that comprises a step of mixing an active ingredient selected from below with a pharmaceutically or physiologically acceptable carrier:

(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

XI. Methods of Inducing an Immune Response

The present invention further provides methods of inducing an immune response against coronavirus infection. Coronaviruses include SARS-CoV-2, MERS-CoV, SARS-CoV and such, but are not limited thereto. It is preferable that the coronavirus-infected cells express HLA-A24 or HLA-A02.

The present invention also provides methods of inducing an immune response against coronavirus-infected cells. The peptides of the present invention are derived from structural or non-structural proteins of SARS-CoV-2, and are amino acid sequences commonly found also in SARS-CoV proteins and MERS-CoV proteins. Thus, when an immune response against coronavirus-infected cells is induced, proliferation of viruses in the coronavirus-infected cells is inhibited as a result. Accordingly, the present invention further provides methods of inhibiting proliferation of viruses in coronavirus-infected cells. The methods of the present invention are suitable, in particular, for inhibiting proliferation of coronaviruses in coronavirus-infected cells expressing HLA-A24 or HLA-A02.

The methods of the present invention may comprise a step of administering a composition comprising any of the peptides of the present invention or a polynucleotide(s) encoding the peptide(s). The methods of the present invention also contemplate administration of APCs or exosomes presenting any of the peptides of the present invention. The details can be referred to the "IX. Pharmaceutical compositions" section, particularly portions describing regarding use of the pharmaceutical compositions of the present invention as vaccines. In addition, exosomes and APCs that can be used in the methods of the present invention for inducing an immune response are described in detail in "V. Exosomes", "VI. Antigen-presenting cells (APCs)" and in Items (1) and (2) of "X. Methods of using peptides, exosomes, APCs and CTLs" described above.

In another embodiment, the present invention provides pharmaceutical compositions or vaccines for inducing an immune response against coronavirus infection, wherein the pharmaceutical composition or vaccine comprises an active ingredient selected from below:

(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention also provides pharmaceutical compositions or vaccines for inducing an immune response against coronavirus-infected cells, wherein the pharmaceutical composition or vaccine comprises an active ingredient selected from below:

(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention further provides pharmaceutical compositions or vaccines for inhibiting proliferation of coronaviruses in coronavirus-infected cells, wherein the pharmaceutical composition or vaccine comprises an active ingredient selected from below:

(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

In another embodiment, the present invention provides use of an active ingredient selected from below in the manufacture of pharmaceutical compositions or vaccines for inducing an immune response against coronavirus infection:

(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention also provides use of an active ingredient selected from below in the manufacture of pharmaceutical compositions or vaccines for inducing an immune response against coronavirus-infected cells:

(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention further provides use of an active ingredient selected from below in the manufacture of pharmaceutical compositions or vaccines for inhibiting proliferation of coronaviruses in coronavirus-infected cells:

(a) a peptide of the present invention;
(b) a polynucleotide encoding a peptide of the present invention in an expressible form;
(c) an APC that presents on its surface a peptide of the present invention;

(d) an exosome that presents on its surface a peptide of the present invention; and
(e) a CTL of the present invention.

The present invention further provides methods or processes for manufacturing pharmaceutical compositions that induce an immune response against coronavirus infection, which is a method that may comprise a step of mixing or formulating a peptide of the present invention with a pharmaceutically acceptable carrier.

Alternatively, the present invention provides methods for inhibiting proliferation of coronaviruses in coronavirus-infected cells or methods of inducing an immune response against coronavirus infection, which comprises a step of administering to a subject vaccines or pharmaceutical compositions comprising an active ingredient selected from below:
(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In the context of the present invention, coronavirus infectious diseases can be treated by administering a peptide, a polynucleotide, an APC, an exosome and/or a CTL of the present invention. Alternatively, an immune response against coronavirus infection can be induced by administering a peptide, a polynucleotide, an APC, an exosome and/or a CTL of the present invention. Examples of such coronaviruses include SARS-CoV-2, MERS-CoV, SARS-CoV and such, but are not limited thereto. Further, an immune response against coronavirus-infected cells can be induced by administering a peptide, a polynucleotide, an APC, an exosome and/or a CTL of the present invention. Therefore, whether the subject to be treated is infected with coronavirus or not may also be confirmed before administering a vaccine or pharmaceutical composition comprising an active ingredient described above.

Thus, in one embodiment, the present invention provides a method of treating a coronavirus infectious disease in a patient in need of the infectious disease treatment, wherein the method comprises the steps below:
(i) measuring an expression level of a SARS-CoV-2 gene or a protein encoded thereby in a biological sample collected from a subject infected with coronavirus;
(ii) identifying a subject infected with coronavirus based on the expression level of the SARS-CoV-2 gene or the protein encoded thereby measured in (i); and
(iii) administering to the subject infected with coronavirus at least one ingredient selected from the group consisting of (a) to (e) above.

Alternatively, the present invention further provides vaccines and pharmaceutical compositions comprising at least one active ingredient selected from the group consisting of (a) to (e) above for administration to a subject infected with coronavirus. The present invention further provides a method of identifying or selecting a subject to be treated with at least one active ingredient selected from the group consisting of (a) to (e) above, wherein the method comprises the steps below:
(i) measuring an expression level of a SARS-CoV-2 gene or a protein encoded thereby in a biological sample collected from a subject infected with coronavirus;
(ii) identifying a subject with coronavirus-infected cells expressing the SARS-CoV-2 gene or the protein encoded thereby based on the expression level of the SARS-CoV-2 gene or the protein encoded thereby measured in (i); and
(iii) identifying or selecting the subject identified in (ii) as a subject who may be treated with at least one active ingredient selected from the group consisting of (a) to (e) above.

Biological samples collected from a subject for measuring the expression level of a SARS-CoV-2 gene or a protein encoded thereby in the above-described methods are not particularly limited, and for example, tissue samples containing coronavirus-infected cells collected by biopsy or such can be preferably used. Alternatively, detecting coronavirus RNAs in throat swab or saliva is generally performed in identifying coronavirus-infected subject. Thus, in the present invention, a coronavirus gene includes genome RNA of coronavirus, or mRNAs transcribed therefrom. The expression level of a SARS-CoV-2 gene or a protein encoded thereby in a biological sample can be measured by known methods, and for example, methods that detect transcription products of the SARS-CoV-2 gene by probes or PCR methods (for example, cDNA microarray method, Northern blot method, RT-PCR method or such), methods that detect translation products of the SARS-CoV-2 gene by antibodies or such (for example, Western blot method, immunostaining method, immunochromatography method or such), and such can be used. Further, biological samples may be blood samples, and in this case, the blood level of an antibody against SARS-CoV-2 protein is measured, and the expression level of SARS-CoV-2 protein may be assessed based on the blood level. The blood level of an antibody against SARS-CoV-2 protein can be measured using known methods, and for example, enzyme immunoassay (EIA), enzyme-linked immunosorbent assay (ELISA), radioimmunoassay (RIA) and such using the SARS-CoV-2 protein or a peptide of the present invention as an antigen can be used.

Alternatively, the expression level of a SARS-CoV-2 protein in a subject may be assessed by detecting CTLs specific to a peptide of the present invention. The level of CTLs specific to a peptide of the present invention can be measured, for example, by isolating PBMCs from the blood collected from a subject and measuring their cytotoxic activity against target cells pulsed with the peptide of the present invention. Cytotoxic activity can be measured, for example, by the amount of interferon γ released. Complexes of the peptide of the present invention and HLA, mentioned below, can also be used to measure CTL levels. The determination of whether the coronavirus-infected cells that the subject has express a SARS-CoV-2 protein may be made by comparison with the measurement results in the same type of biomaterial collected from a subject not infected with the coronavirus. That is, when the level of a measuring object in a biological sample collected from a coronavirus-infected subject is elevated compared to that in the same type of biomaterial collected from a subject not infected with the coronavirus (normal control level), the cells of the coronavirus-infected subject can be judged to express the SARS-CoV-2 protein.

In a preferred embodiment, it is preferable to confirm the HLA type of the subject before administering at least one active ingredient selected from the group consisting of (a) to (e) above. For example, for the subjects to be administered with an active ingredient in association with a peptide having the amino acid sequence selected from among SEQ ID NOs: 1, 2, 3, 4, 5, 7, 9, 10, 11, 12, 13 and 15, it is preferable to select HLA-A24-positive subjects. For the subjects to be administered with an active ingredient in association with a peptide having the amino acid sequence selected from among SEQ ID NOs: 1, 2, 4, 7, 10, 12 and 13, it is preferable to select HLA-A02-positive subjects. Methods for determining HLA haplotypes, so-called HLA typing, are well known to those skilled in the art. Alternatively, the lymphocyte cytotoxicity test (LCT method), in which HLA types are determined by the reactivity of antibodies specific to each HLA with HLA antigens on lymphocytes, and the like are also known.

The present invention further provides complexes of a peptide of the present invention and HLA. The complexes of the present invention described above may be monomers or multimers. When a complex of the present invention is a multimer, the number of polymerization is not particularly limited, and it can be a multimer of any number of polymerization. Examples include a tetramer, pentamer, hexamer and such, but are not limited thereto. The multimers of the present invention also encompass dextramers (WO2002/072631) and streptamers (Knabel M et al., Nat Med. 2002 June; 8(6): 631-7). Complexes of a peptide of the present invention and HLA can be prepared according to known methods (for example, Altman J D et al., Science. 1996, 274(5284): 94-6; WO2002/072631; WO2009/003492; Knabel M et al., Nat Med. 2002 June; 8(6): 631-7; and such). The complexes of the present invention, for example, can be used in the quantification of CTLs specific to a peptide of the present invention. For example, a blood sample is collected from a subject administered with a pharmaceutical composition of the present invention, and CD4-negative cells are prepared after separation of PBMCs and contacted with a fluorescent dye-conjugated complex of the present invention. Then, the percentage of CTLs specific to a peptide of the present invention can be measured by flow cytometry analysis. For example, immune response-inducing effects by a pharmaceutical composition of the present invention can be monitored by measuring CTLs specific to a peptide of the present invention before, during and/or after administration of the pharmaceutical composition of the present invention.

XII. Antibodies

The present invention further provides antibodies that bind to the peptide of the present invention. Preferable antibodies bind specifically to a peptide of the present invention, but do not bind (or weakly bind) to one that is not the peptide of the present invention. The binding specificity of an antibody can be confirmed by inhibition assay. That is, if the binding between an antibody to be analyzed and a polypeptide (SEQ ID NOs: 17-26) consisting of an amino acid sequence of each protein encoded by a full-length genome sequence of SARS-CoV-2 is inhibited in the presence of a peptide of the present invention, this antibody is shown to specifically bind to the peptide of the present invention. Antibodies against peptides of the present invention can be used in assays of disease diagnosis and prognosis, as well as subject selection for administration of the pharmaceutical compositions of the present invention and monitoring of the pharmaceutical compositions of the present invention.

The present invention also provides various immunological assays for detecting and/or quantifying peptides of the present invention or fragments thereof. Such immunological assays include radioimmunoassay, immunochromatography, enzyme-linked immunosorbent assay (ELISA), enzyme-linked immunofluorescence assay (ELIFA) and such, without being limited thereto, and are performed within the scope of the various immunological assay formats well known in the art.

The antibodies of the present invention can be used in immunological imaging methods that can detect coronavirus-infected cells, and examples thereof include radioactive scintigraphic imaging using a labelled antibody of the present invention, without being limited thereto. Such assay methods are used clinically in the detection, monitoring, and prognosis of coronavirus-infected cells; and examples of such coronaviruses of coronavirus infectious diseases include SARS-CoV-2, MERS-CoV, SARS-CoV and such, without being limited thereto.

The antibodies of the present invention can be used in any arbitrary form such as monoclonal antibodies or polyclonal antibodies, and may further include anti-sera obtained by immunizing an animal such as a rabbit with a peptide of the present invention, all classes of polyclonal antibodies and monoclonal antibodies, human antibodies, as well as chimeric antibodies and humanized antibodies generated through gene recombination.

The peptide of the present invention or a fragment thereof used as an antigen for obtaining antibodies can be obtained by chemical synthesis or genetic engineering techniques based on the amino acid sequences disclosed herein.

The peptide used as an immunizing antigen may be a peptide of the present invention or a fragment of a peptide of the present invention. Further, the peptide may be bound to or conjugated with a carrier for increasing immunogenicity. Keyhole limpet hemocyanin (KLH) is well-known as a carrier. Methods for binding KLH to a peptide are also well known in the art.

Any mammal can be immunized with an antigen described above, and it is preferable to consider the compatibility with the parent cell used in cell fusion when generating a monoclonal antibody. Generally, animals of the order Rodentia, Lagomorpha or Primate can be used. Animals of the order Rodentia include, for example, mice, rats and hamsters. Animals of the order Lagomorpha include, for example, rabbits. Animals of the order Primate include, for example, Catarrhini monkeys (old world monkeys) such as cynomolgus monkey (*Macaca fascicularis*), rhesus monkeys, hamadryas, and chimpanzee.

Methods of immunizing animals with an antigen are known in the art. Intraperitoneal injection and subcutaneous injection of an antigen are standard methods for immunizing mammals. More specifically, an antigen is diluted and suspended in an appropriate amount of phosphate buffered saline (PBS), physiological saline, or such. As needed, an antigen suspension solution can be administered to mammals after being mixed with an appropriate amount of a standard adjuvant such as Freund's complete adjuvant and emulsified. Then, it is preferable to administer the antigen mixed with an appropriate amount of a Freund's incomplete adjuvant several times every 4 to 21 days. A suitable carrier may be used for immunization. After the above immunization, the serum can be examined by standard method with respect to increase in the quantity of the desired antibody.

Polyclonal antibodies against a peptide of the present invention can be prepared by collecting blood from mammals that have been confirmed with an increase in the serum level of the desired antibody after immunization, and separating the serum from blood by any conventional method. A polyclonal antibody may be a polyclonal antibody-containing serum, or a polyclonal antibody-containing fraction may be isolated from the serum. Immunoglobulin G or M can be prepared from fractions that recognize only a peptide of the present invention by, for example, using an affinity column conjugated with the peptide of the present invention, and then further purifying the fractions using a protein A or protein G column.

In order to prepare monoclonal antibodies, upon confirming an increase in the serum level of the desired antibody after immunization, immune cells are collected from the mammals and subjected to cell fusion. Immune cells used for cell fusion may be preferably obtained from the spleen. For the other parent cells fused with the above immune cells, for example, a mammalian myeloma cell, and more preferably a myeloma cell that has acquired a property for drug selection of fusion cells can be used.

The above immune cells can be fused with myeloma cells known methods, for example, the method of Milstein et al. (Galfre and Milstein, Methods Enzymol 73: 3-46 (1981)).

Hybridomas obtained by cell fusion can be selected by culturing them in a standard selection medium such as the HAT medium (a medium containing hypoxanthine, aminopterin and thymidine). Cell culturing is typically continued in the HAT medium for a sufficient period of time (for example, several days to several weeks) to allow death of all other cells (non-fused cells) besides the desired hybridomas. Then, hybridoma cells producing the desired antibody can be screened and cloned by performing a standard limiting dilution.

In addition to the above methods of immunizing a non-human animal with an antigen for hybridoma preparation, human lymphocytes such as EB virus-infected lymphocytes can be immunized in vitro with a peptide, cells expressing the peptide, or lysates thereof. Then, the immunized lymphocytes can be fused with immortalized human-derived myeloma cells such as U266 to obtain hybridomas producing a desired human antibody capable of binding to the peptide (JPS63-17688).

Next, the obtained hybridoma is transplanted into the abdominal cavity of a mouse, and the ascites is extracted. The obtained monoclonal antibody can be purified by, for example, ammonium sulfate precipitation, protein A or protein G column, DEAE ion-exchange chromatography, or affinity column conjugated with the peptide of the present invention.

Alternatively, antibody-producing immune cells such as the immunized lymphocytes can be immortalized by a cancer gene and used for the preparation of monoclonal antibodies.

The monoclonal antibodies obtained as such can also be prepared by recombination using genetic engineering techniques (see, e.g., Borrebaeck and Larrick, Therapeutic Monoclonal Antibodies published in United Kingdom by MacMillan Publishers LTD (1990)). For example, an antibody-encoding DNA can be cloned from immune cells such as antibody-producing hybridoma or immunized lymphocytes and inserted into a suitable vector, and then this is introduced into host cells to prepare a recombinant antibody. The present invention also provides recombinant antibodies prepared as described above.

Further, the antibodies of the present invention may be antibody fragments or modified antibodies, as long as they bind to the peptides of the present invention. For example, the antibody fragments may be Fab, $F(ab')_2$, Fv, or a single chain Fv (scFv) in which Fv fragments derived from an H chain and an L chain are linked with a suitable linker (Huston et al., Proc Natl Acad Sci USA 85: 5879-83 (1988)). More specifically, antibody fragments may be generated by treating an antibody with an enzyme such as papain or pepsin. Alternatively, a gene encoding an antibody fragment may be constructed, inserted into an expression vector, and expressed in an appropriate host cell (see, e.g., Co et al., J Immunol 152: 2968-76 (1994); Better and Horwitz, Methods Enzymol 178: 476-96 (1989); Pluckthun and Skerra, Methods Enzymol 178: 497-515 (1989); Lamoyi, Methods Enzymol 121: 652-63 (1986); Rousseaux et al., Methods Enzymol 121: 663-9 (1986); Bird and Walker, Trends Biotechnol 9: 132-7 (1991)).

Antibodies may be modified by conjugation with various molecules such as polyethyleneglycol (PEG). The present invention provides such modified antibodies. Modified antibodies can be obtained by chemically modifying the antibodies. These modification methods are conventional in the art.

Alternatively, the antibodies of the present invention can be obtained as chimeric antibodies of a non-human antibody-derived variable region and a human antibody-derived constant region, or as humanized antibodies comprising a non-human antibody-derived complementarity determining region (CDR) and a human antibody-derived framework region (FR) and constant region. Such antibodies can be prepared according to known techniques. Humanization can be carried out by substituting a human antibody sequence(s) with a corresponding non-human antibody CDR sequence(s) (see, e.g., Verhoeyen et al., Science 239: 1534-6 (1988)). Thus, such humanized antibodies are chimeric antibodies in which the substantially less than an intact human variable domain has been substituted with a corresponding sequence from a non-human species.

Intact human antibodies comprising a human variable region in addition to the human framework and constant regions can also be used. Such antibodies can be generated using various techniques known in the art. For example, in vitro methods include use of recombinant libraries of human antibody fragments presented on bacteriophages (for example, Hoogenboom & Winter, J. Mol. Biol. 227: 381 (1991)). Similarly, human antibodies can also be generated by introducing human immunoglobulin gene loci into transgenic animals, for example, mice, in which the endogenous immunoglobulin genes have been partially or completely inactivated. This approach is described in, for example, U.S. Pat. Nos. 6,150,584, 5,545,807, 5,545,806, 5,569,825, 5,625,126, 5,633,425 and 5,661,016.

Antibodies obtained as described above may be purified to homogeneity. For example, antibody separation and purification can be performed according to separation methods and purification methods used for general proteins. For example, an antibody can be separated and isolated by appropriately selecting and combining use of column chromatographies such as affinity chromatography, filter, ultrafiltration, salting-out, dialysis, SDS-polyacrylamide gel electrophoresis and isoelectric focusing electrophoresis (Antibodies: A Laboratory Manual. Ed Harlow and David Lane, Cold Spring Harbor Laboratory (1988)), but are not limited thereto. Protein A column and protein G column can be used as the affinity column. Exemplary protein A columns to be used include, for example, Hyper D, POROS and Sepharose F. F. (Pharmacia).

Besides affinity chromatography, exemplary chromatography includes, for example, ion-exchange chromatography, hydrophobic chromatography, gel filtration, reversed-phase chromatography, adsorption chromatography and such (Strategies for Protein Purification and Characterization: A Laboratory Course Manual. Ed Daniel R. Marshak et al., Cold Spring Harbor Laboratory Press (1996)). The chromatography procedures can be carried out by liquid-phase chromatography such as HPLC and FPLC.

The antigen-binding activity of an antibody of the present invention can be measured, for example, by using absorbance measurement, enzyme-linked immunosorbent assay (ELISA), enzyme immunoassay (EIA), radioimmunoassay (RIA), and/or immunofluorescence (IF). In the case of ELISA, an antibody of the present invention is immobilized onto a plate, a peptide of the present invention is applied to the plate, and then a sample containing the desired antibody, such as culture supernatant of antibody-producing cells or purified antibodies, is applied. Next, a secondary antibody that recognizes the primary antibody and is labelled with an enzyme such as alkaline phosphatase is applied and the plate is incubated. Then, after washing, an enzyme substrate such as p-nitrophenyl phosphate is applied to the plate, and the antigen-binding activity of the sample is evaluated by measuring absorbance. To assess the binding activity of an antibody, peptide fragments such as C-terminal or N-terminal fragments may be used as an antigen. BIAcore (Pharmacia) may be used to evaluate the activity of an antibody of the present invention.

It is possible to detect or measure a peptide of the present invention using the above methods, by exposing an antibody of the present invention to a sample assumed to contain the peptide of the present invention, and detecting or measuring an immune complex formed between the antibody and the peptide.

For example, an antibody of the present invention can be used to detect a peptide of the present invention present in the blood sample (for example, serum sample) of a subject. Alternatively, an antibody of the present invention present in the blood sample (for example, serum sample) of a subject can also be detected using a peptide of the present invention. The result of measuring a peptide of the present invention or an antibody of the present invention in the blood sample of a subject can be utilized to the subject selection for administration of the pharmaceutical compositions of the present invention or monitoring of the efficacy of the pharmaceutical compositions of the present invention.

XIII. Vectors and Host Cells

The present invention provides vectors comprising a polynucleotide encoding a peptide of the present invention and host cells introduced with the vectors. A vector of the present invention may be used to keep a polynucleotide of the present invention in a host cell, to express a peptide of the present invention in a host cell, or to administer a polynucleotide of the present invention for gene therapy.

When *E. coli* is a host cell and a vector is amplified and produced in a large amount in *E. coli* (for example, JM109, DH5-alpha, HB101 or XL1-Blue), the vector needs to have a "replication origin" for amplification in *E. coli* and a marker gene for selection of transformed *E. coli* (for example, a drug resistance gene selected by a drug such as ampicillin, tetracycline, kanamycin, chloramphenicol). For example, the M13-series vectors, pUC-series vectors, pBR322, pBluescript, pCR-Script and such can be used. In addition, pGEM-T, pDIRECT and pT7 can be used for cloning as well as the above vectors. When a vector is used in the production of a peptide of the present invention, an expression vector can be used. For example, an expression vector for expression in *E. coli* needs to have the above features for amplification in *E. coli*. When *E. coli* such as JM109, DH5-alpha, HB101 or XL1-Blue are used as a host cell, the vector needs to have a promoter, for example, lacZ promoter (Ward et al., Nature 341: 544-6 (1989); FASEB J 6: 2422-7 (1989)), araB promoter (Better et al., Science 240: 1041-3 (1988)), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may contain a signal sequence for peptide secretion. An exemplary signal sequence that directs the peptide to be secreted to the periplasm of the *E. coli* is the pelB signal sequence (Lei et al., J Bacteriol 169: 4379 (1987)). Means for introducing the vectors into the target host cells include, for example, the calcium chloride method and the electroporation method.

In addition to *E. coli*, for example, expression vectors derived from mammals (for example, pcDNA3 (Invitrogen) and pEGF-BOS (Nucleic Acids Res 18(17): 5322 (1990)), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vectors derived from yeast (e.g., "*Pichia* Expression Kit" (Invitrogen), pNV11, SP-QO1) and expression vectors derived from *Bacillus subtilis* (e.g., pPL608, pKTH50) can be used for producing the polypeptide of the present invention.

In order to express the vector in animal cells such as CHO, COS or NIH3T3 cells, the vector needs to carry a promoter necessary for expression in such cells, for example, the SV40 promoter (Mulligan et al., Nature 277: 108 (1979)), the MMLV-LTR promoter, the EF1-alpha promoter (Mizushima et al., Nucleic Acids Res 18: 5322 (1990)), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

III. Method of Detecting a History of SARS-CoV-2 Infection

Detection of a Cellular Response Due to SARS-CoV-2 Infection in Subjects

Significant IFN-γ production was shown in T cells stimulated with a particular SARS-CoV-2 protein-derived peptide (SEQ ID NO: 1, 4, 5, 7, 9, 10 or 13). Thus, CTL clones specific to any of those peptides were established and TCR sequence analysis was performed to identify the amino acid sequences of CDR3 of TCRs expressed by the CTL clones specific to the SARS-CoV-2 protein-derived peptide (Table 3). When TCRα or TCRβ or a pair of them comprising CDR3 of an amino acid sequence shown in Table 3 is detected in a subject, it means that a peptide-specific CTL response has been induced in the subject. Accordingly, an increase in a particular pair of genes in a T cell population stimulated with a SARS-CoV-2 protein-derived peptide may be useful as a surrogate marker for detecting a CTL response in a subject after stimulation. When such a CTL response is confirmed, it means that the subject was previously infected with SARS-CoV-2. In the context of the present invention, a "peptide-specific CTL response" is to be understood as meaning that a TCR formed by a pair of α and β subunits specifically recognizes a complex formed by a peptide of the present invention and an HLA molecule. As discussed above, the CTL-inducing ability of the peptides defined by the specific sequences of the present invention can be maintained even after amino acid modifications. Accordingly, in addition to stimulation with a specific peptide, even when a T cell is induced by a variant peptide, its antigen specificity is considered "peptide-specific" as long as its TCR specifically recognizes such a complex formed by the original peptide.

In a preferred embodiment, the present invention provides methods for detecting a T cell response due to SARS-CoV-2 infection in a subject, the method comprising the steps of:

(a) providing a sample obtained from a subject, wherein the sample comprises a T cell;

(b) detecting the presence of a T cell specific to a SARS-CoV-2 protein-derived peptide that has been induced by SARS-CoV-2 infection in the sample; and (c) when the presence of the T cell is shown in (b) using a T cell receptor (TCR) as an index, the probability of previous SARS-CoV-2 infection is indicated.

The probability of previous SARS-CoV-2 infection can be determined, for example, by detecting one or both of the α and β subunits comprising CDR3 which consists of an amino acid sequence shown in Table 3.

Specifically, for example, PBMCs are collected from the blood of a subject (HLA-A*24:02-positive) whose previous history of SARS-CoV-2 infection is to be examined, and TCR repertoire is analyzed. On the other hand, for example, an individual not infected with SARS-CoV-2 (HLA-A*24:02-positive) is used as a comparative control, repertoire analysis result is similarly obtained for its PBMCs, and the two are compared; when a greater number of T cells specific to SARS-CoV-2 protein-derived peptides are detected than in the comparative control, the subject is indicated to have a previous history of SARS-CoV-2 infection. As the comparative control, for example, human PBMCs before SARS-CoV-2 infection of humans was reported can be used. Specifically, human PBMCs prepared from the blood collected before December 2019 can be used as the comparative control, but it is not limited thereto.

In the present invention, any biological sample obtained from a subject can be used to detect a T cell response as long as the sample comprises T cells. For example, blood or a blood-derived sample can be used as a biological sample for the present invention. In the present invention, a blood-derived sample comprises a cell population comprising T cells. Methods for obtaining a cell population comprising T cells are well known to those skilled in the art.

A T cell receptor (TCR) consists of V, D, J and C genes.

It is considered that as much as 10 raised to the power of 18 of diversity is generated in TCRs by rearrangements of the V and J genes and further by insertions and deletions of nucleotides randomly occurring between the V-D-J genes (CDR3). Thus, there are T cells expressing various TCRs in the human body.

Examining TCR diversity (how often and what TCRs are detected) in a certain T cell population is called TCR repertoire analysis.

When TCR repertoire analysis is performed, cDNAs in which an adaptor has been added to the 5' end are synthesized from RNAs derived from a T cell population in order to amplify various TCR genes by a PCR method without bias. A next-generation sequencer (Next-Generation Sequencing: NGS) is used to determine the nucleotide sequences of a large amount of DNA fragments (sequence library) obtained using an adaptor-specific forward primer and a TCR-α- or TCR-β-specific reverse primer.

A next-generation sequencer is a device that has the ability to determine the nucleotide sequences of millions of DNA fragments in parallel. In TCR repertoire analysis, it is necessary to determine long nucleotide sequences spanning the V, D, J and C genes constituting TCRs. Thus, among next-generation sequencers, MiSeq (Illumina), which excels in long-read analysis (determination of nucleotide sequences of approximately 300 bp), is often used.

The detection frequency of each CDR3 in a T cell population constituting a sample can be easily known by comprehensively analyzing the nucleotide sequences of mRNAs encoding TCRs contained in the sample (it practically means analyzing the nucleotide sequences of cDNAs reverse-transcribed from the nucleotide sequences of such mRNAs). Examples of the nucleotide sequences of primers useful for determining the nucleotide sequences of CDR3 are shown below:

```
Forward primer (adaptor sequence common to TCR-α
and TCR-β, SEQ ID NO: 46):
5'-GTCTCGTGGGCTCGGAGATGTGTATAAGAGACAGTATCAACGCAGA
GTGGCCAT-3'

Reverse primer (for TCR-α, SEQ ID NO: 48):
5'-TCGTCGGCAGCGTCAGATGTGTATAAGAGACAGDBDHHCAGGGTCA
GGGTTCTGGATA-3'

Reverse primer (for TCR-β, SEQ ID NO: 47):
5'-TCGTCGGCAGCGTCAGATGTGTATAAGAGACAGDVHDVTCTGATGG
CTCAAACACAGC-3'
```

More specifically, the present invention provides methods of detecting a T cell response, the method comprising the steps of:

(a) extracting gDNA from PBMCs derived from a subject or synthesizing cDNAs by using RNAs extracted from the PBMCs as templates;

(b) determining the frequency of each amino acid sequence in TCRs by decoding of TCRα gene sequences and TCRβ gene sequences from the gDNA or cDNAs; and (c) when a TCR responsive to a SARS-CoV-2-derived peptide is detected in the amino acid sequences of TCRs determined in (b), the presence of SARS-CoV-2-specific T cells induced by infection is indicated.

In a certain embodiment of the present invention, the detection frequency of a TCR responsive to a SARS-CoV-2-derived peptide can be compared to that in a comparative control. For example, a TCR repertoire analysis result of PBMCs derived from individuals not infected with SARS-CoV-2 can be used as a comparative control. Accordingly, when the detection frequency of a TCR responsive to a SARS-CoV-2-derived peptide is greater than that in a comparative control, it indicates that a SARS-CoV-2-specific T cell response has been induced.

Prior to the methods of the present invention, the step of collecting peripheral blood lymphocytes (PBMCs) from the subject can be comprised. By repeating the series of analyses over time, changes in the frequency of a TCR responsive to a SARS-CoV-2-derived peptide can be traced. For example, changes in the frequency of a TCR responsive to a SARS-CoV-2-derived peptide of the present invention can be traced after inoculation with the SARS-CoV-2-derived peptide or SARS-CoV-2 infection to evaluate the effect of enhancing an immune response.

Accordingly, the methods of detecting a T cell response of the present invention allow knowing the results of inducing an immune response in a subject to whom a peptide of the present invention has been administered. More specifically, the present invention provides methods of detecting a T cell response, the method comprising administering a peptide of the present invention to a subject and detecting a T cell response in the subject after the administration. Moreover, in the present invention, a subject in whom a sufficient T cell response has not been detected can be additionally selected as a target for booster inoculation with the peptide of the present invention.

The embodiments of the present invention are exemplified below based on the above explanation; however, the present invention is not limited to these embodiments.

[1] A peptide of less than 15 amino acids having cytotoxic T cell (CTL)-inducing ability, which comprises the amino acid sequence selected from the group of:
 (a) the amino acid sequence selected from the group consisting of SEQ ID NOs: 1, 2, 3, 4, 5, 7, 9, 10, 11, 12, 13 and 15; and
 (b) the amino acid sequence in which one, two or several amino acids are substituted, deleted, inserted and/or added to the amino acid sequence selected from the group consisting of SEQ ID NOs: 1, 2, 3, 4, 5, 7, 9, 10, 11, 12, 13 and 15.

[2] The peptide of [1], which has either or both of features below to the amino acid sequence selected from the group consisting of 1, 2, 3, 4, 5, 7, 9, 10, 11, 12, 13 and 15:
 (a) the second amino acid from the N terminus is substituted with an amino acid selected from the group consisting of phenylalanine, tyrosine, methionine and tryptophan; and
 (b) the C-terminal amino acid is substituted with an amino acid selected from the group consisting of phenylalanine, leucine, isoleucine, tryptophan and methionine.

[3] The peptide of [1], which has either or both of features below to the amino acid sequence selected from the group consisting of SEQ ID NOs: 1, 2, 4, 7, 10, 12 and 13:
 (a) the second amino acid from the N terminus is substituted with an amino acid selected from the group consisting of leucine and methionine; and
 (b) the C-terminal amino acid is substituted with an amino acid selected from the group consisting of valine and leucine.

[4] The peptide of [1], which consists of the amino acid sequence selected from the group consisting of SEQ ID NOs: 1, 2, 3, 4, 5, 7, 9, 10, 11, 12, 13 and 15.

[5] A polynucleotide, which encodes the peptide of any one of [1] to [4].

[6] A composition comprising a pharmaceutically acceptable carrier and at least one active ingredient selected from the group consisting of (a) to (e) below:
 (a) one or more types of peptides of any one of [1] to [4];
 (b) one or more types of polynucleotides encoding the peptide(s) of any one of [1] to [4] in an expressible form;
 (c) an antigen-presenting cell (APC) that presents on its cell surface a complex of the peptide of any one of [1] to [4] and an HLA antigen;
 (d) an exosome that presents on its cell surface a complex of the peptide of any one of [1] to [4] and an HLA antigen; and
 (e) a CTL that targets the peptide of any one of [1] to [4].

[7] The composition of [6], which is a composition for inducing a CTL(s), wherein the active ingredient is at least one ingredient selected from the group consisting of (a) to (d) below:
 (a) one or more types of peptides of any one of [1] to [4];
 (b) one or more types of polynucleotides encoding the peptide(s) of any one of [1] to [4] in an expressible form;
 (c) an antigen-presenting cell (APC) that presents on its cell surface a complex of the peptide of any one of [1] to [4] and an HLA antigen; and
 (d) an exosome that presents on its cell surface a complex of the peptide of any one of [1] to [4] and an HLA antigen.

[8] The composition of [6], which is a pharmaceutical composition.

[9] The composition of [8], which is a pharmaceutical composition for one or more uses selected from the group consisting of (i) treatment of coronavirus infectious disease, (ii) prevention (prophylaxis) of coronavirus infectious disease and (iii) suppression of aggravation of coronavirus infectious disease.

[10] The composition of [8], which is for inducing an immune response against coronavirus infection.

[11] The composition of [9] or [10], wherein coronavirus of the coronavirus infectious disease is selected from the group consisting of SARS-CoV-2, MERS-CoV and SARS-CoV.

[12] The composition of any one of [6] to [11], which is formulated for administration to a subject positive for HLA-A24 or HLA-A02.

[13] A method of inducing an APC(s) having CTL-inducing ability, which comprises a step selected from the group consisting of (a) and (b) below:
 (a) contacting an APC(s) with the peptide of any one of [1] to [4] in vitro, ex vivo or in vivo; and
 (b) introducing a polynucleotide encoding the peptide of any one of [1] to [4] into an APC(s).

[14] A method of inducing a CTL(s), which comprises a step selected from the group consisting of (a) to (c) below:
 (a) co-culturing a CD8-positive T cell(s) with an APC(s) that presents on its surface a complex of an HLA antigen and the peptide of any one of [1] to [4];
 (b) co-culturing a CD8-positive T cell(s) with an exosome(s) that presents on its surface a complex of an HLA antigen and the peptide of any one of [1] to [4]; and
 (c) introducing into a CD8-positive T cell(s) a polynucleotide encoding each subunit of a T cell receptor (TCR) capable of binding to the peptide of any one of [1] to [4] presented by an HLA antigen on a cell surface.

[15] An APC that presents on its surface a complex of an HLA antigen and the peptide of any one of [1] to [4].

[16] The APC of [15], which is induced by the method of [13].

[17] A CTL that targets the peptide of any one of [1] to [4].

[18] The CTL of [17], which is induced by the method of [14].

[19] A method of inducing an immune response against coronavirus infection, which comprises administering to a subject a composition comprising at least one ingredient selected from the group consisting of (a) to (e) below:

(a) one or more types of peptides of any one of [1] to [4];
(b) one or more types of polynucleotides encoding the peptide(s) of any one of [1] to [4] in an expressible form;
(c) an antigen-presenting cell (APC) that presents on its cell surface a complex of the peptide of any one of [1] to [4] and an HLA antigen;
(d) an exosome that presents on its cell surface a complex of the peptide of any one of [1] to [4] and an HLA antigen; and
(e) a CTL that targets the peptide of any one of [1] to [4].

[20] A method of any one purpose selected from treatment of, prevention of, and suppression of aggravation of coronavirus infectious disease, or multiple purposes thereof, which comprises administering to a subject at least one ingredient selected from the group consisting of (a) to (e) below:
(a) one or more types of peptides of any one of [1] to [4];
(b) one or more types of polynucleotides encoding the peptide(s) of any one of [1] to [4] in an expressible form;
(c) an antigen-presenting cell (APC) that presents on its cell surface a complex of the peptide of any one of [1] to [4] and an HLA antigen;
(d) an exosome that presents on its cell surface a complex of the peptide of any one of [1] to [4] and an HLA antigen; and
(e) a CTL that targets the peptide of any one of [1] to [4].

[21] An antibody that binds to the peptide of any one of [1] to [4].

[22] A method of screening for a peptide having CTL-inducing ability, which comprises the steps of
(a) generating candidate sequences consisting of an amino acid sequence in which one, two or several amino acid residues are substituted, deleted, inserted and/or added to an original amino acid sequence consisting of the amino acid sequence selected from among SEQ ID NOs: 1, 2, 3, 4, 5, 7, 9, 10, 11, 12, 13 and 15;
(b) selecting from among the candidate sequences generated in (a), a candidate sequence that does not have significant homology (sequence identity) with any known human gene product;
(c) contacting an APC(s) with a peptide consisting of the candidate sequence selected in (b);
(d) contacting the APC(s) of (c) with a CD8-positive T cell(s); and
(e) selecting a peptide having an equal to or higher CTL-inducing ability than that of a peptide consisting of the original amino acid sequence.

[23] Use of at least one ingredient selected from the group consisting of (a) to (e) below in the manufacture of a composition for inducing an immune response against coronavirus infection:
(a) one or more types of peptides of any one of [1] to [4];
(b) one or more types of polynucleotides encoding the peptide(s) of any one of [1] to [4] in an expressible form;
(c) an antigen-presenting cell (APC) that presents on its cell surface a complex of the peptide of any one of [1] to [4] and an HLA antigen;

(d) an exosome that presents on its cell surface a complex of the peptide of any one of [1] to [4] and an HLA antigen; and
(e) a CTL that targets the peptide of any one of [1] to [4].

[24] Use of at least one active ingredient selected from the group consisting of (a) to (e) below in the manufacture of a pharmaceutical composition for any one purpose selected from treatment of, prevention of, and suppression of aggravation of coronavirus infectious disease, or multiple purposes thereof:
(a) one or more types of peptides of any one of [1] to [4];
(b) one or more types of polynucleotides encoding the peptide(s) of any one of [1] to [4] in an expressible form;
(c) an antigen-presenting cell (APC) that presents on its cell surface a complex of the peptide of any one of [1] to [4] and an HLA antigen;
(d) an exosome that presents on its cell surface a complex of the peptide of any one of [1] to [4] and an HLA antigen; and
(e) a CTL that targets the peptide of any one of [1] to [4].

[25] Use of at least one active ingredient selected from the group consisting of (a) to (e) below for inducing an immune response against coronavirus infection:
(a) one or more types of peptides of any one of [1] to [4];
(b) one or more types of polynucleotides encoding the peptide(s) of any one of [1] to [4] in an expressible form;
(c) an antigen-presenting cell (APC) that presents on its cell surface a complex of the peptide of any one of [1] to [4] and an HLA antigen;
(d) an exosome that presents on its cell surface a complex of the peptide of any one of [1] to [4] and an HLA antigen; and
(e) a CTL that targets the peptide of any one of [1] to [4].

[26] Use of at least one active ingredient selected from the group consisting of (a) to (e) below for any one purpose selected from treatment of, prevention of, and suppression of aggravation of coronavirus infectious disease, or multiple purposes thereof:
(a) one or more types of peptides of any one of [1] to [4];
(b) one or more types of polynucleotides encoding the peptide(s) of any one of [1] to [4] in an expressible form;
(c) an antigen-presenting cell (APC) that presents on its cell surface a complex of the peptide of any one of [1] to [4] and an HLA antigen;
(d) an exosome that presents on its cell surface a complex of the peptide of any one of [1] to [4] and an HLA antigen; and
(e) a CTL that targets the peptide of any one of [1] to [4].

[27] A method of inducing cytotoxic activity against a coronavirus-infected cell(s), which comprises a step of administering to a subject at least one active ingredient selected from the group consisting of (a) to (e) below:
(a) one or more types of peptides of any one of [1] to [4];
(b) one or more types of polynucleotides encoding the peptide(s) of any one of [1] to [4] in an expressible form;

(c) an antigen-presenting cell (APC) that presents on its cell surface a complex of the peptide of any one of [1] to [4] and an HLA antigen;
(d) an exosome that presents on its cell surface a complex of the peptide of any one of [1] to [4] and an HLA antigen; and
(e) a CTL that targets the peptide of any one of [1] to [4].

[28] A freeze-dried formulation comprising one or more types of peptides of any one of [1] to [4].

[29] A pharmaceutical composition, which is prepared by a method that comprises dissolving one or more types of peptides of any one of [1] to [4] in a water-soluble carrier, and performing filtration sterilization.

[30] A filtration-sterilized aqueous solution, which is an aqueous solution that comprises one or more types of peptides of any one of [1] to [4] and a water-soluble carrier.

[31] An emulsion comprising one or more types of peptides of any one of [1] to [4], a water-soluble carrier and an oil adjuvant.

[32] A kit comprising a container that houses the pharmaceutical composition of any one of [8] to [12] and a container that houses an adjuvant.

[33] A kit comprising a container that stores a freeze-dried formulation comprising the peptide of any one of [1] to [4], a container that stores an adjuvant, and a container that stores a re-dissolving solution for the freeze-dried formulation.

[34] A kit comprising a container that houses the composition of any one of [6] to [12] and a container that houses an adjuvant.

[35] AT cell receptor α chain comprising CDR3 specified by any amino acid sequence selected from the group consisting of SEQ ID NOs: 32, 34, 36, 38 and 40, or CDR3 functionally equivalent thereto.

[36] AT cell receptor β chain comprising CDR3 specified by any amino acid sequence selected from the group consisting of SEQ ID NOs: 33, 35, 37, 39 and 41, or CDR3 functionally equivalent thereto.

[37] AT cell receptor consisting of a combination of any one of the T cell receptor α chain of [35] and any one of the T cell receptor β chain of [36].

[38] The T cell receptor of [37], wherein the amino acid sequences of CDR3 of the T cell receptor α chain and β chain are any one of the following combinations:

CDR3 of T cell receptor α chain CDR3 of T cell receptor β chain
SEQ ID NO: 32 SEQ ID NO: 33;
SEQ ID NO: 34 SEQ ID NO: 35;
SEQ ID NO: 36 SEQ ID NO: 37,
SEQ ID NO: 38 SEQ ID NO: 39; and
SEQ ID NO: 40 SEQ ID NO: 41.

[39] A polynucleotide encoding any one of the T cell receptor α chain of [35] and any one of the T cell receptor β chain of [36].

[40] A TCR which recognizes the peptide any one of [1]-[4] presented on an APC by an HLA antigen.

[41] A method of determining a history of SARS-CoV-2 infection, the method comprising the steps of:
(a) extracting gDNA from PBMC derived from a subject or synthesizing cDNAs using RNAs extracted from the PBMC as templates;
(b) determining TCR repertoire by comprehensive decoding of TCRα gene sequences and TCRβ gene sequences from the gDNA or cDNAs with a next-generation sequencer (NGS); and
(c) evaluating the presence of SARS-CoV-2-specific T cell induced by the infection by profiling the TCR repertoire using a TCR responsive to a SARS-CoV-2-derived peptide as an index.

[42] The method of [41], wherein the TCR responsive to a SARS-CoV-2-derived peptide is the TCR of [40].

The present invention is explained herein in detail with reference to its specific embodiments. However, it should be understood that the above explanation is in fact an illustrative and explanatory explanation, and is intended to explain the present invention and preferred embodiments thereof. Through routine experimentation, one skilled in the art will readily recognize that various changes and modifications can be made therein without departing from the spirit and scope of the present invention. Thus, the present invention is not confined to the above explanation, but is intended to be defined by the appended claims and equivalents thereto.

Hereinbelow, the present invention is described in more detail with reference to the Examples. Nevertheless, while the following materials, method and Examples may serve to assist one of ordinary skill in making and using certain embodiments of the present invention, there are only intended to illustrate aspects of the present invention and thus in no way to limit the scope of the present invention. One of ordinary skill in the art can use methods and materials similar or equivalent to those described herein in the practice or testing of the present invention.

Example 1

Materials and Methods

Cell Lines

TISI cells (HLA-A*24:02/−), human lymphoblastoid cell line, were purchased from the International Histocompatibility Working Group. T2 cells (HLA-A*02:01/−), human lymphoblast cell line, were purchased from ATCC.

Selection of Peptides Derived from SARS-CoV-2

SARS-CoV-2 protein-derived 9mer and 10mer peptides that would be expected to bind to HLA-A*24:02 were determined using “NetMHC4.0” binding prediction server (http://www.cbs.dtu.dk/services/NetMHC/) (Nielsen M et al., Protein Sci 2003, 12(5): 1007-1017; Andreatta M et al., Bioinformatics 2016, 32(4): 511-517). Of these, peptides commonly found in SARS-CoV Tor2 (GenBank accession number AY274119), SARS-CoV BJO1 (GenBank accession number AY278488) and SARS-CoV GZ02 (GenBank accession number AY390556), and also in MERS-CoV (GenBank accession number JX869059) were selected as candidate epitopes (Kiyotani K et al., J Hum Genet 2020, 65(7): 569-575).

Peptide Synthesis

The peptides were synthesized by Cosmo Bio Co., Ltd. (Tokyo, Japan) according to solid synthesis method and purified by reversed-phase high-performance liquid chromatography (HPLC). The quality (purity: 90% or higher) of the peptides was guaranteed by HPLC and mass spectrometry analysis. Peptides were dissolved in dimethyl sulfoxide (final concentration: 20 mg/mL) and stored at −80° C.

In Vitro CTL Induction

Monocyte-derived dendritic cells (DCs) were used as antigen-presenting cells to induce cytotoxic T cells (CTLs) specific to a peptide presented on a human leukocyte antigen (HLA). DCs were prepared in vitro as has already been reported in the literature (Nakahara S et al., Cancer Res 2003, 63(14): 4112-4118). Specifically, peripheral blood mononuclear cells (PBMCs) collected from healthy volunteers (HLA-A*24:02- or HLA-A*02:01-positive) were seeded onto a tissue culture dish (Corning) to allow adhesion of monocytes in PBMCs to the dish. The cells were cultured in the presence of 1000 IU/mL granulocyte-macrophage colony-stimulating factor (R&D System) and 1000 IU/mL interleukin (IL)-4 (R&D System) for seven days. AIM-V medium (Invitrogen) containing inactivated Type AB serum (MP Biomedicals) (2% ABS/AIM-V medium) was used as a medium. DCs differentiated from monocytes by cytokine and autologous CD8-positive T cells obtained by using CD8-Positive Isolation Kit (Invitrogen) were mixed at 1:20 ratio ($1.5\times10^4$ DC cells and $3\times10^5$ CD8-positive T cells) and cultured in a 48-well plate (Corning). Peptides were further added thereto (peptide final concentration: 20 μg/ml). Volume of 2% ABS/AIM-V medium per well was 0.5 ml, and IL-7 (R&D System) and IL-21 (Cell Genix) were added thereto (final concentrations: IL-7, 10 ng/ml; IL-21, 30 ng/ml). Three days after the start of culture, DCs and peptide were again added thereto (peptide final concentration: 20 μg/ml). DCs were prepared at time of use by the same way as described above. Seven days after the start of culture, IL-2 (Novartis), IL-7 and IL-15 (Novoprotein) were added thereto (final concentrations: IL-2, 48 IU/ml; IL7, 5 ng/ml; and IL-15, ng/ml) (Wolfl M et al., Nat Protoc 2014, 9(4): 950-966). On day 9 (after the two DC stimulations) and thereafter, IFN-γ production for TISI or T2 cells pulsed with the peptide was confirmed by an enzyme-linked immunospot (ELISPOT) assay.

CTL Proliferation Procedure

CTLs were proliferated using a method similar to that reported by Riddell et al. (Walter E A et al., N Engl J Med 1995, 333(16): 1038-1044; Riddell S R et al., Nat Med 1996, 2(2): 216-223). In tissue culture flasks (FALCON), CTLs were cultured in 5% ABS/AIM-V medium (culture medium volume: 25 ml/flask) along with two human B lymphoblastoid cell lines ($5\times10^6$ cells each) treated with mitomycin C and an anti-CD3 antibody (BD biosciences, final concentration: 40 ng/ml). On the day following the start of the culture, IL-2 was added to the culture (final IL-2 concentration: 120 IU/ml). On days 5, 8, and 11, the medium was replaced with 5% ABS/AIM-V medium containing 60 IU/ml IL-2 (final IL-2 concentration: 30 IU/ml) (Yoshimura S et al., PLoS One 2014, 9(1): e85267).

Confirmation of IFN-γ Production

To confirm peptide-specific IFN-γ production of CTLs induced using the peptide, IFN-γ ELISPOT assay and IFN-γ ELISA were performed. Peptide-pulsed TISI cells or T2 cells were prepared as target cells. IFN-γ ELISPOT assay and IFN-γ ELISA were performed according to the procedure recommended by the assay kit manufacturer.

Results

Selection of HLA-A*24:02-Binding Peptides Derived from SARS-CoV-2 Proteins

Tables 2a and 2b show the 9mer and 10mer peptides derived from SARS-CoV-2 proteins predicted to bind to HLA-A*24:02 by "NetMHC 4.0" in the order of high binding affinity. Peptides that are also commonly found in SARS-CoV and MERS-CoV are shown in Table 2a. Peptides common only to SARS-CoV are listed in Table 2b. A total of 15 peptides were selected as candidate epitope peptides that may have the ability to bind to HLA-A*24:02.

TABLE 2a

SARS CoV-2 Protein-derived Peptides Predicted to Bind to HLA-A*24:02 (Common to SARS-CoV and MERS-CoV)

| Peptide | Protein | Position | Length | Amino Acid Sequence | Binding Affinity (nM) | SEQ ID NO |
|---|---|---|---|---|---|---|
| 1 | ORF1ab | 5080 | 9 | AYANSVFNI | 56 | 1 |
| 2 | ORF1ab | 5079 | 10 | TAYANSVFNI | 102 | 2 |
| 3 | ORF1ab | 5184 | 9 | VFMSEAKCW | 395 | 3 |

The number in "Position" indicates the number of the first amino acid of the peptide counted from the N terminus of the protein.

Binding affinity (nM) was calculated using "NetMHC4.0".

TABLE 2b

SARS CoV-2 Protein-derived Peptides Predicted to Bind to HLA-A*24:02 (Common Only to SARS-CoV)

| Peptide | Protein | Position | Length | Amino Acid Sequence | Binding Affinity (nM) | SEQ ID NO |
|---|---|---|---|---|---|---|
| 4 | ORF1ab | 4090 | 9 | TYASALWEI | 18 | 4 |
| 5 | S | 897 | 10 | PFAMQMAYRF | 39 | 5 |
| 6 | ORF1ab | 3811 | 10 | YDYLVSTQEF | 41 | 6 |
| 7 | ORF1ab | 2560 | 10 | YYSQLMCQPI | 44 | 7 |
| 8 | ORF1ab | 4628 | 9 | SYYSLLMPI | 46 | 8 |
| 9 | ORF1ab | 6676 | 9 | RYKLEGYAF | 62 | 9 |
| 10 | ORF1ab | 4089 | 10 | FTYASALWEI | 69 | 10 |

TABLE 2b-continued

SARS CoV-2 Protein-derived Peptides Predicted to Bind to HLA-A*24:02 (Common Only to SARS-CoV)

| Peptide | Protein | Position | Length | Amino Acid Sequence | Binding Affinity (nM) | SEQ ID NO |
|---|---|---|---|---|---|---|
| 11 | ORF1ab | 7039 | 10 | SYSLFDMSKF | 85 | 11 |
| 12 | ORF1ab | 4677 | 10 | RYFKYWDQTY | 90 | 12 |
| 13 | M | 54 | 9 | LWLLWPVTL | 108 | 13 |
| 14 | ORF1ab | 4090 | 10 | TYASALWEIQ | 111 | 14 |
| 15 | ORF1ab | 5138 | 10 | YAYLRKHFSM | 115 | 15 |

The number in "Position" indicates the number of the first amino acid of the peptide counted from the N terminus of the protein.

Binding affinity (nM) was calculated using "NetMHC4.0".

Induction of HLA-A*24:02-Restricted CTLs by Peptides Derived from SARS-CoV-2 Proteins Using HLA-A*24:02-positive PBMCs, CTLs specific to peptides derived from SARS-CoV-2 proteins were induced according to the protocol described in "Materials and Methods". Peptide-specific IFN-γ production by the cells was confirmed by an ELISPOT assay (FIG. 1). Peptide-specific IFN-γ production was observed for Peptide 1 (SEQ ID NO: 1), Peptide 2 (SEQ ID NO: 2), Peptide 3 (SEQ ID NO: 3), Peptide 4 (SEQ ID NO: 4), Peptide 5 (SEQ ID NO: 5), Peptide 7 (SEQ ID NO: 7), Peptide 9 (SEQ ID NO: 9), Peptide 10 (SEQ ID NO: 10), Peptide 11 (SEQ ID NO: 11), Peptide 12 (SEQ ID NO: 12), Peptide 13 (SEQ ID NO: 13) and Peptide 15 (SEQ ID NO: 15) (FIG. 1*a*). On the other hand, no peptide-specific IFN-γ production was observed for the other peptides shown in Tables 2a and 2b. For example, peptide-specific IFN-γ production was not found for Peptide 6 (SEQ ID NO: 6) (FIG. 1*b*). Although all the peptides had the possibility to bind to HLA-A*24:02, as a result, 12 peptides were identified that bind to HLA-A*24:02 and have CTL-inducing ability.

Figure 2:
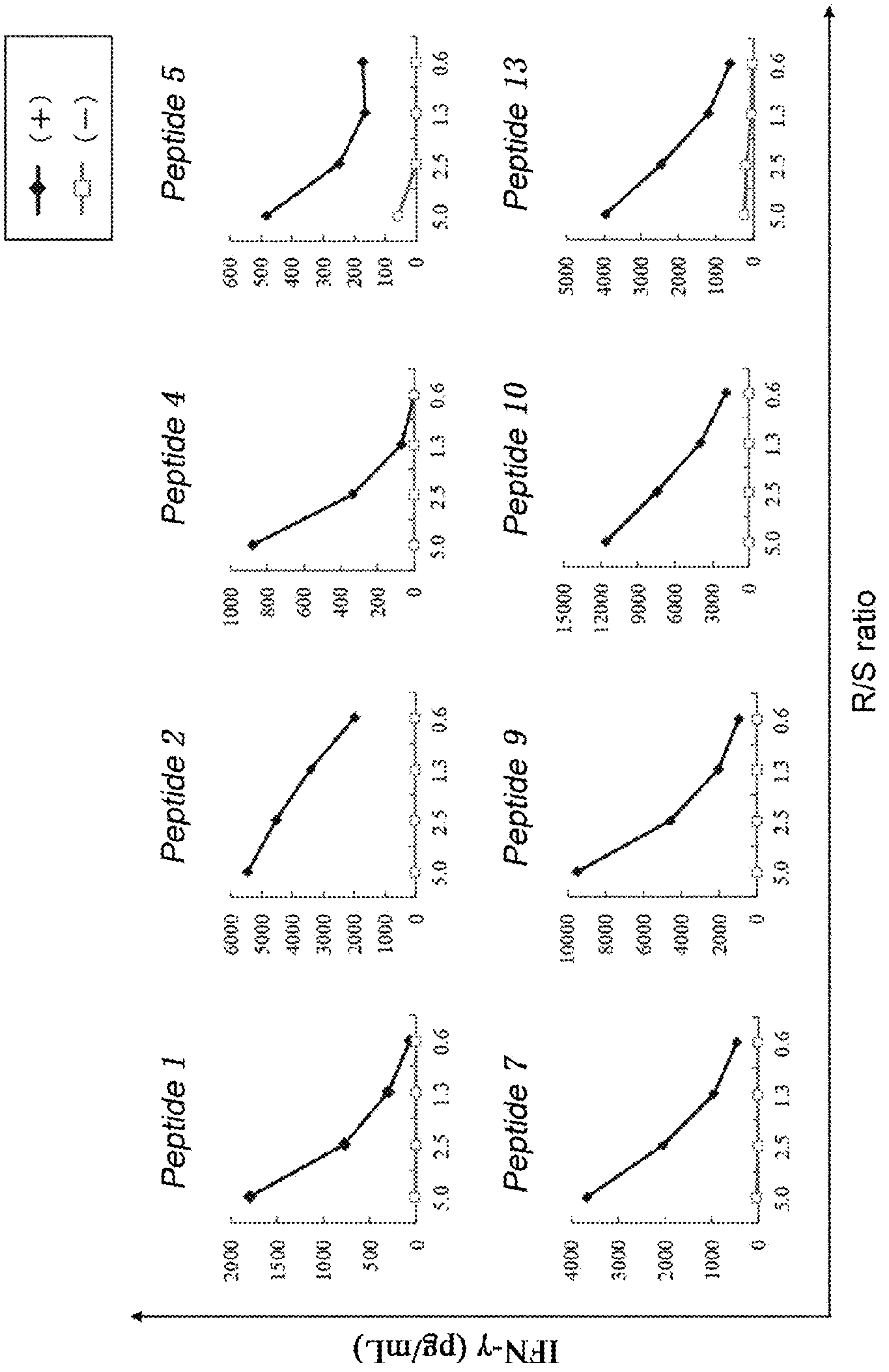
FIG. 2 is composed of line graphs showing the results of measuring IFN-γ produced by cells stimulated with Peptide 1 (SEQ ID NO: 1), Peptide 2 (SEQ ID NO: 2), Peptide 4 (SEQ ID NO: 4), Peptide 5 (SEQ ID NO: 5), Peptide 7 (SEQ ID NO: 7), Peptide 9 (SEQ ID NO: 9), Peptide 10 (SEQ ID NO: 10) or Peptide 13 (SEQ ID NO: 13), using an enzyme-linked immunosorbent assay (ELISA). These results show that after induction with the peptides, HLA-A*24:02-restricted CTL lines were established that produced IFN-γ in a peptide-specific manner. In the figure, "(+)" indicates IFN-γ production of a CTL line for HLA-A*24:02-expressing target cells (TISI cells) pulsed with a peptide of interest, and "(−)" indicates IFN-γ production of a CTL line for TISI cells not pulsed with any peptide. The R/S ratio represents the ratio of the number of CTL line cells, which are responder cells (Responder cells), to the number of target cells (Stimulator cells) that stimulate them.

Establishment of HLA-A*24:02-Restricted CTL Lines Specific to Peptides Derived from SARS-CoV-2 Proteins HLA-A*24:02-restricted CTL lines were established by proliferating the cells that showed IFN-γ production specific to Peptide 1 (SEQ ID NO: 1), Peptide 2 (SEQ ID NO: 2), Peptide 4 (SEQ ID NO: 4), Peptide 5 (SEQ ID NO: 5), Peptide 7 (SEQ ID NO: 7), Peptide 9 (SEQ ID NO: 9), Peptide 10 (SEQ ID NO: 10) or Peptide 13 (SEQ ID NO: 13) in the HLA-A*24:02 restricted-IFN-γ ELISPOT assay. As a result of measuring IFN-γ using ELISA, IFN-γ production by CTL lines for HLA-A*24:02-expressing target cells (TISI cells) pulsed with Peptide 1 (SEQ ID NO: 1), Peptide 2 (SEQ ID NO: 2), Peptide 4 (SEQ ID NO: 4), Peptide 5 (SEQ ID NO: 5), Peptide 7 (SEQ ID NO: 7), Peptide 9 (SEQ ID NO: 9), Peptide 10 (SEQ ID NO: 10) or Peptide 13 (SEQ ID NO: 13) was observed (FIG. 2). This clearly demonstrated that Peptide 1 (SEQ ID NO: 1), Peptide 2 (SEQ ID NO: 2), Peptide 4 (SEQ ID NO: 4), Peptide 5 (SEQ ID NO: 5), Peptide 7 (SEQ ID NO: 7), Peptide 9 (SEQ ID NO: 9), Peptide 10 (SEQ ID NO: 10) and Peptide 13 (SEQ ID NO: 13) bind to HLA-A*24:02 and have CTL-inducing ability.

Induction of HLA-A*02:01-Restricted CTLs by Peptides Derived from SARS-CoV-2 Proteins It was verified whether Peptide 1 (SEQ ID NO: 1), Peptide 2 (SEQ ID NO: 2), Peptide 3 (SEQ ID NO: 3), Peptide 4 (SEQ ID NO: 4), Peptide 5 (SEQ ID NO: 5), Peptide 7 (SEQ ID NO: 7), Peptide 9 (SEQ ID NO: 9), Peptide 10 (SEQ ID NO: 10), Peptide 11 (SEQ ID NO: 11), Peptide 12 (SEQ ID NO: 12), Peptide 13 (SEQ ID NO: 13) and Peptide 15 (SEQ ID NO: 15), which had been confirmed to have the ability to induce HLA-A*24:02-restricted CTLs, have the ability to induce HLA-A*02:01-restricted CTLs.

Figure 3:
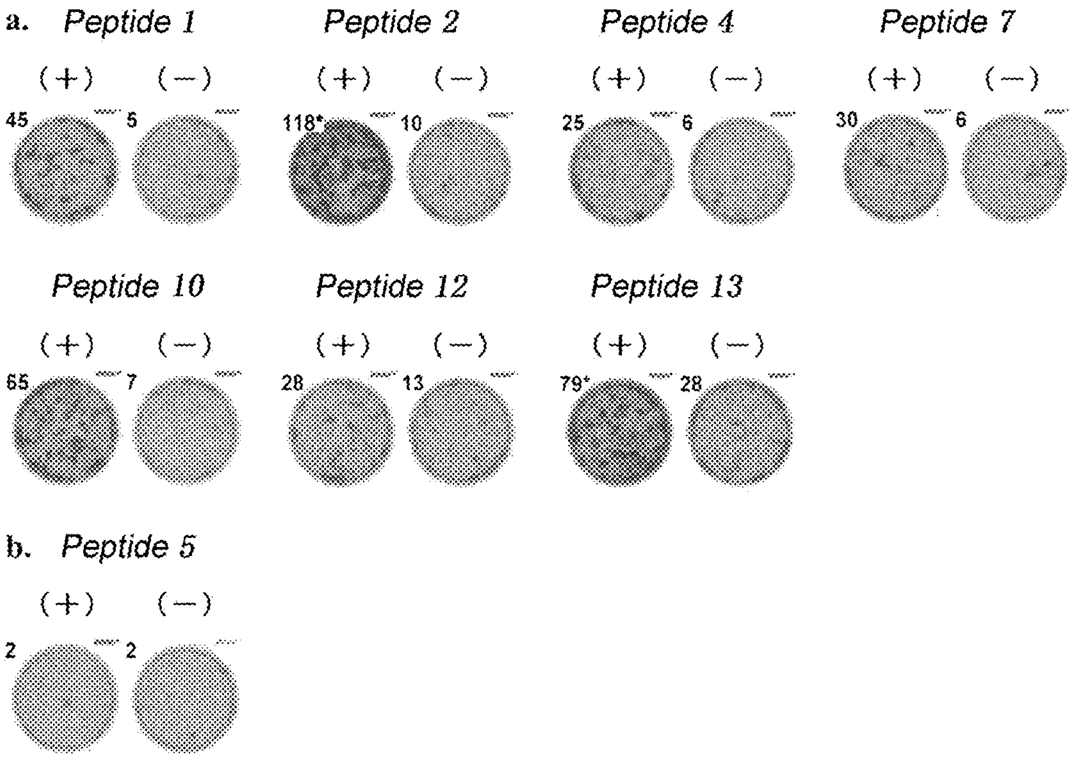
FIG. 3 is composed of images showing the results of IFN-γ enzyme-linked immunospot (ELISPOT) assays performed using cells induced with peptides derived from SARS-CoV-2 proteins. In the figure, "(+)" indicates IFN-γ production for HLA-A*02:01-expressing target cells (T2 cells) pulsed with a peptide of interest, and "(−)" indicates IFN-γ production for T2 cells not pulsed with any peptide (negative control). It can be seen by comparison with the negative control that peptide-specific IFN-γ production was observed for Peptide 1 (SEQ ID NO: 1), Peptide 2 (SEQ ID NO: 2), Peptide 4 (SEQ ID NO: 4), Peptide 7 (SEQ ID NO: 7), Peptide 10 (SEQ ID NO: 10), Peptide 12 (SEQ ID NO: 12) and Peptide 13 (SEQ ID NO: 13) (FIG. 3*a*). On the other hand, Peptide 5 (SEQ ID NO: 5) is shown as an example of typical negative data for which no peptide-specific IFN-γ production was observed (FIG. 3*b*).

Using HLA-A*02:01-positive PBMCs, HLA-A*02:01-restricted CTLs were induced according to the protocol described in "Materials and Methods". Peptide-specific IFN-γ production by the cells was confirmed by an ELISPOT assay (FIG. 3). Peptide-specific IFN-γ production was observed for Peptide 1 (SEQ ID NO: 1), Peptide 2 (SEQ ID NO: 2), Peptide 4 (SEQ ID NO: 4), Peptide 7 (SEQ ID NO: 7), Peptide 10 (SEQ ID NO: 10), Peptide 12 (SEQ ID NO: 12), and Peptide 13 (SEQ ID NO: 13) (FIG. 3*a*). On the other hand, no peptide-specific IFN-γ production was observed for Peptide 3 (SEQ ID NO: 3), Peptide 5 (SEQ ID NO: 5), Peptide 9 (SEQ ID NO: 9), Peptide 11 (SEQ ID NO: 11) and Peptide 15 (SEQ ID NO: 15). As an example, the result of Peptide 5 (SEQ ID NO: 5) is shown (FIG. 3*b*). These results revealed that Peptide 1 (SEQ ID NO: 1), Peptide 2 (SEQ ID NO: 2), Peptide 4 (SEQ ID NO: 4), Peptide 7 (SEQ ID NO: 7), Peptide 10 (SEQ ID NO: 10), Peptide 12 (SEQ ID NO: 12) and Peptide 13 (SEQ ID NO: 13), which have the ability to induce HLA-A*24:02-restricted CTLs, also bind to HLA-A*02:01 and have the ability to induce HLA-A*02:01-restricted CTLs.

Figure 4:
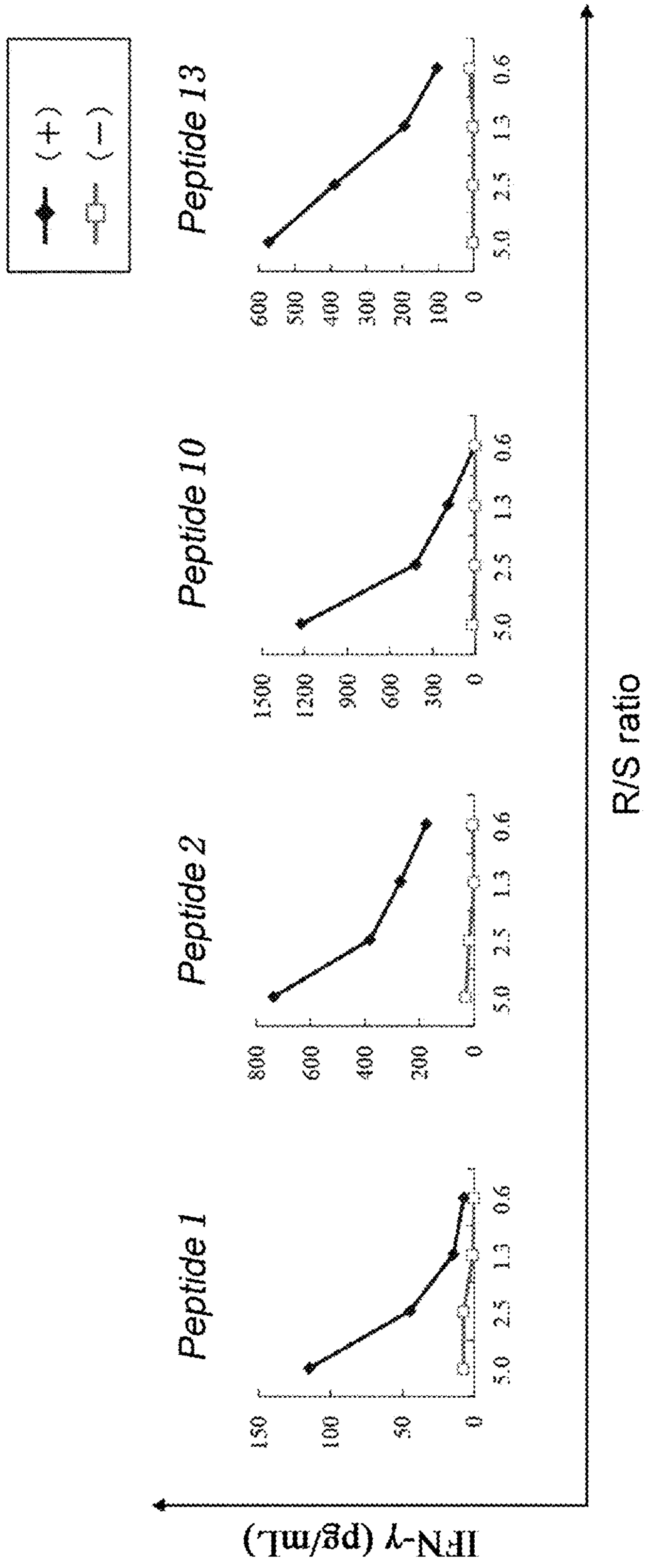
FIG. 4 is composed of line graphs showing the results of measuring IFN-γ produced by cells stimulated with Peptide 1 (SEQ ID NO: 1), Peptide 2 (SEQ ID NO: 2), Peptide 10 (SEQ ID NO: 10) or Peptide 13 (SEQ ID NO: 13), using an enzyme-linked immunosorbent assay (ELISA). These results show that after induction with the peptides, HLA-A*02:01-restricted CTL lines were established that produced IFN-γ in a peptide-specific manner. In the figure, "(+)" indicates IFN-γ production of a CTL line for HLA-A*02:01-expressing target cells (T2 cells) pulsed with a peptide of interest, and "(−)" indicates IFN-γ production of a CTL line for T2 cells not pulsed with any peptide. The R/S ratio represents the ratio of the number of CTL line cells, which are responder cells (Responder cells), to the number of target cells (Stimulator cells) that stimulate them.

Establishment of HLA-A*02:01-Restricted CTL Lines Specific to Peptides Derived from SARS-CoV-2 Proteins HLA-A*02:01-restricted CTL lines were established by proliferating the cells that showed IFN-γ production specific to Peptide 1 (SEQ ID NO: 1), Peptide 2 (SEQ ID NO: 2), Peptide 10 (SEQ ID NO: 10) or Peptide 13 (SEQ ID NO: 13) in the HLA-A*02:01 restricted-IFN-γ ELISPOT assay. As a result of measuring IFN-γ using ELISA, IFN-γ production by CTL lines for HLA-A*02:01-expressing target cells (T2 cells) pulsed with Peptide 1 (SEQ ID NO: 1), Peptide 2 (SEQ ID NO: 2), Peptide 10 (SEQ ID NO: 10) or Peptide 13 (SEQ ID NO: 13) was observed (FIG. 4). This clearly demonstrated that Peptide 1 (SEQ ID NO: 1), Peptide 2 (SEQ ID NO: 2), Peptide 10 (SEQ ID NO: 10) and Peptide 13 (SEQ ID NO: 13) also bind to HLA-A*02:01 and have the ability to induce HLA-A*02:01-restricted CTLs.

Homology Analysis of Peptides

Peptide 1 (SEQ ID NO: 1), Peptide 2 (SEQ ID NO: 2), Peptide 3 (SEQ ID NO: 3), Peptide 4 (SEQ ID NO: 4), Peptide 5 (SEQ ID NO: 5), Peptide 7 (SEQ ID NO: 7), Peptide 9 (SEQ ID NO: 9), Peptide 10 (SEQ ID NO: 10), Peptide 11 (SEQ ID NO: 11), Peptide 12 (SEQ ID NO: 12), Peptide 13 (SEQ ID NO: 13) and Peptide 15 (SEQ ID NO: 15) were confirmed to be able to induce CTLs that show peptide-specific IFN-γ production. Thus, homology analysis was performed using the BLAST algorithm (http://blast.ncbi.nlm.nih.gov/Blast.cgi) to check the homology between the amino acid sequences of Peptide 1 (SEQ ID NO: 1), Peptide 2 (SEQ ID NO: 2), Peptide 3 (SEQ ID NO: 3), Peptide 4 (SEQ ID NO: 4), Peptide 5 (SEQ ID NO: 5), Peptide 7 (SEQ ID NO: 7), Peptide 9 (SEQ ID NO: 9), Peptide 10 (SEQ ID NO: 10), Peptide 11 (SEQ ID NO: 11), Peptide 12 (SEQ ID NO: 12), Peptide 13 (SEQ ID NO: 13) and Peptide 15 (SEQ ID NO: 15) and amino acid sequences derived from human proteins. As a result, the amino acid sequences of Peptide 1 (SEQ ID NO: 1), Peptide 2 (SEQ ID NO: 2), Peptide 3 (SEQ ID NO: 3), Peptide 4 (SEQ ID NO: 4), Peptide 5 (SEQ ID NO: 5), Peptide 7 (SEQ ID NO: 7), Peptide 9 (SEQ ID NO: 9), Peptide 10 (SEQ ID NO: 10), Peptide 11 (SEQ ID NO: 11), Peptide 12 (SEQ ID NO: 12), Peptide 13 (SEQ ID NO: 13) and Peptide 15 (SEQ ID NO: 15) were not found in human proteins. Accordingly, as far as the present inventors know, these peptides are derived from SARS-CoV-2, or SARS-CoV or MERS-CoV and are very unlikely to evoke an unintended immune response against human normal tissues. In conclusion, novel HLA-A*24:02- or HLA-A*02:01-restricted epitope peptides derived from SARS-CoV-2 proteins were identified and shown to be applicable to peptide vaccines against COVID-19.

Example 2

Materials and Methods

Establishment of CTL Clones (Limiting Dilution)

Cells after in vitro CTL induction were seeded at 1 cell/well in 96-well round-bottomed microplate (Corning). Cells were cultured with two kinds of human B-lymphoblastoid cell lines treated with Mitomycin C (each $1\times10^4$ cells), anti-CD3 antibody (final concentration: 30 ng/ml), and IL-2 (final concentration: 150 IU/ml) (culture solution volume: 150 μl/well). AIM-V medium containing inactivated AB serum (SIGMA) (5% ABS/AIM-V medium) was used as medium. Ten days later, 50 μl of 5% ABS/AIM-V medium containing 600 IU/ml IL-2 was added to the culture (Uchida N et al., Clin Cancer Res 2004, 10(24): 8577-8586; Suda T et al., Cancer Sci 2006, 97(5): 411-419; Watanabe T et al., Cancer Sci 2005, 96(8): 498-506). On day 14 and thereafter, CTLs that showed peptide-specific IFN-γ production in ELISPOT assays were allowed to proliferate using the method described above (CTL proliferation procedure). ELISA was performed to again verify peptide-specific IFN-γ production. The IFN-γ ELISPOT assays and IFN-γ ELISA were performed according to the procedures recommended by the assay kit manufacturers. TISI cells were used as target cells.

TCR Analysis

RNAs were extracted from CTL clones specific to a peptide derived from SARS-CoV-2 protein by RNeasy mini kit, and then cDNAs were synthesized. Sanger sequencing was conducted for determining nucleotide sequences of TCR α chain and TCR β chain. Nucleotide sequences of TCR α chain were determined after TA cloning using M13 forward primer (5'-TGTAAAACGACGGCCAGTG-3' (SEQ ID NO: 42) or 5'-CTGGCCGTCGTTTTAC-3' (SEQ ID NO: 43)) and M13 reverse primer (5'-CAGGAAACAGCTATGACCAT-3' (SEQ ID NO: 44) or 5'-CAGGAAACAGCTATGAC-3' (SEQ ID NO: 45)). For determining nucleotide sequences of TCR β chain, forward primer (5'-GTCTCGTGGGCTCGGAGATGTGTATAAGAGACAGTATCAACGCAGAGTGGCCAT-3', SEQ ID NO: 46) and reverse primer (5'-TCGTCGGCAGCGTCAGATGTGTATAAGAGACAGDVHDVTCTGATGGCTCAAACACA GC-3', SEQ ID NO: 47) were used. The nucleotide sequences of the TCRα and TCRβ genes registered in a database of TCRs, IMGT/GENE-DB (Giudicelli V et al., Nucleic Acids Res 2005, 33(Database issue):D256-261), were referred to.

Results

Establishment of Peptide-Specific CTL Clones

Figure 5:
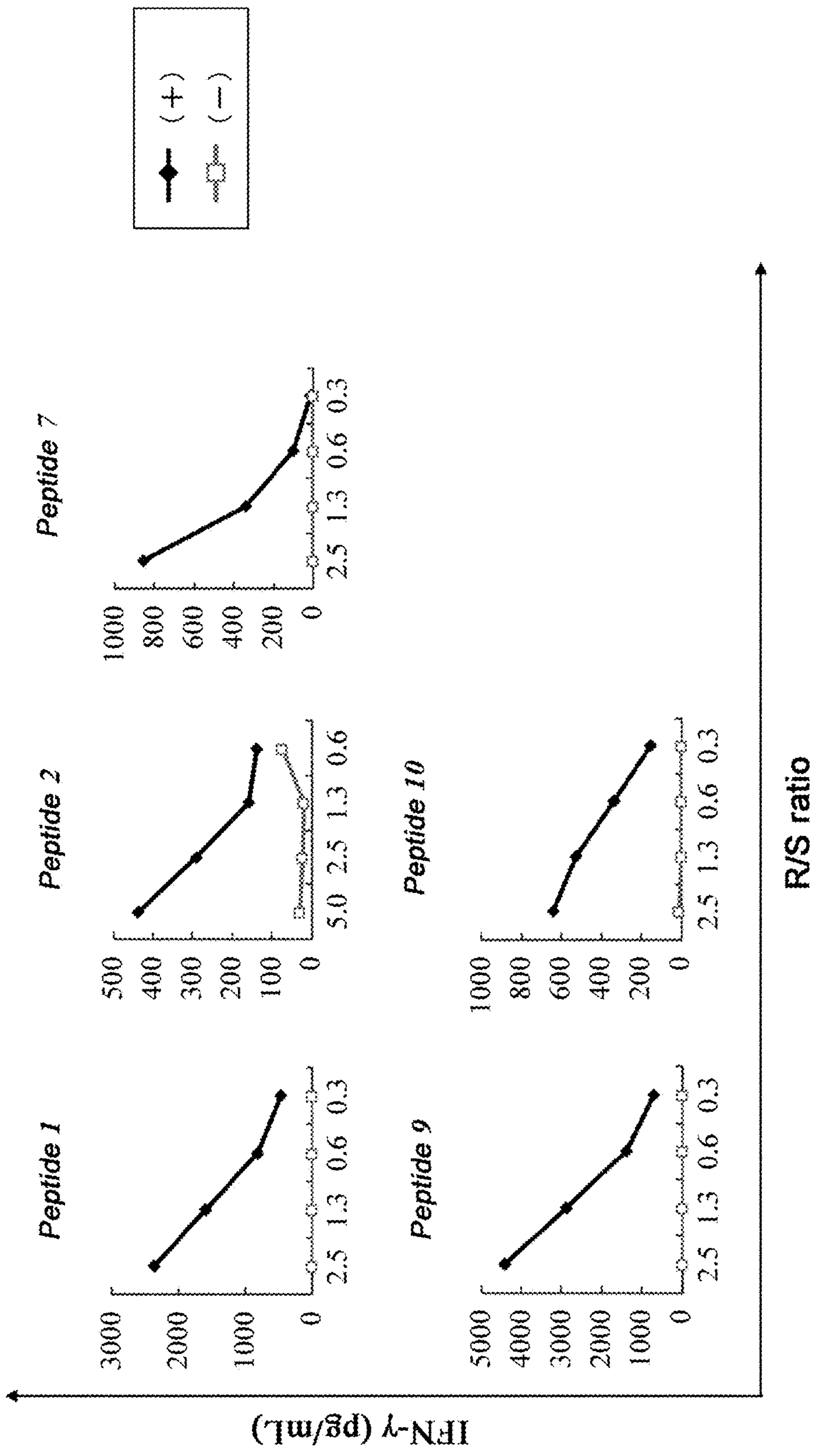
FIG. 5 is composed of line graphs showing IFN-γ production of CTL clones specific to SARS-CoV-2 protein-derived peptides that were established by limiting dilution method from PBMCs after in vitro CTL induction. IFN-γ production by CTL clones was observed for target cells (+) pulsed with SARS-CoV-2 protein-derived peptides, while no significant IFN-γ production by CTL clones was observed for target cells (−) not pulsed with a peptide. Thus, it was confirmed that the CTL clones recognized the SARS-CoV-2 protein-derived peptides presented on HLAs. The R/S ratio represents the ratio of the number of CTL clone cells, which are responder cells (Responder cells), to the number of target cells (Stimulator cells) that stimulate them.

CTL clones that recognize a SARS-CoV-2 protein-derived peptide were established by a limiting dilution method. As a result of IFN-γ measurement by ELISA, the CTL clones showed IFN-γ production specific to Peptide 1 (SEQ ID NO: 1), Peptide 2 (SEQ ID NO: 2), Peptide 7 (SEQ ID NO: 7), Peptide 9 (SEQ ID NO: 9) or Peptide 10 (SEQ ID NO: 10) (FIG. 5). Thus, it was confirmed that the CTL clones recognized the SARS-CoV-2 protein-derived peptides presented on HLAs.

Identification of TCRs Expressed by Peptide-Specific CTL Clones

The CDR3 amino acid sequences of TCRs expressed by the CTL clones specific to the SARS-CoV-2 protein-derived peptide were identified by Sanger sequencing analysis (Table 3).

TABLE 3

TCRs Identified from CTL Clones Specific to SARS-CoV-2 Protein-derived Peptide

| TCR | | V Region | J Region | CDR3 Amino Acid Sequence | SEQ ID NO |
|---|---|---|---|---|---|
| Peptide 1-responsive | alpha | TRAV1-2 | TRAJ32 | CAVRGSGGGATNKLIF | 32 |
| TCR | beta | TRBV9 | TRBJ2-7 | CASSPSGPNYEQYF | 33 |
| Peptide 2-responsive | alpha | TRAV21 | TRAJ20 | CAVENDYKLSF | 34 |
| TCR | beta | TRBV7-9 | TRBJ2-7 | CASSSRTSGRSSYEQYF | 35 |
| Peptide 7-responsive | alpha | TRAV10 | TRAJ31 | CVVSALNARLMF | 36 |
| TCR | beta | TRBV20-1 | TRBJ2-1 | CSARDYTSSYNEQFF | 37 |
| Peptide 9-responsive | alpha | TRAV20 | TRAJ11 | CAVHFFPGYSTLTF | 38 |
| TCR | beta | TRBV30 | TRBJ2-7 | CAGAGRGYEQYF | 39 |
| Peptide 10-responsive | alpha | TRAV26-1 | TRAJ5 | CIVSDMGRRALTF | 40 |
| TCR | beta | TRBV4-1 | TRBJ2-1 | CASSFTGTSGSLGEQFF | 41 |

Example 3

Materials and Methods

PBMCs

PBMCs derived from individuals who had recovered from COVID-19 (HLA-A*24:02-positive) from whom SARS-CoV-2-derived DNAs had been detected by an RT-PCR test (positive) and who had obtained a negative result in the test after a period of onset were purchased from Precision For Medicine. PBMCs derived from individuals not infected with SARS-CoV-2 (HLA-A*24:02-positive) which were collected before December 2019 were purchased from Cellular Technology Limited.

Culture of PBMCs

The PBMCs collected from individuals who had recovered from COVID-19 or those not infected with SARS-CoV-2 were seeded into 48-well multiwell plates (Corning) at $5\times10^5$ cells/well and then cultured for 12 days. A complete medium (a mixture of equal volume of RPMI1640 medium and AIM-V medium) containing inactivated fetal bovine serum (GIBCO) was used. Peptides were added on the start day of the culture and four days later (final concentration: 10 μg/ml). IL-2 was added 5, 7 and 10 days after the start of the culture (final concentration: 120 IU/ml). The PBMCs after the culture were used in tetramer assays.

Production of Tetramers

QuickSwitch™ Quant HLA-A*24:02 Tetramer Kit-PE (MBL International Corporation) was used to produce tetramers of Peptide 1 (SEQ ID NO: 1), Peptide 4 (SEQ ID NO: 4), Peptide (SEQ ID NO: 5), Peptide 7 (SEQ ID NO: 7), Peptide 9 (SEQ ID NO: 9), Peptide 10 (SEQ ID NO: 10) and Peptide 13 (SEQ ID NO: 13) according to the procedure recommended by the manufacturer. Fifty microliters of QuickSwitch™ Tetramer to which Exiting peptide has been bound was mixed with 1 μl of 1 mg/ml peptide solution. Furthermore, 1 μl of Peptide Exchange Factor was added and allowed to stand at room temperature for four hours or more, which resulted in obtaining tetramers in which Exiting peptide was replaced by a peptide of interest.

Tetramer Assay

Tetramer assays were performed on the PBMCs derived from individuals who had recovered from COVID-19 or those not infected with SARS-CoV-2. Since T cells that recognize a peptide bind to a tetramer via TCR, the PBMCs were treated with 450 nM Dasatinib (Cayman Chemical) (37° C., 30 minutes) for maintaining TCR expression on the T cell surface (Lissina A et al., J Immunol Methods 2009, 340(1): 11-24). The PBMCs were stained with a tetramer, and then further stained with a FITC-labeled anti-CD8 antibody, an APC-labeled anti-CD3 antibody and a PE-Cy7-labeled anti-CD4 antibody (all BD Biosciences). Finally, the PBMCs were stained with 0.1 μg/ml DAPI solution (BD Biosciences) and analyzed with a flow cytometer (SH800 cell sorter, Sony). Tetramer-positive CD8-positive T cells were identified in DAPI-negative CD3-positive CD4-negative cell populations. A PE-labeled HIV tetramer (MEDICAL & BIOLOGICAL LABORATORIES CO., LTD.) was used as a negative control.

Results

Detection of Tetramer-Positive CD8-Positive T Cells

Figures 1, 6:
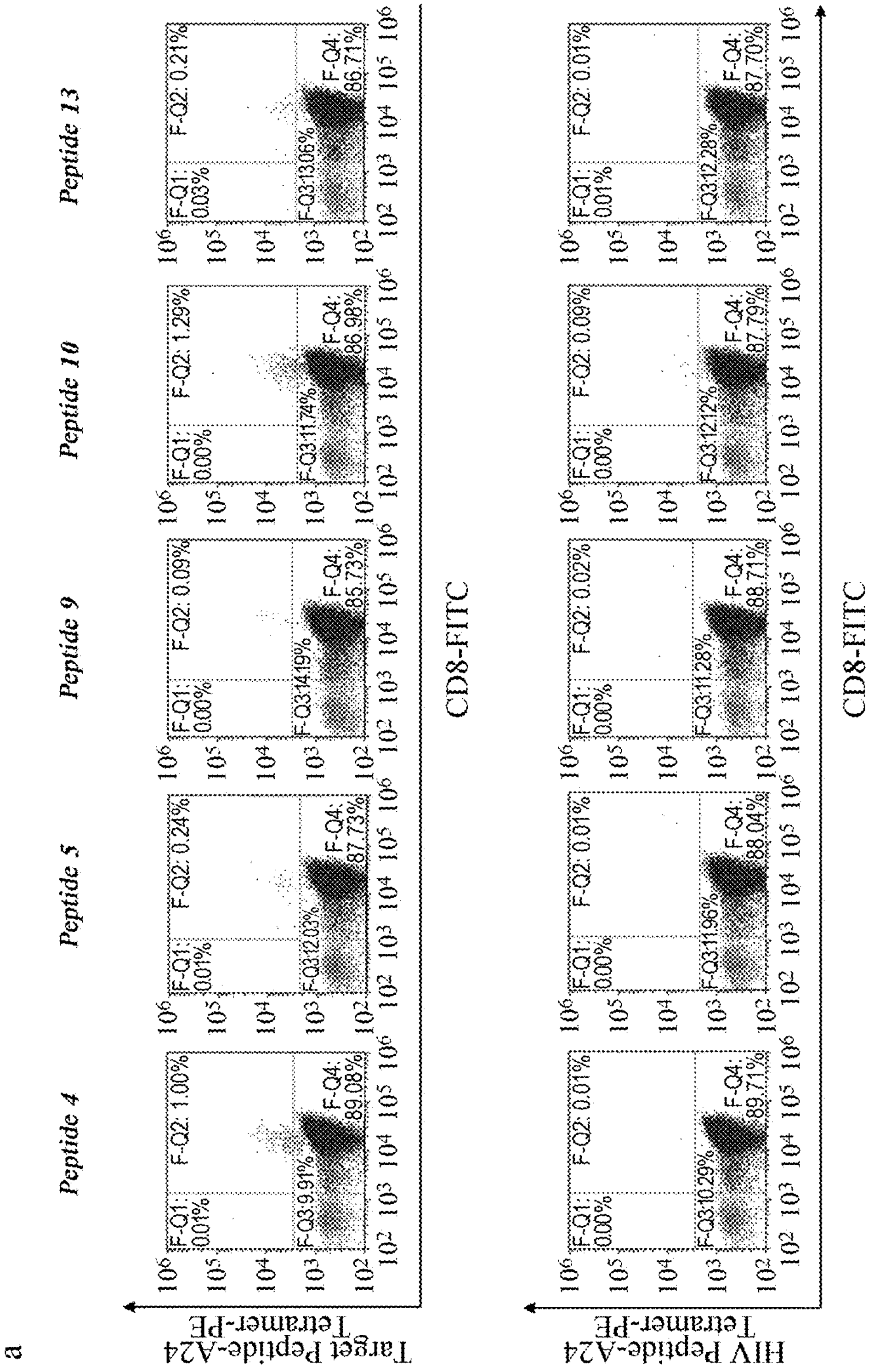
FIG. 6 is composed of the results (a) and (b) of tetramer assays performed on PBMCs collected from individuals who had recovered from COVID-19 or those not infected with SARS-CoV-2. Populations of tetramer-positive CD8-positive T cells that recognize SARS-CoV-2 protein-derived peptides presented on HLA-A*24:02 were detected in the PBMCs derived from individuals who had recovered from COVID-19 (FIG. 6*a*). Populations of tetramer-positive CD8-positive T cells were detected also in the PBMCs derived from individuals not infected with SARS-CoV-2 (FIG. 6*b*).
Figures 2, 6:
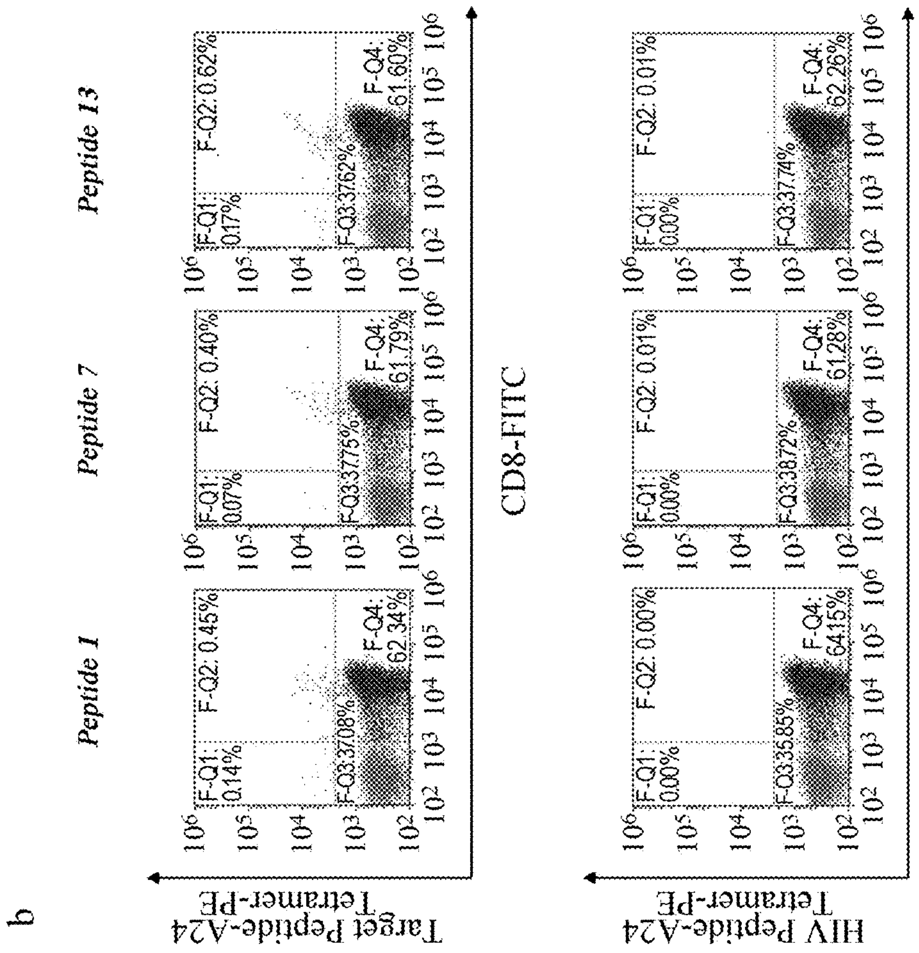

CD8-positive T cells recognizing Peptide 4 (SEQ ID NO: 4), Peptide 5 (SEQ ID NO: 5), Peptide 9 (SEQ ID NO: 9), Peptide 10 (SEQ ID NO: 10) or Peptide 13 (SEQ ID NO: 13) derived from SARS-CoV-2 proteins were detected in the PBMCs of individuals who had recovered from COVID-19 (FIG. 6*a*). CD8-positive T cells recognizing Peptide 1 (SEQ ID NO: 1), Peptide 7 (SEQ ID NO: 7) or Peptide 13 (SEQ ID NO: 13) were detected in the PBMCs of individuals not infected with SARS-CoV-2 (FIG. 6*b*). It was suggested that Peptide 4 (SEQ ID NO: 4), Peptide 5 (SEQ ID NO: 5), Peptide 9 (SEQ ID NO: 9), Peptide 10 (SEQ ID NO: 10) and Peptide 13 (SEQ ID NO: 13) may be epitopes causing induction of peptide-specific CTLs in vivo. It was confirmed that Peptide 1 (SEQ ID NO: 1), Peptide 7 (SEQ ID NO: 7) and Peptide 13 (SEQ ID NO: 13) can be recognized by some of CTLs (cross-reactive T cells) previously induced by foreign antigens. These results indicated that Peptide 1 (SEQ ID NO: 1), Peptide 4 (SEQ ID NO: 4), Peptide 5 (SEQ ID NO: 5), Peptide 7 (SEQ ID NO: 7), Peptide 9 (SEQ ID NO: 9), Peptide 10 (SEQ ID NO: 10) and Peptide 13 (SEQ ID NO: 13) can be applied to a peptide vaccine against COVID-19 as antigens that stimulate T cells and elicit cellular immunity.

Example 4

Materials and Methods

PBMCs

PBMCs are collected from the blood of a subject (HLA-A*24:02-positive) whose previous history of SARS-CoV-2 infection is to be examined. Moreover, PBMCs derived from an individual not infected with SARS-CoV-2 (HLA-A*24:02-positive) that were collected before December 2019 are purchased from Cellular Technology Limited.

TCR Analysis

RNAs are extracted from the PBMCs using RNeasy mini kit, and then cDNAs are synthesized. Alternatively, genomic DNA (gDNA) is extracted from the PBMCs. TCR-α and TCR-β sequences are analyzed using a next-generation sequencer to perform TCR repertoire analysis. To determine the nucleotide sequences of CDR3, the following primers are used:

```
Forward primer (adaptor sequence common to TCR-α
and TCR-β, SEQ ID NO: 46):
5'-GTCTCGTGGGCTCGGAGATGTGTATAAGAGACAGTATCAACGCAGA
GTGGCCAT-3'

Reverse primer (for TCR-α, SEQ ID NO: 48):
5'-TCGTCGGCAGCGTCAGATGTGTATAAGAGACAGDBDHHCAGGGTCA
GGGTTCTGGATA-3'

Reverse primer (for TCR-β, SEQ ID NO: 47):
5'-TCGTCGGCAGCGTCAGATGTGTATAAGAGACAGDVHDVTCTGATGG
CTCAAACACAGC-3'
```

Results

TCR Repertoire Analysis of the Subject's PBMCs

The detection frequency of TCR sequences is analyzed, and when TCR comprising CDR3 of TCRα or TCRβ shown in Table 3 is detected more frequently than in the comparative control (PBMCs derived from an individual not infected with SARS-CoV-2), it indicates that the subject has been previously infected with SARS-CoV-2.

INDUSTRIAL APPLICABILITY

The present invention provides novel HLA-A24- or HLA-A02-restricted epitope peptides derived from SARS-CoV-2 proteins that induce a potent and specific immune response against coronavirus infection and thus can have applicability to a wide variety of coronavirus infectious diseases. The peptides, compositions, APCs, and CTLs of the present invention can be used as peptide vaccines against coronavirus infectious diseases, for example SARS-CoV-2, MERS-CoV, or SARS-CoV infectious diseases.

Furthermore, the sequences of TCR induced by the peptide of the present invention may be used for methods of detecting history of SARS-CoV-2 infectious diseases.

While the present invention is herein described in detail and with respect to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. A peptide of less than 15 amino acids having cytotoxic T cell (CTL)-inducing ability, which comprises the amino acid sequence selected from the group consisting of SEQ ID NOs: 4, 7, 9, 10, 11, 12, and 13, into which one or two amino acid substitutions are introduced, wherein the peptide is selected from the group consisting of:

(i) a peptide comprising the amino acid sequence selected from the group consisting of SEQ ID NOs: 4, 7, 9, 10, 11, 12 and 13, wherein the one or two amino acid substitutions are selected from the group consisting of:

(a) substitution of the second amino acid from the N terminus with an amino acid selected from the group consisting of phenylalanine, tyrosine, methionine and tryptophan; and (b) substitution of the C-terminal amino acid with an amino acid selected from the group consisting of phenylalanine, leucine, isoleucine, tryptophan and methionine; and (ii) a peptide comprising the amino acid sequence selected from the group consisting of SEQ ID NOs: 4, 7, 10, 12 and 13, wherein the one or two amino acid substitutions are selected from the group consisting of:

(c) substitution of the second amino acid from the N terminus with leucine or methionine; and (d) substitution of the C-terminal amino acid with valine or leucine.

2. A composition comprising a pharmaceutically acceptable carrier, an adjuvant in an amount effective for enhancing cellular immunity, and at least one active ingredient selected from the group consisting of:

(a) an isolated peptide of less than 15 amino acids having cytotoxic T cell (CTL)-inducing ability, which comprises the amino acid sequence selected from the group consisting of:

(i) the amino acid sequence selected from the group consisting of SEQ ID NOs: 4, 7, 9, 10, 11, 12 and 13; and (ii) the amino acid sequence selected from the group consisting of SEQ ID NOs: 4, 7, 9, 10, 11, 12 and 13, into which one or two amino acid substitutions are introduced, wherein the isolated peptide is selected from the group consisting of:

(1) a peptide comprising the amino acid sequence selected from the group consisting of SEQ ID NOs: 4, 7, 9, 10, 11, 12 and 13, wherein the one or two amino acid substitutions are selected from the group consisting of:

(A) substitution of the second amino acid from the N terminus with an amino acid selected from the group consisting of phenylalanine, tyrosine, methionine and tryptophan; and (B) substitution of the C-terminal amino acid with an amino acid selected from the group consisting of phenylalanine, leucine, isoleucine, tryptophan and methionine; and (2) a peptide comprising the amino acid sequence selected from the group consisting of SEQ ID NOs: 4, 7, 10, 12 and 13, wherein the one or two substitutions are selected from the group consisting of:

(C) substitution of the second amino acid from the N terminus with leucine or methionine; and (D) substitution of the C-terminal amino acid with valine or leucine;

(b) a polynucleotide encoding the isolated peptide of (a) in an expressible form;

(c) an antigen-presenting cell (APC) that presents on its cell surface a complex of the isolated peptide of (a) and an HLA antigen;

(d) an exosome that presents on its cell surface a complex of the isolated peptide of (a) and an HLA antigen; and (e) a CTL that targets the isolated peptide of (a).

3. A method of inducing an APC(s) having CTL-inducing ability, which comprises a step selected from the group consisting of (a) and (b) below:

(a) contacting an APC(s) with a peptide in vitro, ex vivo or in vivo; and (b) introducing a polynucleotide encoding a peptide into an APC(s), wherein the peptide is an isolated peptide of less than 15 amino acids having cytotoxic T cell (CTL)-inducing ability, which comprises the amino acid sequence selected from the group consisting of:

(i) the amino acid sequence selected from the group consisting of SEQ ID NOs: 4, 7, 9, 10, 11, 12 and 13; and (ii) the amino acid sequence selected from the group consisting of SEQ ID NOs: 4, 7, 9, 10, 11, 12 and 13, into which one or two amino acid substitutions are introduced, wherein the peptide is selected from the group consisting of:

(1) a peptide comprising the amino acid sequence selected from the group consisting of SEQ ID NOs: 4, 7, 9, 10, 11, 12 and 13, wherein the one or two amino acid substitutions are selected from the group consisting of:

(A) substitution of the second amino acid from the N terminus with an amino acid selected from the group consisting of phenylalanine, tyrosine, methionine and tryptophan; and (B) substitution of the C-terminal amino acid with an amino acid selected from the group consisting of phenylalanine, leucine, isoleucine, tryptophan and methionine; and (2) a peptide comprising the amino acid sequence selected from the group consisting of SEQ ID NOs: 4, 7, 10, 12 and 13, wherein the one or two substitutions are selected from the group consisting of:

(C) substitution of the second amino acid from the N terminus with leucine or methionine; and (D) substitution of the C-terminal amino acid with valine or leucine.

4. A method of inducing a CTL(s), which comprises a step selected from the group consisting of (a) to (c) below:

(a) co-culturing a CD8-positive T cell(s) with an APC(s) that presents on its surface a complex of an HLA antigen and a peptide;

(b) co-culturing a CD8-positive T cell(s) with an exosome(s) that presents on its surface a complex of an HLA antigen and a peptide; and (c) introducing into a CD8-positive T cell(s) a polynucleotide encoding each subunit of a T cell receptor (TCR) capable of binding to a peptide presented by an HLA antigen on a cell surface, wherein the peptide is an isolated peptide of less than 15 amino acids having cytotoxic T cell (CTL)-inducing ability, which comprises the amino acid sequence selected from the group consisting of:

(i) the amino acid sequence selected from the group consisting of SEQ ID NOs: 4, 7, 9, 10, 11, 12 and 13; and (ii) the amino acid sequence selected from the group consisting of SEQ ID NOs: 4, 7, 9, 10, 11, 12 and 13, into which one or two amino acid substitutions are introduced, wherein the peptide is selected from the group consisting of:

(1) a peptide comprising the amino acid sequence selected from the group consisting of SEQ ID NOs: 4, 7, 9, 10, 11, 12 and 13, wherein the one or two amino acid substitutions are selected from the group consisting of:

(A) substitution of the second amino acid from the N terminus with an amino acid selected from the group consisting of phenylalanine, tyrosine, methionine and tryptophan; and (B) substitution of the C-terminal amino acid with an amino acid selected from the group consisting of phenylalanine, leucine, isoleucine, tryptophan and methionine; and (2) a peptide comprising the amino acid sequence selected from the group consisting of SEQ ID NOs: 4, 7, 10, 12 and 13, wherein the one or two substitutions are selected from the group consisting of:

(C) substitution of the second amino acid from the N terminus with leucine or methionine; and (D) substitution of the C-terminal amino acid with valine or leucine.

5. A method of inducing an immune response against coronavirus infection, which comprises administering the composition of claim 2 to a subject.

6. A method of treating and/or preventing coronavirus infectious disease, and/or suppressing aggravation of coronavirus infectious disease, which comprises administering the composition of claim 2 to a subject.

7. A kit comprising a container that houses the composition of claim 2 and a container that houses the adjuvant.

* * * * *

```
                         SEQUENCE LISTING


<160> NUMBER OF SEQ ID NOS: 48

<210> SEQ ID NO 1
<211> LENGTH: 9
<212> TYPE: PRT
<213> ORGANISM: Artificial Sequence
<220> FEATURE:
<223> OTHER INFORMATION: an amino acid sequence derived from ORF1ab
      polyprotein of SARS-CoV-2

<400> SEQUENCE: 1

Ala Tyr Ala Asn Ser Val Phe Asn Ile
1               5


<210> SEQ ID NO 2
<211> LENGTH: 10
<212> TYPE: PRT
<213> ORGANISM: Artificial Sequence
<220> FEATURE:
<223> OTHER INFORMATION: an amino acid sequence derived from ORF1ab
      polyprotein of SARS-CoV-2

<400> SEQUENCE: 2

Thr Ala Tyr Ala Asn Ser Val Phe Asn Ile
1               5                   10


<210> SEQ ID NO 3
<211> LENGTH: 9
<212> TYPE: PRT
<213> ORGANISM: Artificial Sequence
<220> FEATURE:
<223> OTHER INFORMATION: an amino acid sequence derived from ORF1ab
      polyprotein of SARS-CoV-2

<400> SEQUENCE: 3

Val Phe Met Ser Glu Ala Lys Cys Trp
1               5


<210> SEQ ID NO 4
<211> LENGTH: 9
<212> TYPE: PRT
<213> ORGANISM: Artificial Sequence
<220> FEATURE:
<223> OTHER INFORMATION: an amino acid sequence derived from ORF1ab
      polyprotein of SARS-CoV-2

<400> SEQUENCE: 4

Thr Tyr Ala Ser Ala Leu Trp Glu Ile
1               5


<210> SEQ ID NO 5
<211> LENGTH: 10
<212> TYPE: PRT
<213> ORGANISM: Artificial Sequence
<220> FEATURE:
<223> OTHER INFORMATION: an amino acid sequence derived from surface
      glycoprotein of SARS-CoV-2

<400> SEQUENCE: 5
```

Pro Phe Ala Met Gln Met Ala Tyr Arg Phe
1 5 10

<210> SEQ ID NO 6
<211> LENGTH: 10
<212> TYPE: PRT
<213> ORGANISM: Artificial Sequence
<220> FEATURE:
<223> OTHER INFORMATION: an amino acid sequence derived from ORF1ab polyprotein of SARS-CoV-2

<400> SEQUENCE: 6

Tyr Asp Tyr Leu Val Ser Thr Gln Glu Phe
1 5 10

<210> SEQ ID NO 7
<211> LENGTH: 10
<212> TYPE: PRT
<213> ORGANISM: Artificial Sequence
<220> FEATURE:
<223> OTHER INFORMATION: an amino acid sequence derived from ORF1ab polyprotein of SARS-CoV-2

<400> SEQUENCE: 7

Tyr Tyr Ser Gln Leu Met Cys Gln Pro Ile
1 5 10

<210> SEQ ID NO 8
<211> LENGTH: 9
<212> TYPE: PRT
<213> ORGANISM: Artificial Sequence
<220> FEATURE:
<223> OTHER INFORMATION: an amino acid sequence derived from ORF1ab polyprotein of SARS-CoV-2

<400> SEQUENCE: 8

Ser Tyr Tyr Ser Leu Leu Met Pro Ile
1 5

<210> SEQ ID NO 9
<211> LENGTH: 9
<212> TYPE: PRT
<213> ORGANISM: Artificial Sequence
<220> FEATURE:
<223> OTHER INFORMATION: an amino acid sequence derived from ORF1ab polyprotein of SARS-CoV-2

<400> SEQUENCE: 9

Arg Tyr Lys Leu Glu Gly Tyr Ala Phe
1 5

<210> SEQ ID NO 10
<211> LENGTH: 10
<212> TYPE: PRT
<213> ORGANISM: Artificial Sequence
<220> FEATURE:
<223> OTHER INFORMATION: an amino acid sequence derived from ORF1ab polyprotein of SARS-CoV-2

<400> SEQUENCE: 10

Phe Thr Tyr Ala Ser Ala Leu Trp Glu Ile
1 5 10

<210> SEQ ID NO 11
<211> LENGTH: 10
<212> TYPE: PRT
<213> ORGANISM: Artificial Sequence

```
<220> FEATURE:
<223> OTHER INFORMATION: an amino acid sequence derived from ORF1ab
      polyprotein of SARS-CoV-2

<400> SEQUENCE: 11

Ser Tyr Ser Leu Phe Asp Met Ser Lys Phe
1               5                   10


<210> SEQ ID NO 12
<211> LENGTH: 10
<212> TYPE: PRT
<213> ORGANISM: Artificial Sequence
<220> FEATURE:
<223> OTHER INFORMATION: an amino acid sequence derived from ORF1ab
      polyprotein of SARS-CoV-2

<400> SEQUENCE: 12

Arg Tyr Phe Lys Tyr Trp Asp Gln Thr Tyr
1               5                   10


<210> SEQ ID NO 13
<211> LENGTH: 9
<212> TYPE: PRT
<213> ORGANISM: Artificial Sequence
<220> FEATURE:
<223> OTHER INFORMATION: an amino acid sequence derived from membrane
      glycoprotein of SARS-CoV-2

<400> SEQUENCE: 13

Leu Trp Leu Leu Trp Pro Val Thr Leu
1               5


<210> SEQ ID NO 14
<211> LENGTH: 10
<212> TYPE: PRT
<213> ORGANISM: Artificial Sequence
<220> FEATURE:
<223> OTHER INFORMATION: an amino acid sequence derived from ORF1ab
      polyprotein of SARS-CoV-2

<400> SEQUENCE: 14

Thr Tyr Ala Ser Ala Leu Trp Glu Ile Gln
1               5                   10


<210> SEQ ID NO 15
<211> LENGTH: 10
<212> TYPE: PRT
<213> ORGANISM: Artificial Sequence
<220> FEATURE:
<223> OTHER INFORMATION: an amino acid sequence derived from ORF1ab
      polyprotein of SARS-CoV-2

<400> SEQUENCE: 15

Tyr Ala Tyr Leu Arg Lys His Phe Ser Met
1               5                   10


<210> SEQ ID NO 16
<211> LENGTH: 29903
<212> TYPE: DNA
<213> ORGANISM: Severe acute respiratory syndrome coronavirus 2

<400> SEQUENCE: 16

attaaaggtt tataccttcc caggtaacaa accaaccaac tttcgatctc ttgtagatct      60

gttctctaaa cgaactttaa aatctgtgtg gctgtcactc ggctgcatgc ttagtgcact     120

cacgcagtat aattaataac taattactgt cgttgacagg acacgagtaa ctcgtctatc     180
```

-continued

```
ttctgcaggc tgcttacggt ttcgtccgtg ttgcagccga tcatcagcac atctaggttt    240
cgtccgggtg tgaccgaaag gtaagatgga gagccttgtc cctggtttca acgagaaaac    300
acacgtccaa ctcagtttgc ctgttttaca ggttcgcgac gtgctcgtac gtggctttgg    360
agactccgtg gaggaggtct tatcagaggc acgtcaacat cttaaagatg gcacttgtgg    420
cttagtagaa gttgaaaaag gcgttttgcc tcaacttgaa cagccctatg tgttcatcaa    480
acgttcggat gctcgaactg cacctcatgg tcatgttatg gttgagctgg tagcagaact    540
cgaaggcatt cagtacggtc gtagtggtga gacacttggt gtccttgtcc ctcatgtggg    600
cgaaatacca gtggcttacc gcaaggttct tcttcgtaag aacggtaata aaggagctgg    660
tggccatagt tacggcgccg atctaaagtc atttgactta ggcgacgagc ttggcactga    720
tccttatgaa gattttcaag aaaactggaa cactaaacat agcagtggtg ttacccgtga    780
actcatgcgt gagcttaacg gaggggcata cactcgctat gtcgataaca acttctgtgg    840
ccctgatggc taccctcttg agtgcattaa agaccttcta gcacgtgctg gtaaagcttc    900
atgcactttg tccgaacaac tggactttat tgacactaag aggggtgtat actgctgccg    960
tgaacatgag catgaaattg cttggtacac ggaacgttct gaaaagagct atgaattgca   1020
gacacctttt gaaattaaat tggcaaagaa atttgacacc ttcaatgggg aatgtccaaa   1080
ttttgtattt cccttaaatt ccataatcaa gactattcaa ccaagggttg aaaagaaaaa   1140
gcttgatggc tttatgggta gaattcgatc tgtctatcca gttgcgtcac caaatgaatg   1200
caaccaaatg tgcctttcaa ctctcatgaa gtgtgatcat tgtggtgaaa cttcatggca   1260
gacgggcgat tttgttaaag ccacttgcga attttgtggc actgagaatt tgactaaaga   1320
aggtgccact acttgtggtt acttacccca aaatgctgtt gttaaaattt attgtccagc   1380
atgtcacaat tcagaagtag gacctgagca tagtcttgcc gaataccata atgaatctgg   1440
cttgaaaacc attcttcgta agggtggtcg cactattgcc tttggaggct gtgtgttctc   1500
ttatgttggt tgccataaca agtgtgccta ttgggttcca cgtgctagcg ctaacatagg   1560
ttgtaaccat acaggtgttg ttggagaagg ttccgaaggt cttaatgaca accttcttga   1620
aatactccaa aaagagaaag tcaacatcaa tattgttggt gactttaaac ttaatgaaga   1680
gatcgccatt attttggcat ctttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagtttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat ttgtcacgca   2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
```

agctgttgaa gctccattgg ttggtacacc agtttgtatt aacgggctta tgttgctcga 2640
aatcaaagac acagaaaagt actgtgccct tgcacctaat atgatggtaa caaacaatac 2700
cttcacactc aaaggcggtg caccaacaaa ggttactttt ggtgatgaca ctgtgataga 2760
agtgcaaggt tacaagagtg tgaatatcac ttttgaactt gatgaaagga ttgataaagt 2820
acttaatgag aagtgctctg cctatacagt tgaactcggt acagaagtaa atgagttcgc 2880
ctgtgttgtg gcagatgctg tcataaaaac tttgcaacca gtatctgaat tacttacacc 2940
actgggcatt gatttagatg agtggagtat ggctacatac tacttatttg atgagtctgg 3000
tgagtttaaa ttggcttcac atatgtattg ttctttctac cctccagatg aggatgaaga 3060
agaaggtgat tgtgaagaag aagagtttga gccatcaact caatatgagt atggtactga 3120
agatgattac caaggtaaac ctttggaatt tggtgccact tctgctgctc ttcaacctga 3180
agaagagcaa gaagaagatt ggttagatga tgatagtcaa caaactgttg gtcaacaaga 3240
cggcagtgag gacaatcaga caactactat tcaaacaatt gttgaggttc aacctcaatt 3300
agagatggaa cttacaccag ttgttcagac tattgaagtg aatagtttta gtggttattt 3360
aaaacttact gacaatgtat acattaaaaa tgcagacatt gtggaagaag ctaaaaaggt 3420
aaaaccaaca gtggttgtta atgcagccaa tgtttacctt aaacatggag gaggtgttgc 3480
aggagcctta aataaggcta ctaacaatgc catgcaagtt gaatctgatg attacatagc 3540
tactaatgga ccacttaaag tgggtggtag ttgtgtttta agcggacaca atcttgctaa 3600
acactgtctt catgttgtcg gcccaaatgt taacaaaggt gaagacattc aacttcttaa 3660
gagtgcttat gaaaatttta atcagcacga agttctactt gcaccattat tatcagctgg 3720
tatttttggt gctgacccta tacattcttt aagagtttgt gtagatactg ttcgcacaaa 3780
tgtctactta gctgtctttg ataaaaatct ctatgacaaa cttgtttcaa gctttttgga 3840
aatgaagagt gaaaagcaag ttgaacaaaa gatcgctgag attcctaaag aggaagttaa 3900
gccatttata actgaaagta aaccttcagt tgaacagaga aaacaagatg ataagaaaat 3960
caaagcttgt gttgaagaag ttacaacaac tctggaagaa actaagttcc tcacagaaaa 4020
cttgttactt tatattgaca ttaatggcaa tcttcatcca gattctgcca ctcttgttag 4080
tgacattgac atcactttct taaagaaaga tgctccatat atagtgggtg atgttgttca 4140
agagggtgtt ttaactgctg tggttatacc tactaaaaag gctggtggca ctactgaaat 4200
gctagcgaaa gctttgagaa aagtgccaac agacaattat ataaccactt acccgggtca 4260
gggtttaaat ggttacactg tagaggaggc aaagacagtg cttaaaaagt gtaaaagtgc 4320
cttttacatt ctaccatcta ttatctctaa tgagaagcaa gaaattcttg gaactgtttc 4380
ttggaatttg cgagaaatgc ttgcacatgc agaagaaaca cgcaaattaa tgcctgtctg 4440
tgtggaaact aaagccatag tttcaactat acagcgtaaa tataagggta ttaaaataca 4500
agagggtgtg gttgattatg gtgctagatt ttacttttac accagtaaaa caactgtagc 4560
gtcacttatc aacacactta acgatctaaa tgaaactctt gttacaatgc cacttggcta 4620
tgtaacacat ggcttaaatt tggaagaagc tgctcggtat atgagatctc tcaaagtgcc 4680
agctacagtt tctgtttctt cacctgatgc tgttacagcg tataatggtt atcttacttc 4740
ttcttctaaa acacctgaag aacattttat tgaaaccatc tcacttgctg gttcctataa 4800
agattggtcc tattctggac aatctacaca actaggtata gaatttctta agagaggtga 4860
taaaagtgta tattacacta gtaatcctac cacattccac ctagatggtg aagttatcac 4920

-continued

```
ctttgacaat cttaagacac ttctttcttt gagagaagtg aggactatta aggtgtttac   4980
aacagtagac aacattaacc tccacacgca agttgtggac atgtcaatga catatggaca   5040
acagtttggt ccaacttatt tggatggagc tgatgttact aaaataaaac ctcataattc   5100
acatgaaggt aaaacatttt atgttttacc taatgatgac actctacgtg ttgaggcttt   5160
tgagtactac cacacaactg atcctagttt tctgggtagg tacatgtcag cattaaatca   5220
cactaaaaag tggaaatacc cacaagttaa tggtttaact tctattaaat gggcagataa   5280
caactgttat cttgccactg cattgttaac actccaacaa atagagttga agtttaatcc   5340
acctgctcta caagatgctt attacagagc aagggctggt gaagctgcta acttttgtgc   5400
acttatctta gcctactgta ataagacagt aggtgagtta ggtgatgtta gagaaacaat   5460
gagttacttg tttcaacatg ccaatttaga ttcttgcaaa agagtcttga acgtggtgtg   5520
taaaacttgt ggacaacagc agacaaccct taagggtgta gaagctgtta tgtacatggg   5580
cacactttct tatgaacaat ttaagaaagg tgttcagata ccttgtacgt gtggtaaaca   5640
agctacaaaa tatctagtac aacaggagtc accttttgtt atgatgtcag caccacctgc   5700
tcagtatgaa cttaagcatg gtacatttac ttgtgctagt gagtacactg gtaattacca   5760
gtgtggtcac tataaacata taacttctaa agaaactttg tattgcatag acggtgcttt   5820
acttacaaag tcctcagaat acaaaggtcc tattacggat gttttctaca aagaaaacag   5880
ttacacaaca accataaaac cagttactta taaattggat ggtgttgttt gtacagaaat   5940
tgaccctaag ttggacaatt attataagaa agacaattct tatttcacag agcaaccaat   6000
tgatcttgta ccaaaccaac catatccaaa cgcaagcttc gataatttta agtttgtatg   6060
tgataatatc aaatttgctg atgatttaaa ccagttaact ggttataaga aacctgcttc   6120
aagagagctt aaagttacat tttccctgaa cttaaatggt gatgtggtgg ctattgatta   6180
taaacactac acaccctctt ttaagaaagg agctaaattg ttacataaac ctattgtttg   6240
gcatgttaac aatgcaacta ataaagccac gtataaacca aatacctggt gtatacgttg   6300
tctttggagc acaaaaccag ttgaaacatc aaattcgttt gatgtactga agtcagagga   6360
cgcgcaggga atggataatc ttgcctgcga agatctaaaa ccagtctctg aagaagtagt   6420
ggaaaatcct accatacaga aagacgttct tgagtgtaat gtgaaaacta ccgaagttgt   6480
aggagacatt atacttaaac cagcaaataa tagtttaaaa attacagaag aggttggcca   6540
cacagatcta atggctgctt atgtagacaa ttctagtctt actattaaga aacctaatga   6600
attatctaga gtattaggtt tgaaaaccct tgctactcat ggtttagctg ctgttaatag   6660
tgtcccttgg gatactatag ctaattatgc taagcctttt cttaacaaag ttgttagtac   6720
aactactaac atagttacac ggtgtttaaa ccgtgtttgt actaattata tgccttattt   6780
ctttacttta ttgctacaat tgtgtacttt tactagaagt acaaattcta gaattaaagc   6840
atctatgccg actactatag caaagaatac tgttaagagt gtcggtaaat tttgtctaga   6900
ggcttcattt aattatttga agtcacctaa tttttctaaa ctgataaata ttataatttg   6960
gtttttacta ttaagtgttt gcctaggttc tttaatctac tcaaccgctg ctttaggtgt   7020
tttaatgtct aatttaggca tgccttctta ctgtactggt tacagagaag gctatttgaa   7080
ctctactaat gtcactattg caacctactg tactggttct ataccttgta gtgtttgtct   7140
tagtggttta gattctttag acacctatcc ttctttagaa actatacaaa ttaccatttc   7200
atcttttaaa tgggatttaa ctgcttttgg cttagttgca gagtggtttt tggcatatat   7260
tcttttcact aggtttttct atgtacttgg attggctgca atcatgcaat tgtttttcag   7320
```

```
ctattttgca gtacatttta ttagtaattc ttggcttatg tggttaataa ttaatcttgt   7380
acaaatggcc ccgatttcag ctatggttag aatgtacatc ttctttgcat cattttatta   7440
tgtatggaaa agttatgtgc atgttgtaga cggttgtaat tcatcaactt gtatgatgtg   7500
ttacaaacgt aatagagcaa caagagtcga atgtacaact attgttaatg gtgttagaag   7560
gtccttttat gtctatgcta atggaggtaa aggcttttgc aaactacaca attggaattg   7620
tgttaattgt gatacattct gtgctggtag tacatttatt agtgatgaag ttgcgagaga   7680
cttgtcacta cagtttaaaa gaccaataaa tcctactgac cagtcttctt acatcgttga   7740
tagtgttaca gtgaagaatg gttccatcca tctttacttt gataaagctg gtcaaaagac   7800
ttatgaaaga cattctctct ctcattttgt taacttagac aacctgagag ctaataacac   7860
taaaggttca ttgcctatta atgttatagt ttttgatggt aaatcaaaat gtgaagaatc   7920
atctgcaaaa tcagcgtctg tttactacag tcagcttatg tgtcaaccta tactgttact   7980
agatcaggca ttagtgtctg atgttggtga tagtgcggaa gttgcagtta aaatgtttga   8040
tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
ttttatttca gcagctcggc aagggtttgt tgattcagat gtagaaacta aagatgttgt   8220
tgaatgtctt aaattgtcac atcaatctga catagaagtt actggcgata gttgtaataa   8280
ctatatgctc acctataaca aagttgaaaa catgacaccc cgtgaccttg gtgcttgtat   8340
tgactgtagt gcgcgtcata ttaatgcgca ggtagcaaaa agtcacaaca ttgctttgat   8400
atggaacgtt aaagatttca tgtcattgtc tgaacaacta cgaaaacaaa tacgtagtgc   8460
tgctaaaaag aataacttac cttttaagtt gacatgtgca actactagac aagttgttaa   8520
tgttgtaaca acaaagatag cacttaaggg tggtaaaatt gttaataatt ggttgaagca   8580
gttaattaaa gttacacttg tgttcctttt tgttgctgct attttctatt taataacacc   8640
tgttcatgtc atgtctaaac atactgactt ttcaagtgaa atcataggat acaaggctat   8700
tgatggtggt gtcactcgtg acatagcatc tacagatact tgttttgcta acaaacatgc   8760
tgattttgac acatggttta gccagcgtgg tggtagttat actaatgaca aagcttgccc   8820
attgattgct gcagtcataa caagagaagt gggttttgtc gtgcctggtt tgcctggcac   8880
gatattacgc acaactaatg gtgacttttt gcatttctta cctagagttt ttagtgcagt   8940
tggtaacatc tgttacacac catcaaaact tatagagtac actgactttg caacatcagc   9000
ttgtgttttg gctgctgaat gtacaatttt taaagatgct tctggtaagc cagtaccata   9060
ttgttatgat accaatgtac tagaaggttc tgttgcttat gaaagtttac gccctgacac   9120
acgttatgtg ctcatggatg gctctattat tcaatttcct aacacctacc ttgaaggttc   9180
tgttagagtg gtaacaactt ttgattctga gtactgtagg cacggcactt gtgaaagatc   9240
agaagctggt gtttgtgtat ctactagtgg tagatgggta cttaacaatg attattacag   9300
atctttacca ggagttttct gtggtgtaga tgctgtaaat ttacttacta atatgtttac   9360
accactaatt caacctattg gtgctttgga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact cattcttacc tggtgtttat tctgttattt acttgtactt   9600
gacattttat cttactaatg atgtttcttt tttagcacat attcagtgga tggttatgtt   9660
```

```
cacaccttta gtacctttct ggataacaat tgcttatatc atttgtattt ccacaaagca   9720
tttctattgg ttctttagta attacctaaa gagacgtgta gtctttaatg gtgtttcctt   9780
tagtactttt gaagaagctg cgctgtgcac ctttttgtta aataaagaaa tgtatctaaa   9840
gttgcgtagt gatgtgctat tacctcttac gcaatataat agatacttag ctctttataa   9900
taagtacaag tattttagtg gagcaatgga tacaactagc tacagagaag ctgcttgttg   9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
tctttggctt gatgacgtag tttactgtcc aagacatgtg atctgcacct ctgaagacat  10200
gcttaaccct aattatgaag atttactcat tcgtaagtct aatcataatt tcttggtaca  10260
ggctggtaat gttcaactca gggttattgg acattctatg caaaattgtg tacttaagct  10320
taaggttgat acagccaatc ctaagacacc taagtataag tttgttcgca ttcaaccagg  10380
acagactttt tcagtgttag cttgttacaa tggttcacca tctggtgttt accaatgtgc  10440
tatgaggccc aatttcacta ttaagggttc attccttaat ggttcatgtg gtagtgttgg  10500
ttttaacata gattatgact gtgtctcttt ttgttacatg caccatatgg aattaccaac  10560
tggagttcat gctggcacag acttagaagg taacttttat ggaccttttg ttgacaggca  10620
aacagcacaa gcagctggta cggacacaac tattacagtt aatgttttag cttggttgta  10680
cgctgctgtt ataaatggag acaggtggtt tctcaatcga tttaccacaa ctcttaatga  10740
ctttaacctt gtggctatga agtacaatta tgaacctcta acacaagacc atgttgacat  10800
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca cctttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
accttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
```

agaaatgctg gacaacaggg caaccttaca agctatagcc tcagagttta gttcccttcc 12120
atcatatgca gcttttgcta ctgctcaaga agcttatgag caggctgttg ctaatggtga 12180
ttctgaagtt gttcttaaaa agttgaagaa gtctttgaat gtggctaaat ctgaatttga 12240
ccgtgatgca gccatgcaac gtaagttgga aaagatggct gatcaagcta tgacccaaat 12300
gtataaacag gctagatctg aggacaagag ggcaaaagtt actagtgcta tgcagacaat 12360
gcttttcact atgcttagaa agttggataa tgatgcactc aacaacatta tcaacaatgc 12420
aagagatggt tgtgttccct tgaacataat acctcttaca acagcagcca aactaatggt 12480
tgtcatacca gactataaca catataaaaa tacgtgtgat ggtacaacat ttacttatgc 12540
atcagcattg tgggaaatcc aacaggttgt agatgcagat agtaaaattg ttcaacttag 12600
tgaaattagt atggacaatt cacctaattt agcatggcct cttattgtaa cagctttaag 12660
ggccaattct gctgtcaaat tacagaataa tgagcttagt cctgttgcac tacgacagat 12720
gtcttgtgct gccggtacta cacaaactgc ttgcactgat gacaatgcgt tagcttacta 12780
caacacaaca aagggaggta ggtttgtact tgcactgtta tccgatttac aggatttgaa 12840
atgggctaga ttccctaaga gtgatggaac tggtactatc tatacagaac tggaaccacc 12900
ttgtaggttt gttacagaca cacctaaagg tcctaaagtg aagtatttat actttattaa 12960
aggattaaac aacctaaata gaggtatggt acttggtagt ttagctgcca cagtacgtct 13020
acaagctggt aatgcaacag aagtgcctgc caattcaact gtattatctt tctgtgcttt 13080
tgctgtagat gctgctaaag cttacaaaga ttatctagct agtgggggac aaccaatcac 13140
taattgtgtt aagatgttgt gtacacacac tggtactggt caggcaataa cagttacacc 13200
ggaagccaat atggatcaag aatcctttgg tggtgcatcg tgttgtctgt actgccgttg 13260
ccacatagat catccaaatc ctaaaggatt ttgtgactta aaaggtaagt atgtacaaat 13320
acctacaact tgtgctaatg accctgtggg ttttacactt aaaaacacag tctgtaccgt 13380
ctgcggtatg tggaaaggtt atggctgtag ttgtgatcaa ctccgcgaac ccatgcttca 13440
gtcagctgat gcacaatcgt ttttaaacgg gtttgcggtg taagtgcagc ccgtcttaca 13500
ccgtgcggca caggcactag tactgatgtc gtatacaggg cttttgacat ctacaatgat 13560
aaagtagctg gttttgctaa attcctaaaa actaattgtt gtcgcttcca agaaaaggac 13620
gaagatgaca atttaattga ttcttacttt gtagttaaga gacacacttt ctctaactac 13680
caacatgaag aaacaattta taatttactt aaggattgtc cagctgttgc taaacatgac 13740
ttctttaagt ttagaataga cggtgacatg gtaccacata tatcacgtca acgtcttact 13800
aaatacacaa tggcagacct cgtctatgct ttaaggcatt ttgatgaagg taattgtgac 13860
acattaaaag aaatacttgt cacatacaat tgttgtgatg atgattattt caataaaaag 13920
gactggtatg attttgtaga aaacccagat atattacgcg tatacgccaa cttaggtgaa 13980
cgtgtacgcc aagctttgtt aaaaacagta caattctgtg atgccatgcg aaatgctggt 14040
attgttggtg tactgacatt agataatcaa gatctcaatg gtaactggta tgatttcggt 14100
gatttcatac aaaccacgcc aggtagtgga gttcctgttg tagattctta ttattcattg 14160
ttaatgccta tattaacctt gaccagggct ttaactgcag agtcacatgt tgacactgac 14220
ttaacaaagc cttacattaa gtgggatttg ttaaaatatg acttcacgga agagaggtta 14280
aaactctttg accgttattt taaatattgg gatcagacat accacccaaa ttgtgttaac 14340
tgtttggatg acagatgcat tctgcattgt gcaaacttta atgttttatt ctctacagtg 14400

```
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
```

```
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
```

```
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtctttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat ttatctctt  21480
cttagtaaag gtagacttat aattagagaa aacaacagag ttgttatttc tagtgatgtt  21540
```

```
cttgttaaca actaaacgaa caatgtttgt ttttcttgtt ttattgccac tagtctctag  21600
tcagtgtgtt aatcttacaa ccagaactca attacccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt taataggggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
```

acaagacaaa aacacccaag aagtttttgc acaagtcaaa caaatttaca aaacaccacc 23940
aattaaagat tttggtggtt ttaatttttc acaaatatta ccagatccat caaaaccaag 24000
caagaggtca tttattgaag atctactttt caacaaagtg acacttgcag atgctggctt 24060
catcaaacaa tatggtgatt gccttggtga tattgctgct agagacctca tttgtgcaca 24120
aaagtttaac ggccttactg ttttgccacc tttgctcaca gatgaaatga ttgctcaata 24180
cacttctgca ctgttagcgg gtacaatcac ttctggttgg acctttggtg caggtgctgc 24240
attacaaata ccatttgcta tgcaaatggc ttataggttt aatggtattg gagttacaca 24300
gaatgttctc tatgagaacc aaaaattgat tgccaaccaa tttaatagtg ctattggcaa 24360
aattcaagac tcactttctt ccacagcaag tgcacttgga aaacttcaag atgtggtcaa 24420
ccaaaatgca caagctttaa acacgcttgt taaacaactt agctccaatt ttggtgcaat 24480
ttcaagtgtt ttaaatgata tcctttcacg tcttgacaaa gttgaggctg aagtgcaaat 24540
tgataggttg atcacaggca gacttcaaag tttgcagaca tatgtgactc aacaattaat 24600
tagagctgca gaaatcagag cttctgctaa tcttgctgct actaaaatgt cagagtgtgt 24660
acttggacaa tcaaaaagag ttgatttttg tggaaagggc tatcatctta tgtccttccc 24720
tcagtcagca cctcatggtg tagtcttctt gcatgtgact tatgtccctg cacaagaaaa 24780
gaacttcaca actgctcctg ccatttgtca tgatggaaaa gcacactttc ctcgtgaagg 24840
tgtctttgtt tcaaatggca cacactggtt tgtaacacaa aggaattttt atgaaccaca 24900
aatcattact acagacaaca catttgtgtc tggtaactgt gatgttgtaa taggaattgt 24960
caacaacaca gtttatgatc ctttgcaacc tgaattagac tcattcaagg aggagttaga 25020
taaatatttt aagaatcata catcaccaga tgttgattta ggtgacatct ctggcattaa 25080
tgcttcagtt gtaaacattc aaaaagaaat tgaccgcctc aatgaggttg ccaagaattt 25140
aaatgaatct ctcatcgatc tccaagaact tggaaagtat gagcagtata taaaatggcc 25200
atggtacatt tggctaggtt ttatagctgg cttgattgcc atagtaatgg tgacaattat 25260
gctttgctgt atgaccagtt gctgtagttg tctcaagggc tgttgttctt gtggatcctg 25320
ctgcaaattt gatgaagacg actctgagcc agtgctcaaa ggagtcaaat tacattacac 25380
ataaacgaac ttatggattt gtttatgaga atcttcacaa ttggaactgt aactttgaag 25440
caaggtgaaa tcaaggatgc tactccttca gattttgttc gcgctactgc aacgataccg 25500
atacaagcct cactcccttt cggatggctt attgttggcg ttgcacttct tgctgttttt 25560
cagagcgctt ccaaaatcat aaccctcaaa aagagatggc aactagcact ctccaagggt 25620
gttcactttg tttgcaactt gctgttgttg tttgtaacag tttactcaca ccttttgctc 25680
gttgctgctg gccttgaagc cccttttctc tatctttatg ctttagtcta cttcttgcag 25740
agtataaact ttgtaagaat aataatgagg ctttggcttt gctggaaatg ccgttccaaa 25800
aacccattac tttatgatgc caactatttt ctttgctggc atactaattg ttacgactat 25860
tgtatacctt acaatagtgt aacttcttca attgtcatta cttcaggtga tggcacaaca 25920
agtcctattt ctgaacatga ctaccagatt ggtggttata ctgaaaaatg ggaatctgga 25980
gtaaaagact gtgttgtatt acacagttac ttcacttcag actattacca gctgtactca 26040
actcaattga gtacagacac tggtgttgaa catgttacct tcttcatcta caataaaatt 26100
gttgatgagc ctgaagaaca tgtccaaatt cacacaatcg acggttcatc cggagttgtt 26160
aatccagtaa tggaaccaat ttatgatgaa ccgacgacga ctactagcgt gcctttgtaa 26220
gcacaagctg atgagtacga acttatgtac tcattcgttt cggaagagac aggtacgtta 26280
atagttaata gcgtacttct ttttcttgct ttcgtggtat tcttgctagt tacactagcc 26340
atccttactg cgcttcgatt gtgtgcgtac tgctgcaata ttgttaacgt gagtcttgta 26400
aaaccttctt tttacgttta ctctcgtgtt aaaaatctga attcttctag agttcctgat 26460
cttctggtct aaacgaacta aatattatat tagtttttct gtttggaact ttaattttag 26520
ccatggcaga ttccaacggt actattaccg ttgaagagct taaaaagctc cttgaacaat 26580
ggaacctagt aataggtttc ctattcctta catggatttg tcttctacaa tttgcctatg 26640
ccaacaggaa taggtttttg tatataatta agttaatttt cctctggctg ttatggccag 26700
taactttagc ttgttttgtg cttgctgctg tttacagaat aaattggatc accggtggaa 26760
ttgctatcgc aatggcttgt cttgtaggct tgatgtggct cagctacttc attgcttctt 26820
tcagactgtt tgcgcgtacg cgttccatgt ggtcattcaa tccagaaact aacattcttc 26880
tcaacgtgcc actccatggc actattctga ccagaccgct tctagaaagt gaactcgtaa 26940
tcggagctgt gatccttcgt ggacatcttc gtattgctgg acaccatcta ggacgctgtg 27000
acatcaagga cctgcctaaa gaaatcactg ttgctacatc acgaacgctt tcttattaca 27060
aattgggagc ttcgcagcgt gtagcaggtg actcaggttt tgctgcatac agtcgctaca 27120
ggattggcaa ctataaatta aacacagacc attccagtag cagtgacaat attgctttgc 27180
ttgtacagta agtgacaaca gatgtttcat ctcgttgact ttcaggttac tatagcagag 27240
atattactaa ttattatgag gacttttaaa gtttccattt ggaatcttga ttacatcata 27300
aacctcataa ttaaaaattt atctaagtca ctaactgaga ataaatattc tcaattagat 27360
gaagagcaac caatggagat tgattaaacg aacatgaaaa ttattctttt cttggcactg 27420
ataacactcg ctacttgtga gctttatcac taccaagagt gtgttagagg tacaacagta 27480
cttttaaaag aaccttgctc ttctggaaca tacgagggca attcaccatt tcatcctcta 27540
gctgataaca aatttgcact gacttgcttt agcactcaat ttgcttttgc ttgtcctgac 27600
ggcgtaaaac acgtctatca gttacgtgcc agatcagttt cacctaaact gttcatcaga 27660
caagaggaag ttcaagaact ttactctcca atttttctta ttgttgcggc aatagtgttt 27720
ataacacttt gcttcacact caaaagaaag acagaatgat tgaactttca ttaattgact 27780
tctatttgtg ctttttagcc tttctgctat tccttgtttt aattatgctt attatctttt 27840
ggttctcact tgaactgcaa gatcataatg aaacttgtca cgcctaaacg aacatgaaat 27900
ttcttgtttt cttaggaatc atcacaactg tagctgcatt tcaccaagaa tgtagtttac 27960
agtcatgtac tcaacatcaa ccatatgtag ttgatgaccc gtgtcctatt cacttctatt 28020
ctaaatggta tattagagta ggagctagaa aatcagcacc tttaattgaa ttgtgcgtgg 28080
atgaggctgg ttctaaatca cccattcagt acatcgatat cggtaattat acagtttcct 28140
gtttaccttt tacaattaat tgccaggaac ctaaattggg tagtcttgta gtgcgttgtt 28200
cgttctatga agacttttta gagtatcatg acgttcgtgt tgttttagat ttcatctaaa 28260
cgaacaaact aaaatgtctg ataatggacc ccaaaatcag cgaaatgcac cccgcattac 28320
gtttggtgga ccctcagatt caactggcag taaccagaat ggagaacgca gtggggcgcg 28380
atcaaaacaa cgtcggcccc aaggtttacc caataatact gcgtcttggt tcaccgctct 28440
cactcaacat ggcaaggaag accttaaatt ccctcgagga caaggcgttc caattaacac 28500
caatagcagt ccagatgacc aaattggcta ctaccgaaga gctaccagac gaattcgtgg 28560
tggtgacggt aaaatgaaag atctcagtcc aagatggtat ttctactacc taggaactgg 28620

-continued

```
gccagaagct ggacttccct atggtgctaa caaagacggc atcatatggg ttgcaactga  28680
gggagccttg aatacaccaa aagatcacat tggcacccgc aatcctgcta acaatgctgc  28740
aatcgtgcta caacttcctc aaggaacaac attgccaaaa ggcttctacg cagaagggag  28800
cagaggcggc agtcaagcct cttctcgttc ctcatcacgt agtcgcaaca gttcaagaaa  28860
ttcaactcca ggcagcagta ggggaacttc tcctgctaga atggctggca atggcggtga  28920
tgctgctctt gctttgctgc tgcttgacag attgaaccag cttgagagca aaatgtctgg  28980
taaaggccaa caacaacaag gccaaactgt cactaagaaa tctgctgctg aggcttctaa  29040
gaagcctcgg caaaaacgta ctgccactaa agcatacaat gtaacacaag ctttcggcag  29100
acgtggtcca gaacaaaccc aaggaaattt tggggaccag gaactaatca gacaaggaac  29160
tgattacaaa cattggccgc aaattgcaca atttgccccc agcgcttcag cgttcttcgg  29220
aatgtcgcgc attggcatgg aagtcacacc ttcgggaacg tggttgacct acacaggtgc  29280
catcaaattg gatgacaaag atccaaattt caaagatcaa gtcattttgc tgaataagca  29340
tattgacgca tacaaaacat tcccaccaac agagcctaaa aaggacaaaa agaagaaggc  29400
tgatgaaact caagccttac cgcagagaca gaagaaacag caaactgtga ctcttcttcc  29460
tgctgcagat ttggatgatt tctccaaaca attgcaacaa tccatgagca gtgctgactc  29520
aactcaggcc taaactcatg cagaccacac aaggcagatg ggctatataa acgttttcgc  29580
ttttccgttt acgatatata gtctactctt gtgcagaatg aattctcgta actacatagc  29640
acaagtagat gtagttaact ttaatctcac atagcaatct ttaatcagtg tgtaacatta  29700
gggaggactt gaaagagcca ccacattttc accgaggcca cgcggagtac gatcgagtgt  29760
acagtgaaca atgctaggga gagctgccta tatggaagag ccctaatgtg taaaattaat  29820
tttagtagtg ctatccccat gtgattttaa tagcttctta ggagaatgac aaaaaaaaaa  29880
aaaaaaaaaa aaaaaaaaaa aaa                                          29903
```

<210> SEQ ID NO 17
<211> LENGTH: 1273
<212> TYPE: PRT
<213> ORGANISM: Severe acute respiratory syndrome coronavirus 2

<400> SEQUENCE: 17

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140
```

-continued

```
Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
```

-continued

```
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990
```

```
Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140

Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270
```

<210> SEQ ID NO 18
<211> LENGTH: 75
<212> TYPE: PRT
<213> ORGANISM: Severe acute respiratory syndrome coronavirus 2

<400> SEQUENCE: 18

```
Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Ser Phe Tyr Val Tyr Ser Arg Val Lys Asn
    50                  55                  60

Leu Asn Ser Ser Arg Val Pro Asp Leu Leu Val
```

65 70 75

<210> SEQ ID NO 19
<211> LENGTH: 222
<212> TYPE: PRT
<213> ORGANISM: Severe acute respiratory syndrome coronavirus 2

<400> SEQUENCE: 19

Met Ala Asp Ser Asn Gly Thr Ile Thr Val Glu Glu Leu Lys Lys Leu
1 5 10 15

Leu Glu Gln Trp Asn Leu Val Ile Gly Phe Leu Phe Leu Thr Trp Ile
20 25 30

Cys Leu Leu Gln Phe Ala Tyr Ala Asn Arg Asn Arg Phe Leu Tyr Ile
35 40 45

Ile Lys Leu Ile Phe Leu Trp Leu Leu Trp Pro Val Thr Leu Ala Cys
50 55 60

Phe Val Leu Ala Ala Val Tyr Arg Ile Asn Trp Ile Thr Gly Gly Ile
65 70 75 80

Ala Ile Ala Met Ala Cys Leu Val Gly Leu Met Trp Leu Ser Tyr Phe
85 90 95

Ile Ala Ser Phe Arg Leu Phe Ala Arg Thr Arg Ser Met Trp Ser Phe
100 105 110

Asn Pro Glu Thr Asn Ile Leu Leu Asn Val Pro Leu His Gly Thr Ile
115 120 125

Leu Thr Arg Pro Leu Leu Glu Ser Glu Leu Val Ile Gly Ala Val Ile
130 135 140

Leu Arg Gly His Leu Arg Ile Ala Gly His His Leu Gly Arg Cys Asp
145 150 155 160

Ile Lys Asp Leu Pro Lys Glu Ile Thr Val Ala Thr Ser Arg Thr Leu
165 170 175

Ser Tyr Tyr Lys Leu Gly Ala Ser Gln Arg Val Ala Gly Asp Ser Gly
180 185 190

Phe Ala Ala Tyr Ser Arg Tyr Arg Ile Gly Asn Tyr Lys Leu Asn Thr
195 200 205

Asp His Ser Ser Ser Ser Asp Asn Ile Ala Leu Leu Val Gln
210 215 220

<210> SEQ ID NO 20
<211> LENGTH: 419
<212> TYPE: PRT
<213> ORGANISM: Severe acute respiratory syndrome coronavirus 2

<400> SEQUENCE: 20

Met Ser Asp Asn Gly Pro Gln Asn Gln Arg Asn Ala Pro Arg Ile Thr
1 5 10 15

Phe Gly Gly Pro Ser Asp Ser Thr Gly Ser Asn Gln Asn Gly Glu Arg
20 25 30

Ser Gly Ala Arg Ser Lys Gln Arg Arg Pro Gln Gly Leu Pro Asn Asn
35 40 45

Thr Ala Ser Trp Phe Thr Ala Leu Thr Gln His Gly Lys Glu Asp Leu
50 55 60

Lys Phe Pro Arg Gly Gln Gly Val Pro Ile Asn Thr Asn Ser Ser Pro
65 70 75 80

Asp Asp Gln Ile Gly Tyr Tyr Arg Arg Ala Thr Arg Arg Ile Arg Gly
85 90 95

Gly Asp Gly Lys Met Lys Asp Leu Ser Pro Arg Trp Tyr Phe Tyr Tyr 100 105 110

Leu Gly Thr Gly Pro Glu Ala Gly Leu Pro Tyr Gly Ala Asn Lys Asp
115 120 125

Gly Ile Ile Trp Val Ala Thr Glu Gly Ala Leu Asn Thr Pro Lys Asp
130 135 140

His Ile Gly Thr Arg Asn Pro Ala Asn Asn Ala Ala Ile Val Leu Gln
145 150 155 160

Leu Pro Gln Gly Thr Thr Leu Pro Lys Gly Phe Tyr Ala Glu Gly Ser
165 170 175

Arg Gly Gly Ser Gln Ala Ser Ser Arg Ser Ser Ser Arg Ser Arg Asn
180 185 190

Ser Ser Arg Asn Ser Thr Pro Gly Ser Ser Arg Gly Thr Ser Pro Ala
195 200 205

Arg Met Ala Gly Asn Gly Gly Asp Ala Ala Leu Ala Leu Leu Leu Leu
210 215 220

Asp Arg Leu Asn Gln Leu Glu Ser Lys Met Ser Gly Lys Gly Gln Gln
225 230 235 240

Gln Gln Gly Gln Thr Val Thr Lys Lys Ser Ala Ala Glu Ala Ser Lys
245 250 255

Lys Pro Arg Gln Lys Arg Thr Ala Thr Lys Ala Tyr Asn Val Thr Gln
260 265 270

Ala Phe Gly Arg Arg Gly Pro Glu Gln Thr Gln Gly Asn Phe Gly Asp
275 280 285

Gln Glu Leu Ile Arg Gln Gly Thr Asp Tyr Lys His Trp Pro Gln Ile
290 295 300

Ala Gln Phe Ala Pro Ser Ala Ser Ala Phe Phe Gly Met Ser Arg Ile
305 310 315 320

Gly Met Glu Val Thr Pro Ser Gly Thr Trp Leu Thr Tyr Thr Gly Ala
325 330 335

Ile Lys Leu Asp Asp Lys Asp Pro Asn Phe Lys Asp Gln Val Ile Leu
340 345 350

Leu Asn Lys His Ile Asp Ala Tyr Lys Thr Phe Pro Pro Thr Glu Pro
355 360 365

Lys Lys Asp Lys Lys Lys Lys Ala Asp Glu Thr Gln Ala Leu Pro Gln
370 375 380

Arg Gln Lys Lys Gln Gln Thr Val Thr Leu Leu Pro Ala Ala Asp Leu
385 390 395 400

Asp Asp Phe Ser Lys Gln Leu Gln Gln Ser Met Ser Ser Ala Asp Ser
405 410 415

Thr Gln Ala

<210> SEQ ID NO 21
<211> LENGTH: 7096
<212> TYPE: PRT
<213> ORGANISM: Severe acute respiratory syndrome coronavirus 2

<400> SEQUENCE: 21

Met Glu Ser Leu Val Pro Gly Phe Asn Glu Lys Thr His Val Gln Leu
1 5 10 15

Ser Leu Pro Val Leu Gln Val Arg Asp Val Leu Val Arg Gly Phe Gly
20 25 30

Asp Ser Val Glu Glu Val Leu Ser Glu Ala Arg Gln His Leu Lys Asp
35 40 45

Gly Thr Cys Gly Leu Val Glu Val Glu Lys Gly Val Leu Pro Gln Leu

```
    50                  55                  60

Glu Gln Pro Tyr Val Phe Ile Lys Arg Ser Asp Ala Arg Thr Ala Pro
65                  70                  75                  80

His Gly His Val Met Val Glu Leu Val Ala Glu Leu Glu Gly Ile Gln
                85                  90                  95

Tyr Gly Arg Ser Gly Glu Thr Leu Gly Val Leu Val Pro His Val Gly
            100                 105                 110

Glu Ile Pro Val Ala Tyr Arg Lys Val Leu Leu Arg Lys Asn Gly Asn
        115                 120                 125

Lys Gly Ala Gly Gly His Ser Tyr Gly Ala Asp Leu Lys Ser Phe Asp
    130                 135                 140

Leu Gly Asp Glu Leu Gly Thr Asp Pro Tyr Glu Asp Phe Gln Glu Asn
145                 150                 155                 160

Trp Asn Thr Lys His Ser Ser Gly Val Thr Arg Glu Leu Met Arg Glu
                165                 170                 175

Leu Asn Gly Gly Ala Tyr Thr Arg Tyr Val Asp Asn Asn Phe Cys Gly
            180                 185                 190

Pro Asp Gly Tyr Pro Leu Glu Cys Ile Lys Asp Leu Leu Ala Arg Ala
        195                 200                 205

Gly Lys Ala Ser Cys Thr Leu Ser Glu Gln Leu Asp Phe Ile Asp Thr
    210                 215                 220

Lys Arg Gly Val Tyr Cys Cys Arg Glu His Glu His Glu Ile Ala Trp
225                 230                 235                 240

Tyr Thr Glu Arg Ser Glu Lys Ser Tyr Glu Leu Gln Thr Pro Phe Glu
                245                 250                 255

Ile Lys Leu Ala Lys Lys Phe Asp Thr Phe Asn Gly Glu Cys Pro Asn
            260                 265                 270

Phe Val Phe Pro Leu Asn Ser Ile Ile Lys Thr Ile Gln Pro Arg Val
        275                 280                 285

Glu Lys Lys Lys Leu Asp Gly Phe Met Gly Arg Ile Arg Ser Val Tyr
    290                 295                 300

Pro Val Ala Ser Pro Asn Glu Cys Asn Gln Met Cys Leu Ser Thr Leu
305                 310                 315                 320

Met Lys Cys Asp His Cys Gly Glu Thr Ser Trp Gln Thr Gly Asp Phe
                325                 330                 335

Val Lys Ala Thr Cys Glu Phe Cys Gly Thr Glu Asn Leu Thr Lys Glu
            340                 345                 350

Gly Ala Thr Thr Cys Gly Tyr Leu Pro Gln Asn Ala Val Val Lys Ile
        355                 360                 365

Tyr Cys Pro Ala Cys His Asn Ser Glu Val Gly Pro Glu His Ser Leu
    370                 375                 380

Ala Glu Tyr His Asn Glu Ser Gly Leu Lys Thr Ile Leu Arg Lys Gly
385                 390                 395                 400

Gly Arg Thr Ile Ala Phe Gly Gly Cys Val Phe Ser Tyr Val Gly Cys
                405                 410                 415

His Asn Lys Cys Ala Tyr Trp Val Pro Arg Ala Ser Ala Asn Ile Gly
            420                 425                 430

Cys Asn His Thr Gly Val Val Gly Glu Gly Ser Glu Gly Leu Asn Asp
        435                 440                 445

Asn Leu Leu Glu Ile Leu Gln Lys Glu Lys Val Asn Ile Asn Ile Val
    450                 455                 460

Gly Asp Phe Lys Leu Asn Glu Glu Ile Ala Ile Ile Leu Ala Ser Phe
465                 470                 475                 480
```

```
Ser Ala Ser Thr Ser Ala Phe Val Glu Thr Val Lys Gly Leu Asp Tyr
                485                 490                 495

Lys Ala Phe Lys Gln Ile Val Glu Ser Cys Gly Asn Phe Lys Val Thr
            500                 505                 510

Lys Gly Lys Ala Lys Lys Gly Ala Trp Asn Ile Gly Glu Gln Lys Ser
        515                 520                 525

Ile Leu Ser Pro Leu Tyr Ala Phe Ala Ser Glu Ala Ala Arg Val Val
    530                 535                 540

Arg Ser Ile Phe Ser Arg Thr Leu Glu Thr Ala Gln Asn Ser Val Arg
545                 550                 555                 560

Val Leu Gln Lys Ala Ala Ile Thr Ile Leu Asp Gly Ile Ser Gln Tyr
                565                 570                 575

Ser Leu Arg Leu Ile Asp Ala Met Met Phe Thr Ser Asp Leu Ala Thr
            580                 585                 590

Asn Asn Leu Val Val Met Ala Tyr Ile Thr Gly Gly Val Val Gln Leu
        595                 600                 605

Thr Ser Gln Trp Leu Thr Asn Ile Phe Gly Thr Val Tyr Glu Lys Leu
    610                 615                 620

Lys Pro Val Leu Asp Trp Leu Glu Glu Lys Phe Lys Glu Gly Val Glu
625                 630                 635                 640

Phe Leu Arg Asp Gly Trp Glu Ile Val Lys Phe Ile Ser Thr Cys Ala
                645                 650                 655

Cys Glu Ile Val Gly Gly Gln Ile Val Thr Cys Ala Lys Glu Ile Lys
            660                 665                 670

Glu Ser Val Gln Thr Phe Phe Lys Leu Val Asn Lys Phe Leu Ala Leu
        675                 680                 685

Cys Ala Asp Ser Ile Ile Ile Gly Gly Ala Lys Leu Lys Ala Leu Asn
    690                 695                 700

Leu Gly Glu Thr Phe Val Thr His Ser Lys Gly Leu Tyr Arg Lys Cys
705                 710                 715                 720

Val Lys Ser Arg Glu Glu Thr Gly Leu Leu Met Pro Leu Lys Ala Pro
                725                 730                 735

Lys Glu Ile Ile Phe Leu Glu Gly Glu Thr Leu Pro Thr Glu Val Leu
            740                 745                 750

Thr Glu Glu Val Val Leu Lys Thr Gly Asp Leu Gln Pro Leu Glu Gln
        755                 760                 765

Pro Thr Ser Glu Ala Val Glu Ala Pro Leu Val Gly Thr Pro Val Cys
    770                 775                 780

Ile Asn Gly Leu Met Leu Leu Glu Ile Lys Asp Thr Glu Lys Tyr Cys
785                 790                 795                 800

Ala Leu Ala Pro Asn Met Met Val Thr Asn Asn Thr Phe Thr Leu Lys
                805                 810                 815

Gly Gly Ala Pro Thr Lys Val Thr Phe Gly Asp Asp Thr Val Ile Glu
            820                 825                 830

Val Gln Gly Tyr Lys Ser Val Asn Ile Thr Phe Glu Leu Asp Glu Arg
        835                 840                 845

Ile Asp Lys Val Leu Asn Glu Lys Cys Ser Ala Tyr Thr Val Glu Leu
    850                 855                 860

Gly Thr Glu Val Asn Glu Phe Ala Cys Val Val Ala Asp Ala Val Ile
865                 870                 875                 880

Lys Thr Leu Gln Pro Val Ser Glu Leu Leu Thr Pro Leu Gly Ile Asp
                885                 890                 895
```

```
Leu Asp Glu Trp Ser Met Ala Thr Tyr Tyr Leu Phe Asp Glu Ser Gly
            900                 905                 910

Glu Phe Lys Leu Ala Ser His Met Tyr Cys Ser Phe Tyr Pro Pro Asp
        915                 920                 925

Glu Asp Glu Glu Glu Gly Asp Cys Glu Glu Glu Phe Glu Pro Ser
    930                 935                 940

Thr Gln Tyr Glu Tyr Gly Thr Glu Asp Asp Tyr Gln Gly Lys Pro Leu
945                 950                 955                 960

Glu Phe Gly Ala Thr Ser Ala Ala Leu Gln Pro Glu Glu Glu Gln Glu
                965                 970                 975

Glu Asp Trp Leu Asp Asp Asp Ser Gln Gln Thr Val Gly Gln Gln Asp
            980                 985                 990

Gly Ser Glu Asp Asn Gln Thr Thr  Thr Ile Gln Thr Ile  Val Glu Val
        995                 1000                1005

Gln Pro  Gln Leu Glu Met Glu  Leu Thr Pro Val Val  Gln Thr Ile
    1010                 1015                 1020

Glu Val  Asn Ser Phe Ser Gly  Tyr Leu Lys Leu Thr  Asp Asn Val
    1025                 1030                 1035

Tyr Ile  Lys Asn Ala Asp Ile  Val Glu Glu Ala Lys  Lys Val Lys
    1040                 1045                 1050

Pro Thr  Val Val Val Asn Ala  Ala Asn Val Tyr Leu  Lys His Gly
    1055                 1060                 1065

Gly Gly  Val Ala Gly Ala Leu  Asn Lys Ala Thr Asn  Asn Ala Met
    1070                 1075                 1080

Gln Val  Glu Ser Asp Asp Tyr  Ile Ala Thr Asn Gly  Pro Leu Lys
    1085                 1090                 1095

Val Gly  Gly Ser Cys Val Leu  Ser Gly His Asn Leu  Ala Lys His
    1100                 1105                 1110

Cys Leu  His Val Val Gly Pro  Asn Val Asn Lys Gly  Glu Asp Ile
    1115                 1120                 1125

Gln Leu  Leu Lys Ser Ala Tyr  Glu Asn Phe Asn Gln  His Glu Val
    1130                 1135                 1140

Leu Leu  Ala Pro Leu Leu Ser  Ala Gly Ile Phe Gly  Ala Asp Pro
    1145                 1150                 1155

Ile His  Ser Leu Arg Val Cys  Val Asp Thr Val Arg  Thr Asn Val
    1160                 1165                 1170

Tyr Leu  Ala Val Phe Asp Lys  Asn Leu Tyr Asp Lys  Leu Val Ser
    1175                 1180                 1185

Ser Phe  Leu Glu Met Lys Ser  Glu Lys Gln Val Glu  Gln Lys Ile
    1190                 1195                 1200

Ala Glu  Ile Pro Lys Glu Glu  Val Lys Pro Phe Ile  Thr Glu Ser
    1205                 1210                 1215

Lys Pro  Ser Val Glu Gln Arg  Lys Gln Asp Asp Lys  Lys Ile Lys
    1220                 1225                 1230

Ala Cys  Val Glu Glu Val Thr  Thr Thr Leu Glu Glu  Thr Lys Phe
    1235                 1240                 1245

Leu Thr  Glu Asn Leu Leu Leu  Tyr Ile Asp Ile Asn  Gly Asn Leu
    1250                 1255                 1260

His Pro  Asp Ser Ala Thr Leu  Val Ser Asp Ile Asp  Ile Thr Phe
    1265                 1270                 1275

Leu Lys  Lys Asp Ala Pro Tyr  Ile Val Gly Asp Val  Val Gln Glu
    1280                 1285                 1290

Gly Val  Leu Thr Ala Val Val  Ile Pro Thr Lys Lys  Ala Gly Gly
```

```
    1295                1300                1305

Thr Thr  Glu Met Leu Ala Lys  Ala Leu Arg Lys Val  Pro Thr Asp
    1310                1315                1320

Asn Tyr  Ile Thr Thr Tyr Pro  Gly Gln Gly Leu Asn  Gly Tyr Thr
    1325                1330                1335

Val Glu  Glu Ala Lys Thr Val  Leu Lys Lys Cys Lys  Ser Ala Phe
    1340                1345                1350

Tyr Ile  Leu Pro Ser Ile Ile  Ser Asn Glu Lys Gln  Glu Ile Leu
    1355                1360                1365

Gly Thr  Val Ser Trp Asn Leu  Arg Glu Met Leu Ala  His Ala Glu
    1370                1375                1380

Glu Thr  Arg Lys Leu Met Pro  Val Cys Val Glu Thr  Lys Ala Ile
    1385                1390                1395

Val Ser  Thr Ile Gln Arg Lys  Tyr Lys Gly Ile Lys  Ile Gln Glu
    1400                1405                1410

Gly Val  Val Asp Tyr Gly Ala  Arg Phe Tyr Phe Tyr  Thr Ser Lys
    1415                1420                1425

Thr Thr  Val Ala Ser Leu Ile  Asn Thr Leu Asn Asp  Leu Asn Glu
    1430                1435                1440

Thr Leu  Val Thr Met Pro Leu  Gly Tyr Val Thr His  Gly Leu Asn
    1445                1450                1455

Leu Glu  Glu Ala Ala Arg Tyr  Met Arg Ser Leu Lys  Val Pro Ala
    1460                1465                1470

Thr Val  Ser Val Ser Ser Pro  Asp Ala Val Thr Ala  Tyr Asn Gly
    1475                1480                1485

Tyr Leu  Thr Ser Ser Ser Lys  Thr Pro Glu Glu His  Phe Ile Glu
    1490                1495                1500

Thr Ile  Ser Leu Ala Gly Ser  Tyr Lys Asp Trp Ser  Tyr Ser Gly
    1505                1510                1515

Gln Ser  Thr Gln Leu Gly Ile  Glu Phe Leu Lys Arg  Gly Asp Lys
    1520                1525                1530

Ser Val  Tyr Tyr Thr Ser Asn  Pro Thr Thr Phe His  Leu Asp Gly
    1535                1540                1545

Glu Val  Ile Thr Phe Asp Asn  Leu Lys Thr Leu Leu  Ser Leu Arg
    1550                1555                1560

Glu Val  Arg Thr Ile Lys Val  Phe Thr Thr Val Asp  Asn Ile Asn
    1565                1570                1575

Leu His  Thr Gln Val Val Asp  Met Ser Met Thr Tyr  Gly Gln Gln
    1580                1585                1590

Phe Gly  Pro Thr Tyr Leu Asp  Gly Ala Asp Val Thr  Lys Ile Lys
    1595                1600                1605

Pro His  Asn Ser His Glu Gly  Lys Thr Phe Tyr Val  Leu Pro Asn
    1610                1615                1620

Asp Asp  Thr Leu Arg Val Glu  Ala Phe Glu Tyr Tyr  His Thr Thr
    1625                1630                1635

Asp Pro  Ser Phe Leu Gly Arg  Tyr Met Ser Ala Leu  Asn His Thr
    1640                1645                1650

Lys Lys  Trp Lys Tyr Pro Gln  Val Asn Gly Leu Thr  Ser Ile Lys
    1655                1660                1665

Trp Ala  Asp Asn Asn Cys Tyr  Leu Ala Thr Ala Leu  Leu Thr Leu
    1670                1675                1680

Gln Gln  Ile Glu Leu Lys Phe  Asn Pro Pro Ala Leu  Gln Asp Ala
    1685                1690                1695
```

```
Tyr Tyr Arg Ala Arg Ala Gly Glu Ala Ala Asn Phe Cys Ala Leu
    1700                1705                1710

Ile Leu Ala Tyr Cys Asn Lys Thr Val Gly Glu Leu Gly Asp Val
    1715                1720                1725

Arg Glu Thr Met Ser Tyr Leu Phe Gln His Ala Asn Leu Asp Ser
    1730                1735                1740

Cys Lys Arg Val Leu Asn Val Val Cys Lys Thr Cys Gly Gln Gln
    1745                1750                1755

Gln Thr Thr Leu Lys Gly Val Glu Ala Val Met Tyr Met Gly Thr
    1760                1765                1770

Leu Ser Tyr Glu Gln Phe Lys Lys Gly Val Gln Ile Pro Cys Thr
    1775                1780                1785

Cys Gly Lys Gln Ala Thr Lys Tyr Leu Val Gln Gln Glu Ser Pro
    1790                1795                1800

Phe Val Met Met Ser Ala Pro Pro Ala Gln Tyr Glu Leu Lys His
    1805                1810                1815

Gly Thr Phe Thr Cys Ala Ser Glu Tyr Thr Gly Asn Tyr Gln Cys
    1820                1825                1830

Gly His Tyr Lys His Ile Thr Ser Lys Glu Thr Leu Tyr Cys Ile
    1835                1840                1845

Asp Gly Ala Leu Leu Thr Lys Ser Ser Glu Tyr Lys Gly Pro Ile
    1850                1855                1860

Thr Asp Val Phe Tyr Lys Glu Asn Ser Tyr Thr Thr Thr Ile Lys
    1865                1870                1875

Pro Val Thr Tyr Lys Leu Asp Gly Val Val Cys Thr Glu Ile Asp
    1880                1885                1890

Pro Lys Leu Asp Asn Tyr Tyr Lys Lys Asp Asn Ser Tyr Phe Thr
    1895                1900                1905

Glu Gln Pro Ile Asp Leu Val Pro Asn Gln Pro Tyr Pro Asn Ala
    1910                1915                1920

Ser Phe Asp Asn Phe Lys Phe Val Cys Asp Asn Ile Lys Phe Ala
    1925                1930                1935

Asp Asp Leu Asn Gln Leu Thr Gly Tyr Lys Lys Pro Ala Ser Arg
    1940                1945                1950

Glu Leu Lys Val Thr Phe Phe Pro Asp Leu Asn Gly Asp Val Val
    1955                1960                1965

Ala Ile Asp Tyr Lys His Tyr Thr Pro Ser Phe Lys Lys Gly Ala
    1970                1975                1980

Lys Leu Leu His Lys Pro Ile Val Trp His Val Asn Asn Ala Thr
    1985                1990                1995

Asn Lys Ala Thr Tyr Lys Pro Asn Thr Trp Cys Ile Arg Cys Leu
    2000                2005                2010

Trp Ser Thr Lys Pro Val Glu Thr Ser Asn Ser Phe Asp Val Leu
    2015                2020                2025

Lys Ser Glu Asp Ala Gln Gly Met Asp Asn Leu Ala Cys Glu Asp
    2030                2035                2040

Leu Lys Pro Val Ser Glu Glu Val Val Glu Asn Pro Thr Ile Gln
    2045                2050                2055

Lys Asp Val Leu Glu Cys Asn Val Lys Thr Thr Glu Val Val Gly
    2060                2065                2070

Asp Ile Ile Leu Lys Pro Ala Asn Asn Ser Leu Lys Ile Thr Glu
    2075                2080                2085
```

-continued

```
Glu Val  Gly His Thr Asp Leu  Met Ala Ala Tyr Val  Asp Asn Ser
    2090                 2095                 2100

Ser Leu  Thr Ile Lys Lys Pro  Asn Glu Leu Ser Arg  Val Leu Gly
    2105                 2110                 2115

Leu Lys  Thr Leu Ala Thr His  Gly Leu Ala Ala Val  Asn Ser Val
    2120                 2125                 2130

Pro Trp  Asp Thr Ile Ala Asn  Tyr Ala Lys Pro Phe  Leu Asn Lys
    2135                 2140                 2145

Val Val  Ser Thr Thr Thr Asn  Ile Val Thr Arg Cys  Leu Asn Arg
    2150                 2155                 2160

Val Cys  Thr Asn Tyr Met Pro  Tyr Phe Phe Thr Leu  Leu Leu Gln
    2165                 2170                 2175

Leu Cys  Thr Phe Thr Arg Ser  Thr Asn Ser Arg Ile  Lys Ala Ser
    2180                 2185                 2190

Met Pro  Thr Thr Ile Ala Lys  Asn Thr Val Lys Ser  Val Gly Lys
    2195                 2200                 2205

Phe Cys  Leu Glu Ala Ser Phe  Asn Tyr Leu Lys Ser  Pro Asn Phe
    2210                 2215                 2220

Ser Lys  Leu Ile Asn Ile Ile  Ile Trp Phe Leu Leu  Leu Ser Val
    2225                 2230                 2235

Cys Leu  Gly Ser Leu Ile Tyr  Ser Thr Ala Ala Leu  Gly Val Leu
    2240                 2245                 2250

Met Ser  Asn Leu Gly Met Pro  Ser Tyr Cys Thr Gly  Tyr Arg Glu
    2255                 2260                 2265

Gly Tyr  Leu Asn Ser Thr Asn  Val Thr Ile Ala Thr  Tyr Cys Thr
    2270                 2275                 2280

Gly Ser  Ile Pro Cys Ser Val  Cys Leu Ser Gly Leu  Asp Ser Leu
    2285                 2290                 2295

Asp Thr  Tyr Pro Ser Leu Glu  Thr Ile Gln Ile Thr  Ile Ser Ser
    2300                 2305                 2310

Phe Lys  Trp Asp Leu Thr Ala  Phe Gly Leu Val Ala  Glu Trp Phe
    2315                 2320                 2325

Leu Ala  Tyr Ile Leu Phe Thr  Arg Phe Phe Tyr Val  Leu Gly Leu
    2330                 2335                 2340

Ala Ala  Ile Met Gln Leu Phe  Phe Ser Tyr Phe Ala  Val His Phe
    2345                 2350                 2355

Ile Ser  Asn Ser Trp Leu Met  Trp Leu Ile Ile Asn  Leu Val Gln
    2360                 2365                 2370

Met Ala  Pro Ile Ser Ala Met  Val Arg Met Tyr Ile  Phe Phe Ala
    2375                 2380                 2385

Ser Phe  Tyr Tyr Val Trp Lys  Ser Tyr Val His Val  Val Asp Gly
    2390                 2395                 2400

Cys Asn  Ser Ser Thr Cys Met  Met Cys Tyr Lys Arg  Asn Arg Ala
    2405                 2410                 2415

Thr Arg  Val Glu Cys Thr Thr  Ile Val Asn Gly Val  Arg Arg Ser
    2420                 2425                 2430

Phe Tyr  Val Tyr Ala Asn Gly  Gly Lys Gly Phe Cys  Lys Leu His
    2435                 2440                 2445

Asn Trp  Asn Cys Val Asn Cys  Asp Thr Phe Cys Ala  Gly Ser Thr
    2450                 2455                 2460

Phe Ile  Ser Asp Glu Val Ala  Arg Asp Leu Ser Leu  Gln Phe Lys
    2465                 2470                 2475

Arg Pro  Ile Asn Pro Thr Asp  Gln Ser Ser Tyr Ile  Val Asp Ser
```

-continued

```
    2480                2485                2490

Val Thr  Val Lys Asn Gly Ser  Ile His Leu Tyr Phe  Asp Lys Ala
    2495                2500                2505

Gly Gln  Lys Thr Tyr Glu Arg  His Ser Leu Ser His  Phe Val Asn
    2510                2515                2520

Leu Asp  Asn Leu Arg Ala Asn  Asn Thr Lys Gly Ser  Leu Pro Ile
    2525                2530                2535

Asn Val  Ile Val Phe Asp Gly  Lys Ser Lys Cys Glu  Glu Ser Ser
    2540                2545                2550

Ala Lys  Ser Ala Ser Val Tyr  Tyr Ser Gln Leu Met  Cys Gln Pro
    2555                2560                2565

Ile Leu  Leu Leu Asp Gln Ala  Leu Val Ser Asp Val  Gly Asp Ser
    2570                2575                2580

Ala Glu  Val Ala Val Lys Met  Phe Asp Ala Tyr Val  Asn Thr Phe
    2585                2590                2595

Ser Ser  Thr Phe Asn Val Pro  Met Glu Lys Leu Lys  Thr Leu Val
    2600                2605                2610

Ala Thr  Ala Glu Ala Glu Leu  Ala Lys Asn Val Ser  Leu Asp Asn
    2615                2620                2625

Val Leu  Ser Thr Phe Ile Ser  Ala Ala Arg Gln Gly  Phe Val Asp
    2630                2635                2640

Ser Asp  Val Glu Thr Lys Asp  Val Val Glu Cys Leu  Lys Leu Ser
    2645                2650                2655

His Gln  Ser Asp Ile Glu Val  Thr Gly Asp Ser Cys  Asn Asn Tyr
    2660                2665                2670

Met Leu  Thr Tyr Asn Lys Val  Glu Asn Met Thr Pro  Arg Asp Leu
    2675                2680                2685

Gly Ala  Cys Ile Asp Cys Ser  Ala Arg His Ile Asn  Ala Gln Val
    2690                2695                2700

Ala Lys  Ser His Asn Ile Ala  Leu Ile Trp Asn Val  Lys Asp Phe
    2705                2710                2715

Met Ser  Leu Ser Glu Gln Leu  Arg Lys Gln Ile Arg  Ser Ala Ala
    2720                2725                2730

Lys Lys  Asn Asn Leu Pro Phe  Lys Leu Thr Cys Ala  Thr Thr Arg
    2735                2740                2745

Gln Val  Val Asn Val Val Thr  Thr Lys Ile Ala Leu  Lys Gly Gly
    2750                2755                2760

Lys Ile  Val Asn Asn Trp Leu  Lys Gln Leu Ile Lys  Val Thr Leu
    2765                2770                2775

Val Phe  Leu Phe Val Ala Ala  Ile Phe Tyr Leu Ile  Thr Pro Val
    2780                2785                2790

His Val  Met Ser Lys His Thr  Asp Phe Ser Ser Glu  Ile Ile Gly
    2795                2800                2805

Tyr Lys  Ala Ile Asp Gly Gly  Val Thr Arg Asp Ile  Ala Ser Thr
    2810                2815                2820

Asp Thr  Cys Phe Ala Asn Lys  His Ala Asp Phe Asp  Thr Trp Phe
    2825                2830                2835

Ser Gln  Arg Gly Gly Ser Tyr  Thr Asn Asp Lys Ala  Cys Pro Leu
    2840                2845                2850

Ile Ala  Ala Val Ile Thr Arg  Glu Val Gly Phe Val  Val Pro Gly
    2855                2860                2865

Leu Pro  Gly Thr Ile Leu Arg  Thr Thr Asn Gly Asp  Phe Leu His
    2870                2875                2880
```

```
Phe Leu Pro Arg Val Phe Ser Ala Val Gly Asn Ile Cys Tyr Thr
    2885                2890                2895

Pro Ser Lys Leu Ile Glu Tyr Thr Asp Phe Ala Thr Ser Ala Cys
    2900                2905                2910

Val Leu Ala Ala Glu Cys Thr Ile Phe Lys Asp Ala Ser Gly Lys
    2915                2920                2925

Pro Val Pro Tyr Cys Tyr Asp Thr Asn Val Leu Glu Gly Ser Val
    2930                2935                2940

Ala Tyr Glu Ser Leu Arg Pro Asp Thr Arg Tyr Val Leu Met Asp
    2945                2950                2955

Gly Ser Ile Ile Gln Phe Pro Asn Thr Tyr Leu Glu Gly Ser Val
    2960                2965                2970

Arg Val Val Thr Thr Phe Asp Ser Glu Tyr Cys Arg His Gly Thr
    2975                2980                2985

Cys Glu Arg Ser Glu Ala Gly Val Cys Val Ser Thr Ser Gly Arg
    2990                2995                3000

Trp Val Leu Asn Asn Asp Tyr Tyr Arg Ser Leu Pro Gly Val Phe
    3005                3010                3015

Cys Gly Val Asp Ala Val Asn Leu Leu Thr Asn Met Phe Thr Pro
    3020                3025                3030

Leu Ile Gln Pro Ile Gly Ala Leu Asp Ile Ser Ala Ser Ile Val
    3035                3040                3045

Ala Gly Gly Ile Val Ala Ile Val Val Thr Cys Leu Ala Tyr Tyr
    3050                3055                3060

Phe Met Arg Phe Arg Arg Ala Phe Gly Glu Tyr Ser His Val Val
    3065                3070                3075

Ala Phe Asn Thr Leu Leu Phe Leu Met Ser Phe Thr Val Leu Cys
    3080                3085                3090

Leu Thr Pro Val Tyr Ser Phe Leu Pro Gly Val Tyr Ser Val Ile
    3095                3100                3105

Tyr Leu Tyr Leu Thr Phe Tyr Leu Thr Asn Asp Val Ser Phe Leu
    3110                3115                3120

Ala His Ile Gln Trp Met Val Met Phe Thr Pro Leu Val Pro Phe
    3125                3130                3135

Trp Ile Thr Ile Ala Tyr Ile Ile Cys Ile Ser Thr Lys His Phe
    3140                3145                3150

Tyr Trp Phe Phe Ser Asn Tyr Leu Lys Arg Arg Val Val Phe Asn
    3155                3160                3165

Gly Val Ser Phe Ser Thr Phe Glu Glu Ala Ala Leu Cys Thr Phe
    3170                3175                3180

Leu Leu Asn Lys Glu Met Tyr Leu Lys Leu Arg Ser Asp Val Leu
    3185                3190                3195

Leu Pro Leu Thr Gln Tyr Asn Arg Tyr Leu Ala Leu Tyr Asn Lys
    3200                3205                3210

Tyr Lys Tyr Phe Ser Gly Ala Met Asp Thr Thr Ser Tyr Arg Glu
    3215                3220                3225

Ala Ala Cys Cys His Leu Ala Lys Ala Leu Asn Asp Phe Ser Asn
    3230                3235                3240

Ser Gly Ser Asp Val Leu Tyr Gln Pro Pro Gln Thr Ser Ile Thr
    3245                3250                3255

Ser Ala Val Leu Gln Ser Gly Phe Arg Lys Met Ala Phe Pro Ser
    3260                3265                3270
```

```
Gly Lys  Val Glu Gly Cys Met  Val Gln Val Thr Cys  Gly Thr Thr
    3275                 3280                 3285

Thr Leu  Asn Gly Leu Trp Leu  Asp Asp Val Val Tyr  Cys Pro Arg
    3290                 3295                 3300

His Val  Ile Cys Thr Ser Glu  Asp Met Leu Asn Pro  Asn Tyr Glu
    3305                 3310                 3315

Asp Leu  Leu Ile Arg Lys Ser  Asn His Asn Phe Leu  Val Gln Ala
    3320                 3325                 3330

Gly Asn  Val Gln Leu Arg Val  Ile Gly His Ser Met  Gln Asn Cys
    3335                 3340                 3345

Val Leu  Lys Leu Lys Val Asp  Thr Ala Asn Pro Lys  Thr Pro Lys
    3350                 3355                 3360

Tyr Lys  Phe Val Arg Ile Gln  Pro Gly Gln Thr Phe  Ser Val Leu
    3365                 3370                 3375

Ala Cys  Tyr Asn Gly Ser Pro  Ser Gly Val Tyr Gln  Cys Ala Met
    3380                 3385                 3390

Arg Pro  Asn Phe Thr Ile Lys  Gly Ser Phe Leu Asn  Gly Ser Cys
    3395                 3400                 3405

Gly Ser  Val Gly Phe Asn Ile  Asp Tyr Asp Cys Val  Ser Phe Cys
    3410                 3415                 3420

Tyr Met  His His Met Glu Leu  Pro Thr Gly Val His  Ala Gly Thr
    3425                 3430                 3435

Asp Leu  Glu Gly Asn Phe Tyr  Gly Pro Phe Val Asp  Arg Gln Thr
    3440                 3445                 3450

Ala Gln  Ala Ala Gly Thr Asp  Thr Thr Ile Thr Val  Asn Val Leu
    3455                 3460                 3465

Ala Trp  Leu Tyr Ala Ala Val  Ile Asn Gly Asp Arg  Trp Phe Leu
    3470                 3475                 3480

Asn Arg  Phe Thr Thr Thr Leu  Asn Asp Phe Asn Leu  Val Ala Met
    3485                 3490                 3495

Lys Tyr  Asn Tyr Glu Pro Leu  Thr Gln Asp His Val  Asp Ile Leu
    3500                 3505                 3510

Gly Pro  Leu Ser Ala Gln Thr  Gly Ile Ala Val Leu  Asp Met Cys
    3515                 3520                 3525

Ala Ser  Leu Lys Glu Leu Leu  Gln Asn Gly Met Asn  Gly Arg Thr
    3530                 3535                 3540

Ile Leu  Gly Ser Ala Leu Leu  Glu Asp Glu Phe Thr  Pro Phe Asp
    3545                 3550                 3555

Val Val  Arg Gln Cys Ser Gly  Val Thr Phe Gln Ser  Ala Val Lys
    3560                 3565                 3570

Arg Thr  Ile Lys Gly Thr His  His Trp Leu Leu Leu  Thr Ile Leu
    3575                 3580                 3585

Thr Ser  Leu Leu Val Leu Val  Gln Ser Thr Gln Trp  Ser Leu Phe
    3590                 3595                 3600

Phe Phe  Leu Tyr Glu Asn Ala  Phe Leu Pro Phe Ala  Met Gly Ile
    3605                 3610                 3615

Ile Ala  Met Ser Ala Phe Ala  Met Met Phe Val Lys  His Lys His
    3620                 3625                 3630

Ala Phe  Leu Cys Leu Phe Leu  Leu Pro Ser Leu Ala  Thr Val Ala
    3635                 3640                 3645

Tyr Phe  Asn Met Val Tyr Met  Pro Ala Ser Trp Val  Met Arg Ile
    3650                 3655                 3660

Met Thr  Trp Leu Asp Met Val  Asp Thr Ser Leu Ser  Gly Phe Lys
```

```
    3665                3670                3675

Leu Lys Asp Cys Val Met Tyr Ala Ser Ala Val Val Leu Leu Ile
    3680                3685                3690

Leu Met Thr Ala Arg Thr Val Tyr Asp Asp Gly Ala Arg Arg Val
    3695                3700                3705

Trp Thr Leu Met Asn Val Leu Thr Leu Val Tyr Lys Val Tyr Tyr
    3710                3715                3720

Gly Asn Ala Leu Asp Gln Ala Ile Ser Met Trp Ala Leu Ile Ile
    3725                3730                3735

Ser Val Thr Ser Asn Tyr Ser Gly Val Val Thr Thr Val Met Phe
    3740                3745                3750

Leu Ala Arg Gly Ile Val Phe Met Cys Val Glu Tyr Cys Pro Ile
    3755                3760                3765

Phe Phe Ile Thr Gly Asn Thr Leu Gln Cys Ile Met Leu Val Tyr
    3770                3775                3780

Cys Phe Leu Gly Tyr Phe Cys Thr Cys Tyr Phe Gly Leu Phe Cys
    3785                3790                3795

Leu Leu Asn Arg Tyr Phe Arg Leu Thr Leu Gly Val Tyr Asp Tyr
    3800                3805                3810

Leu Val Ser Thr Gln Glu Phe Arg Tyr Met Asn Ser Gln Gly Leu
    3815                3820                3825

Leu Pro Pro Lys Asn Ser Ile Asp Ala Phe Lys Leu Asn Ile Lys
    3830                3835                3840

Leu Leu Gly Val Gly Gly Lys Pro Cys Ile Lys Val Ala Thr Val
    3845                3850                3855

Gln Ser Lys Met Ser Asp Val Lys Cys Thr Ser Val Val Leu Leu
    3860                3865                3870

Ser Val Leu Gln Gln Leu Arg Val Glu Ser Ser Ser Lys Leu Trp
    3875                3880                3885

Ala Gln Cys Val Gln Leu His Asn Asp Ile Leu Leu Ala Lys Asp
    3890                3895                3900

Thr Thr Glu Ala Phe Glu Lys Met Val Ser Leu Leu Ser Val Leu
    3905                3910                3915

Leu Ser Met Gln Gly Ala Val Asp Ile Asn Lys Leu Cys Glu Glu
    3920                3925                3930

Met Leu Asp Asn Arg Ala Thr Leu Gln Ala Ile Ala Ser Glu Phe
    3935                3940                3945

Ser Ser Leu Pro Ser Tyr Ala Ala Phe Ala Thr Ala Gln Glu Ala
    3950                3955                3960

Tyr Glu Gln Ala Val Ala Asn Gly Asp Ser Glu Val Val Leu Lys
    3965                3970                3975

Lys Leu Lys Lys Ser Leu Asn Val Ala Lys Ser Glu Phe Asp Arg
    3980                3985                3990

Asp Ala Ala Met Gln Arg Lys Leu Glu Lys Met Ala Asp Gln Ala
    3995                4000                4005

Met Thr Gln Met Tyr Lys Gln Ala Arg Ser Glu Asp Lys Arg Ala
    4010                4015                4020

Lys Val Thr Ser Ala Met Gln Thr Met Leu Phe Thr Met Leu Arg
    4025                4030                4035

Lys Leu Asp Asn Asp Ala Leu Asn Asn Ile Ile Asn Asn Ala Arg
    4040                4045                4050

Asp Gly Cys Val Pro Leu Asn Ile Ile Pro Leu Thr Thr Ala Ala
    4055                4060                4065
```

```
Lys Leu Met Val Val Ile Pro Asp Tyr Asn Thr Tyr Lys Asn Thr
    4070                4075                4080

Cys Asp Gly Thr Thr Phe Thr Tyr Ala Ser Ala Leu Trp Glu Ile
    4085                4090                4095

Gln Gln Val Val Asp Ala Asp Ser Lys Ile Val Gln Leu Ser Glu
    4100                4105                4110

Ile Ser Met Asp Asn Ser Pro Asn Leu Ala Trp Pro Leu Ile Val
    4115                4120                4125

Thr Ala Leu Arg Ala Asn Ser Ala Val Lys Leu Gln Asn Asn Glu
    4130                4135                4140

Leu Ser Pro Val Ala Leu Arg Gln Met Ser Cys Ala Ala Gly Thr
    4145                4150                4155

Thr Gln Thr Ala Cys Thr Asp Asp Asn Ala Leu Ala Tyr Tyr Asn
    4160                4165                4170

Thr Thr Lys Gly Gly Arg Phe Val Leu Ala Leu Leu Ser Asp Leu
    4175                4180                4185

Gln Asp Leu Lys Trp Ala Arg Phe Pro Lys Ser Asp Gly Thr Gly
    4190                4195                4200

Thr Ile Tyr Thr Glu Leu Glu Pro Pro Cys Arg Phe Val Thr Asp
    4205                4210                4215

Thr Pro Lys Gly Pro Lys Val Lys Tyr Leu Tyr Phe Ile Lys Gly
    4220                4225                4230

Leu Asn Asn Leu Asn Arg Gly Met Val Leu Gly Ser Leu Ala Ala
    4235                4240                4245

Thr Val Arg Leu Gln Ala Gly Asn Ala Thr Glu Val Pro Ala Asn
    4250                4255                4260

Ser Thr Val Leu Ser Phe Cys Ala Phe Ala Val Asp Ala Ala Lys
    4265                4270                4275

Ala Tyr Lys Asp Tyr Leu Ala Ser Gly Gly Gln Pro Ile Thr Asn
    4280                4285                4290

Cys Val Lys Met Leu Cys Thr His Thr Gly Thr Gly Gln Ala Ile
    4295                4300                4305

Thr Val Thr Pro Glu Ala Asn Met Asp Gln Glu Ser Phe Gly Gly
    4310                4315                4320

Ala Ser Cys Cys Leu Tyr Cys Arg Cys His Ile Asp His Pro Asn
    4325                4330                4335

Pro Lys Gly Phe Cys Asp Leu Lys Gly Lys Tyr Val Gln Ile Pro
    4340                4345                4350

Thr Thr Cys Ala Asn Asp Pro Val Gly Phe Thr Leu Lys Asn Thr
    4355                4360                4365

Val Cys Thr Val Cys Gly Met Trp Lys Gly Tyr Gly Cys Ser Cys
    4370                4375                4380

Asp Gln Leu Arg Glu Pro Met Leu Gln Ser Ala Asp Ala Gln Ser
    4385                4390                4395

Phe Leu Asn Arg Val Cys Gly Val Ser Ala Ala Arg Leu Thr Pro
    4400                4405                4410

Cys Gly Thr Gly Thr Ser Thr Asp Val Val Tyr Arg Ala Phe Asp
    4415                4420                4425

Ile Tyr Asn Asp Lys Val Ala Gly Phe Ala Lys Phe Leu Lys Thr
    4430                4435                4440

Asn Cys Cys Arg Phe Gln Glu Lys Asp Glu Asp Asp Asn Leu Ile
    4445                4450                4455
```

Asp Ser Tyr Phe Val Val Lys Arg His Thr Phe Ser Asn Tyr Gln
4460 4465 4470

His Glu Glu Thr Ile Tyr Asn Leu Leu Lys Asp Cys Pro Ala Val
4475 4480 4485

Ala Lys His Asp Phe Phe Lys Phe Arg Ile Asp Gly Asp Met Val
4490 4495 4500

Pro His Ile Ser Arg Gln Arg Leu Thr Lys Tyr Thr Met Ala Asp
4505 4510 4515

Leu Val Tyr Ala Leu Arg His Phe Asp Glu Gly Asn Cys Asp Thr
4520 4525 4530

Leu Lys Glu Ile Leu Val Thr Tyr Asn Cys Cys Asp Asp Asp Tyr
4535 4540 4545

Phe Asn Lys Lys Asp Trp Tyr Asp Phe Val Glu Asn Pro Asp Ile
4550 4555 4560

Leu Arg Val Tyr Ala Asn Leu Gly Glu Arg Val Arg Gln Ala Leu
4565 4570 4575

Leu Lys Thr Val Gln Phe Cys Asp Ala Met Arg Asn Ala Gly Ile
4580 4585 4590

Val Gly Val Leu Thr Leu Asp Asn Gln Asp Leu Asn Gly Asn Trp
4595 4600 4605

Tyr Asp Phe Gly Asp Phe Ile Gln Thr Thr Pro Gly Ser Gly Val
4610 4615 4620

Pro Val Val Asp Ser Tyr Tyr Ser Leu Leu Met Pro Ile Leu Thr
4625 4630 4635

Leu Thr Arg Ala Leu Thr Ala Glu Ser His Val Asp Thr Asp Leu
4640 4645 4650

Thr Lys Pro Tyr Ile Lys Trp Asp Leu Leu Lys Tyr Asp Phe Thr
4655 4660 4665

Glu Glu Arg Leu Lys Leu Phe Asp Arg Tyr Phe Lys Tyr Trp Asp
4670 4675 4680

Gln Thr Tyr His Pro Asn Cys Val Asn Cys Leu Asp Asp Arg Cys
4685 4690 4695

Ile Leu His Cys Ala Asn Phe Asn Val Leu Phe Ser Thr Val Phe
4700 4705 4710

Pro Pro Thr Ser Phe Gly Pro Leu Val Arg Lys Ile Phe Val Asp
4715 4720 4725

Gly Val Pro Phe Val Val Ser Thr Gly Tyr His Phe Arg Glu Leu
4730 4735 4740

Gly Val Val His Asn Gln Asp Val Asn Leu His Ser Ser Arg Leu
4745 4750 4755

Ser Phe Lys Glu Leu Leu Val Tyr Ala Ala Asp Pro Ala Met His
4760 4765 4770

Ala Ala Ser Gly Asn Leu Leu Leu Asp Lys Arg Thr Thr Cys Phe
4775 4780 4785

Ser Val Ala Ala Leu Thr Asn Asn Val Ala Phe Gln Thr Val Lys
4790 4795 4800

Pro Gly Asn Phe Asn Lys Asp Phe Tyr Asp Phe Ala Val Ser Lys
4805 4810 4815

Gly Phe Phe Lys Glu Gly Ser Ser Val Glu Leu Lys His Phe Phe
4820 4825 4830

Phe Ala Gln Asp Gly Asn Ala Ala Ile Ser Asp Tyr Asp Tyr Tyr
4835 4840 4845

Arg Tyr Asn Leu Pro Thr Met Cys Asp Ile Arg Gln Leu Leu Phe

-continued

```
    4850                4855                4860

Val Val  Glu Val Val Asp Lys  Tyr Phe Asp Cys Tyr  Asp Gly Gly
    4865                4870                4875

Cys Ile  Asn Ala Asn Gln Val  Ile Val Asn Asn Leu  Asp Lys Ser
    4880                4885                4890

Ala Gly  Phe Pro Phe Asn Lys  Trp Gly Lys Ala Arg  Leu Tyr Tyr
    4895                4900                4905

Asp Ser  Met Ser Tyr Glu Asp  Gln Asp Ala Leu Phe  Ala Tyr Thr
    4910                4915                4920

Lys Arg  Asn Val Ile Pro Thr  Ile Thr Gln Met Asn  Leu Lys Tyr
    4925                4930                4935

Ala Ile  Ser Ala Lys Asn Arg  Ala Arg Thr Val Ala  Gly Val Ser
    4940                4945                4950

Ile Cys  Ser Thr Met Thr Asn  Arg Gln Phe His Gln  Lys Leu Leu
    4955                4960                4965

Lys Ser  Ile Ala Ala Thr Arg  Gly Ala Thr Val Val  Ile Gly Thr
    4970                4975                4980

Ser Lys  Phe Tyr Gly Gly Trp  His Asn Met Leu Lys  Thr Val Tyr
    4985                4990                4995

Ser Asp  Val Glu Asn Pro His  Leu Met Gly Trp Asp  Tyr Pro Lys
    5000                5005                5010

Cys Asp  Arg Ala Met Pro Asn  Met Leu Arg Ile Met  Ala Ser Leu
    5015                5020                5025

Val Leu  Ala Arg Lys His Thr  Thr Cys Cys Ser Leu  Ser His Arg
    5030                5035                5040

Phe Tyr  Arg Leu Ala Asn Glu  Cys Ala Gln Val Leu  Ser Glu Met
    5045                5050                5055

Val Met  Cys Gly Gly Ser Leu  Tyr Val Lys Pro Gly  Gly Thr Ser
    5060                5065                5070

Ser Gly  Asp Ala Thr Thr Ala  Tyr Ala Asn Ser Val  Phe Asn Ile
    5075                5080                5085

Cys Gln  Ala Val Thr Ala Asn  Val Asn Ala Leu Leu  Ser Thr Asp
    5090                5095                5100

Gly Asn  Lys Ile Ala Asp Lys  Tyr Val Arg Asn Leu  Gln His Arg
    5105                5110                5115

Leu Tyr  Glu Cys Leu Tyr Arg  Asn Arg Asp Val Asp  Thr Asp Phe
    5120                5125                5130

Val Asn  Glu Phe Tyr Ala Tyr  Leu Arg Lys His Phe  Ser Met Met
    5135                5140                5145

Ile Leu  Ser Asp Asp Ala Val  Val Cys Phe Asn Ser  Thr Tyr Ala
    5150                5155                5160

Ser Gln  Gly Leu Val Ala Ser  Ile Lys Asn Phe Lys  Ser Val Leu
    5165                5170                5175

Tyr Tyr  Gln Asn Asn Val Phe  Met Ser Glu Ala Lys  Cys Trp Thr
    5180                5185                5190

Glu Thr  Asp Leu Thr Lys Gly  Pro His Glu Phe Cys  Ser Gln His
    5195                5200                5205

Thr Met  Leu Val Lys Gln Gly  Asp Asp Tyr Val Tyr  Leu Pro Tyr
    5210                5215                5220

Pro Asp  Pro Ser Arg Ile Leu  Gly Ala Gly Cys Phe  Val Asp Asp
    5225                5230                5235

Ile Val  Lys Thr Asp Gly Thr  Leu Met Ile Glu Arg  Phe Val Ser
    5240                5245                5250
```

```
Leu Ala Ile Asp Ala Tyr Pro Leu Thr Lys His Pro Asn Gln Glu
    5255                5260                5265

Tyr Ala Asp Val Phe His Leu Tyr Leu Gln Tyr Ile Arg Lys Leu
    5270                5275                5280

His Asp Glu Leu Thr Gly His Met Leu Asp Met Tyr Ser Val Met
    5285                5290                5295

Leu Thr Asn Asp Asn Thr Ser Arg Tyr Trp Glu Pro Glu Phe Tyr
    5300                5305                5310

Glu Ala Met Tyr Thr Pro His Thr Val Leu Gln Ala Val Gly Ala
    5315                5320                5325

Cys Val Leu Cys Asn Ser Gln Thr Ser Leu Arg Cys Gly Ala Cys
    5330                5335                5340

Ile Arg Arg Pro Phe Leu Cys Cys Lys Cys Cys Tyr Asp His Val
    5345                5350                5355

Ile Ser Thr Ser His Lys Leu Val Leu Ser Val Asn Pro Tyr Val
    5360                5365                5370

Cys Asn Ala Pro Gly Cys Asp Val Thr Asp Val Thr Gln Leu Tyr
    5375                5380                5385

Leu Gly Gly Met Ser Tyr Tyr Cys Lys Ser His Lys Pro Pro Ile
    5390                5395                5400

Ser Phe Pro Leu Cys Ala Asn Gly Gln Val Phe Gly Leu Tyr Lys
    5405                5410                5415

Asn Thr Cys Val Gly Ser Asp Asn Val Thr Asp Phe Asn Ala Ile
    5420                5425                5430

Ala Thr Cys Asp Trp Thr Asn Ala Gly Asp Tyr Ile Leu Ala Asn
    5435                5440                5445

Thr Cys Thr Glu Arg Leu Lys Leu Phe Ala Ala Glu Thr Leu Lys
    5450                5455                5460

Ala Thr Glu Glu Thr Phe Lys Leu Ser Tyr Gly Ile Ala Thr Val
    5465                5470                5475

Arg Glu Val Leu Ser Asp Arg Glu Leu His Leu Ser Trp Glu Val
    5480                5485                5490

Gly Lys Pro Arg Pro Pro Leu Asn Arg Asn Tyr Val Phe Thr Gly
    5495                5500                5505

Tyr Arg Val Thr Lys Asn Ser Lys Val Gln Ile Gly Glu Tyr Thr
    5510                5515                5520

Phe Glu Lys Gly Asp Tyr Gly Asp Ala Val Val Tyr Arg Gly Thr
    5525                5530                5535

Thr Thr Tyr Lys Leu Asn Val Gly Asp Tyr Phe Val Leu Thr Ser
    5540                5545                5550

His Thr Val Met Pro Leu Ser Ala Pro Thr Leu Val Pro Gln Glu
    5555                5560                5565

His Tyr Val Arg Ile Thr Gly Leu Tyr Pro Thr Leu Asn Ile Ser
    5570                5575                5580

Asp Glu Phe Ser Ser Asn Val Ala Asn Tyr Gln Lys Val Gly Met
    5585                5590                5595

Gln Lys Tyr Ser Thr Leu Gln Gly Pro Pro Gly Thr Gly Lys Ser
    5600                5605                5610

His Phe Ala Ile Gly Leu Ala Leu Tyr Tyr Pro Ser Ala Arg Ile
    5615                5620                5625

Val Tyr Thr Ala Cys Ser His Ala Ala Val Asp Ala Leu Cys Glu
    5630                5635                5640
```

```
Lys Ala Leu Lys Tyr Leu Pro Ile Asp Lys Cys Ser Arg Ile Ile
    5645                5650                5655

Pro Ala Arg Ala Arg Val Glu Cys Phe Asp Lys Phe Lys Val Asn
    5660                5665                5670

Ser Thr Leu Glu Gln Tyr Val Phe Cys Thr Val Asn Ala Leu Pro
    5675                5680                5685

Glu Thr Thr Ala Asp Ile Val Val Phe Asp Glu Ile Ser Met Ala
    5690                5695                5700

Thr Asn Tyr Asp Leu Ser Val Val Asn Ala Arg Leu Arg Ala Lys
    5705                5710                5715

His Tyr Val Tyr Ile Gly Asp Pro Ala Gln Leu Pro Ala Pro Arg
    5720                5725                5730

Thr Leu Leu Thr Lys Gly Thr Leu Glu Pro Glu Tyr Phe Asn Ser
    5735                5740                5745

Val Cys Arg Leu Met Lys Thr Ile Gly Pro Asp Met Phe Leu Gly
    5750                5755                5760

Thr Cys Arg Arg Cys Pro Ala Glu Ile Val Asp Thr Val Ser Ala
    5765                5770                5775

Leu Val Tyr Asp Asn Lys Leu Lys Ala His Lys Asp Lys Ser Ala
    5780                5785                5790

Gln Cys Phe Lys Met Phe Tyr Lys Gly Val Ile Thr His Asp Val
    5795                5800                5805

Ser Ser Ala Ile Asn Arg Pro Gln Ile Gly Val Val Arg Glu Phe
    5810                5815                5820

Leu Thr Arg Asn Pro Ala Trp Arg Lys Ala Val Phe Ile Ser Pro
    5825                5830                5835

Tyr Asn Ser Gln Asn Ala Val Ala Ser Lys Ile Leu Gly Leu Pro
    5840                5845                5850

Thr Gln Thr Val Asp Ser Ser Gln Gly Ser Glu Tyr Asp Tyr Val
    5855                5860                5865

Ile Phe Thr Gln Thr Thr Glu Thr Ala His Ser Cys Asn Val Asn
    5870                5875                5880

Arg Phe Asn Val Ala Ile Thr Arg Ala Lys Val Gly Ile Leu Cys
    5885                5890                5895

Ile Met Ser Asp Arg Asp Leu Tyr Asp Lys Leu Gln Phe Thr Ser
    5900                5905                5910

Leu Glu Ile Pro Arg Arg Asn Val Ala Thr Leu Gln Ala Glu Asn
    5915                5920                5925

Val Thr Gly Leu Phe Lys Asp Cys Ser Lys Val Ile Thr Gly Leu
    5930                5935                5940

His Pro Thr Gln Ala Pro Thr His Leu Ser Val Asp Thr Lys Phe
    5945                5950                5955

Lys Thr Glu Gly Leu Cys Val Asp Ile Pro Gly Ile Pro Lys Asp
    5960                5965                5970

Met Thr Tyr Arg Arg Leu Ile Ser Met Met Gly Phe Lys Met Asn
    5975                5980                5985

Tyr Gln Val Asn Gly Tyr Pro Asn Met Phe Ile Thr Arg Glu Glu
    5990                5995                6000

Ala Ile Arg His Val Arg Ala Trp Ile Gly Phe Asp Val Glu Gly
    6005                6010                6015

Cys His Ala Thr Arg Glu Ala Val Gly Thr Asn Leu Pro Leu Gln
    6020                6025                6030

Leu Gly Phe Ser Thr Gly Val Asn Leu Val Ala Val Pro Thr Gly
```

6035 6040 6045

Tyr Val Asp Thr Pro Asn Asn Thr Asp Phe Ser Arg Val Ser Ala
6050 6055 6060

Lys Pro Pro Pro Gly Asp Gln Phe Lys His Leu Ile Pro Leu Met
6065 6070 6075

Tyr Lys Gly Leu Pro Trp Asn Val Val Arg Ile Lys Ile Val Gln
6080 6085 6090

Met Leu Ser Asp Thr Leu Lys Asn Leu Ser Asp Arg Val Val Phe
6095 6100 6105

Val Leu Trp Ala His Gly Phe Glu Leu Thr Ser Met Lys Tyr Phe
6110 6115 6120

Val Lys Ile Gly Pro Glu Arg Thr Cys Cys Leu Cys Asp Arg Arg
6125 6130 6135

Ala Thr Cys Phe Ser Thr Ala Ser Asp Thr Tyr Ala Cys Trp His
6140 6145 6150

His Ser Ile Gly Phe Asp Tyr Val Tyr Asn Pro Phe Met Ile Asp
6155 6160 6165

Val Gln Gln Trp Gly Phe Thr Gly Asn Leu Gln Ser Asn His Asp
6170 6175 6180

Leu Tyr Cys Gln Val His Gly Asn Ala His Val Ala Ser Cys Asp
6185 6190 6195

Ala Ile Met Thr Arg Cys Leu Ala Val His Glu Cys Phe Val Lys
6200 6205 6210

Arg Val Asp Trp Thr Ile Glu Tyr Pro Ile Ile Gly Asp Glu Leu
6215 6220 6225

Lys Ile Asn Ala Ala Cys Arg Lys Val Gln His Met Val Val Lys
6230 6235 6240

Ala Ala Leu Leu Ala Asp Lys Phe Pro Val Leu His Asp Ile Gly
6245 6250 6255

Asn Pro Lys Ala Ile Lys Cys Val Pro Gln Ala Asp Val Glu Trp
6260 6265 6270

Lys Phe Tyr Asp Ala Gln Pro Cys Ser Asp Lys Ala Tyr Lys Ile
6275 6280 6285

Glu Glu Leu Phe Tyr Ser Tyr Ala Thr His Ser Asp Lys Phe Thr
6290 6295 6300

Asp Gly Val Cys Leu Phe Trp Asn Cys Asn Val Asp Arg Tyr Pro
6305 6310 6315

Ala Asn Ser Ile Val Cys Arg Phe Asp Thr Arg Val Leu Ser Asn
6320 6325 6330

Leu Asn Leu Pro Gly Cys Asp Gly Gly Ser Leu Tyr Val Asn Lys
6335 6340 6345

His Ala Phe His Thr Pro Ala Phe Asp Lys Ser Ala Phe Val Asn
6350 6355 6360

Leu Lys Gln Leu Pro Phe Phe Tyr Tyr Ser Asp Ser Pro Cys Glu
6365 6370 6375

Ser His Gly Lys Gln Val Val Ser Asp Ile Asp Tyr Val Pro Leu
6380 6385 6390

Lys Ser Ala Thr Cys Ile Thr Arg Cys Asn Leu Gly Gly Ala Val
6395 6400 6405

Cys Arg His His Ala Asn Glu Tyr Arg Leu Tyr Leu Asp Ala Tyr
6410 6415 6420

Asn Met Met Ile Ser Ala Gly Phe Ser Leu Trp Val Tyr Lys Gln
6425 6430 6435

```
Phe Asp Thr Tyr Asn Leu Trp Asn Thr Phe Thr Arg Leu Gln Ser
    6440                6445                6450

Leu Glu Asn Val Ala Phe Asn Val Val Asn Lys Gly His Phe Asp
    6455                6460                6465

Gly Gln Gln Gly Glu Val Pro Val Ser Ile Ile Asn Asn Thr Val
    6470                6475                6480

Tyr Thr Lys Val Asp Gly Val Asp Val Glu Leu Phe Glu Asn Lys
    6485                6490                6495

Thr Thr Leu Pro Val Asn Val Ala Phe Glu Leu Trp Ala Lys Arg
    6500                6505                6510

Asn Ile Lys Pro Val Pro Glu Val Lys Ile Leu Asn Asn Leu Gly
    6515                6520                6525

Val Asp Ile Ala Ala Asn Thr Val Ile Trp Asp Tyr Lys Arg Asp
    6530                6535                6540

Ala Pro Ala His Ile Ser Thr Ile Gly Val Cys Ser Met Thr Asp
    6545                6550                6555

Ile Ala Lys Lys Pro Thr Glu Thr Ile Cys Ala Pro Leu Thr Val
    6560                6565                6570

Phe Phe Asp Gly Arg Val Asp Gly Gln Val Asp Leu Phe Arg Asn
    6575                6580                6585

Ala Arg Asn Gly Val Leu Ile Thr Glu Gly Ser Val Lys Gly Leu
    6590                6595                6600

Gln Pro Ser Val Gly Pro Lys Gln Ala Ser Leu Asn Gly Val Thr
    6605                6610                6615

Leu Ile Gly Glu Ala Val Lys Thr Gln Phe Asn Tyr Tyr Lys Lys
    6620                6625                6630

Val Asp Gly Val Val Gln Gln Leu Pro Glu Thr Tyr Phe Thr Gln
    6635                6640                6645

Ser Arg Asn Leu Gln Glu Phe Lys Pro Arg Ser Gln Met Glu Ile
    6650                6655                6660

Asp Phe Leu Glu Leu Ala Met Asp Glu Phe Ile Glu Arg Tyr Lys
    6665                6670                6675

Leu Glu Gly Tyr Ala Phe Glu His Ile Val Tyr Gly Asp Phe Ser
    6680                6685                6690

His Ser Gln Leu Gly Gly Leu His Leu Leu Ile Gly Leu Ala Lys
    6695                6700                6705

Arg Phe Lys Glu Ser Pro Phe Glu Leu Glu Asp Phe Ile Pro Met
    6710                6715                6720

Asp Ser Thr Val Lys Asn Tyr Phe Ile Thr Asp Ala Gln Thr Gly
    6725                6730                6735

Ser Ser Lys Cys Val Cys Ser Val Ile Asp Leu Leu Leu Asp Asp
    6740                6745                6750

Phe Val Glu Ile Ile Lys Ser Gln Asp Leu Ser Val Val Ser Lys
    6755                6760                6765

Val Val Lys Val Thr Ile Asp Tyr Thr Glu Ile Ser Phe Met Leu
    6770                6775                6780

Trp Cys Lys Asp Gly His Val Glu Thr Phe Tyr Pro Lys Leu Gln
    6785                6790                6795

Ser Ser Gln Ala Trp Gln Pro Gly Val Ala Met Pro Asn Leu Tyr
    6800                6805                6810

Lys Met Gln Arg Met Leu Leu Glu Lys Cys Asp Leu Gln Asn Tyr
    6815                6820                6825
```

```
Gly Asp  Ser Ala Thr Leu Pro  Lys Gly Ile Met Met  Asn Val Ala
    6830                6835                 6840

Lys Tyr  Thr Gln Leu Cys Gln  Tyr Leu Asn Thr Leu  Thr Leu Ala
    6845                6850                 6855

Val Pro  Tyr Asn Met Arg Val  Ile His Phe Gly Ala  Gly Ser Asp
    6860                6865                 6870

Lys Gly  Val Ala Pro Gly Thr  Ala Val Leu Arg Gln  Trp Leu Pro
    6875                6880                 6885

Thr Gly  Thr Leu Leu Val Asp  Ser Asp Leu Asn Asp  Phe Val Ser
    6890                6895                 6900

Asp Ala  Asp Ser Thr Leu Ile  Gly Asp Cys Ala Thr  Val His Thr
    6905                6910                 6915

Ala Asn  Lys Trp Asp Leu Ile  Ile Ser Asp Met Tyr  Asp Pro Lys
    6920                6925                 6930

Thr Lys  Asn Val Thr Lys Glu  Asn Asp Ser Lys Glu  Gly Phe Phe
    6935                6940                 6945

Thr Tyr  Ile Cys Gly Phe Ile  Gln Gln Lys Leu Ala  Leu Gly Gly
    6950                6955                 6960

Ser Val  Ala Ile Lys Ile Thr  Glu His Ser Trp Asn  Ala Asp Leu
    6965                6970                 6975

Tyr Lys  Leu Met Gly His Phe  Ala Trp Trp Thr Ala  Phe Val Thr
    6980                6985                 6990

Asn Val  Asn Ala Ser Ser Ser  Glu Ala Phe Leu Ile  Gly Cys Asn
    6995                7000                 7005

Tyr Leu  Gly Lys Pro Arg Glu  Gln Ile Asp Gly Tyr  Val Met His
    7010                7015                 7020

Ala Asn  Tyr Ile Phe Trp Arg  Asn Thr Asn Pro Ile  Gln Leu Ser
    7025                7030                 7035

Ser Tyr  Ser Leu Phe Asp Met  Ser Lys Phe Pro Leu  Lys Leu Arg
    7040                7045                 7050

Gly Thr  Ala Val Met Ser Leu  Lys Glu Gly Gln Ile  Asn Asp Met
    7055                7060                 7065

Ile Leu  Ser Leu Leu Ser Lys  Gly Arg Leu Ile Ile  Arg Glu Asn
    7070                7075                 7080

Asn Arg  Val Val Ile Ser Ser  Asp Val Leu Val Asn  Asn
    7085                7090                 7095


<210> SEQ ID NO 22
<211> LENGTH: 275
<212> TYPE: PRT
<213> ORGANISM: Severe acute respiratory syndrome coronavirus 2

<400> SEQUENCE: 22

Met Asp Leu Phe Met Arg Ile Phe Thr Ile Gly Thr Val Thr Leu Lys
1               5                   10                  15

Gln Gly Glu Ile Lys Asp Ala Thr Pro Ser Asp Phe Val Arg Ala Thr
            20                  25                  30

Ala Thr Ile Pro Ile Gln Ala Ser Leu Pro Phe Gly Trp Leu Ile Val
        35                  40                  45

Gly Val Ala Leu Leu Ala Val Phe Gln Ser Ala Ser Lys Ile Ile Thr
    50                  55                  60

Leu Lys Lys Arg Trp Gln Leu Ala Leu Ser Lys Gly Val His Phe Val
65                  70                  75                  80

Cys Asn Leu Leu Leu Leu Phe Val Thr Val Tyr Ser His Leu Leu Leu
                85                  90                  95
```

```
Val Ala Ala Gly Leu Glu Ala Pro Phe Leu Tyr Leu Tyr Ala Leu Val
            100                 105                 110

Tyr Phe Leu Gln Ser Ile Asn Phe Val Arg Ile Ile Met Arg Leu Trp
        115                 120                 125

Leu Cys Trp Lys Cys Arg Ser Lys Asn Pro Leu Leu Tyr Asp Ala Asn
    130                 135                 140

Tyr Phe Leu Cys Trp His Thr Asn Cys Tyr Asp Tyr Cys Ile Pro Tyr
145                 150                 155                 160

Asn Ser Val Thr Ser Ser Ile Val Ile Thr Ser Gly Asp Gly Thr Thr
                165                 170                 175

Ser Pro Ile Ser Glu His Asp Tyr Gln Ile Gly Gly Tyr Thr Glu Lys
            180                 185                 190

Trp Glu Ser Gly Val Lys Asp Cys Val Val Leu His Ser Tyr Phe Thr
        195                 200                 205

Ser Asp Tyr Tyr Gln Leu Tyr Ser Thr Gln Leu Ser Thr Asp Thr Gly
    210                 215                 220

Val Glu His Val Thr Phe Phe Ile Tyr Asn Lys Ile Val Asp Glu Pro
225                 230                 235                 240

Glu Glu His Val Gln Ile His Thr Ile Asp Gly Ser Ser Gly Val Val
                245                 250                 255

Asn Pro Val Met Glu Pro Ile Tyr Asp Glu Pro Thr Thr Thr Thr Ser
            260                 265                 270

Val Pro Leu
        275


<210> SEQ ID NO 23
<211> LENGTH: 61
<212> TYPE: PRT
<213> ORGANISM: Severe acute respiratory syndrome coronavirus 2

<400> SEQUENCE: 23

Met Phe His Leu Val Asp Phe Gln Val Thr Ile Ala Glu Ile Leu Leu
1               5                   10                  15

Ile Ile Met Arg Thr Phe Lys Val Ser Ile Trp Asn Leu Asp Tyr Ile
            20                  25                  30

Ile Asn Leu Ile Ile Lys Asn Leu Ser Lys Ser Leu Thr Glu Asn Lys
        35                  40                  45

Tyr Ser Gln Leu Asp Glu Glu Gln Pro Met Glu Ile Asp
    50                  55                  60


<210> SEQ ID NO 24
<211> LENGTH: 121
<212> TYPE: PRT
<213> ORGANISM: Severe acute respiratory syndrome coronavirus 2

<400> SEQUENCE: 24

Met Lys Ile Ile Leu Phe Leu Ala Leu Ile Thr Leu Ala Thr Cys Glu
1               5                   10                  15

Leu Tyr His Tyr Gln Glu Cys Val Arg Gly Thr Thr Val Leu Leu Lys
            20                  25                  30

Glu Pro Cys Ser Ser Gly Thr Tyr Glu Gly Asn Ser Pro Phe His Pro
        35                  40                  45

Leu Ala Asp Asn Lys Phe Ala Leu Thr Cys Phe Ser Thr Gln Phe Ala
    50                  55                  60

Phe Ala Cys Pro Asp Gly Val Lys His Val Tyr Gln Leu Arg Ala Arg
65                  70                  75                  80
```

Ser Val Ser Pro Lys Leu Phe Ile Arg Gln Glu Glu Val Gln Glu Leu
85 90 95

Tyr Ser Pro Ile Phe Leu Ile Val Ala Ala Ile Val Phe Ile Thr Leu
100 105 110

Cys Phe Thr Leu Lys Arg Lys Thr Glu
115 120

<210> SEQ ID NO 25
<211> LENGTH: 121
<212> TYPE: PRT
<213> ORGANISM: Severe acute respiratory syndrome coronavirus 2

<400> SEQUENCE: 25

Met Lys Phe Leu Val Phe Leu Gly Ile Ile Thr Thr Val Ala Ala Phe
1 5 10 15

His Gln Glu Cys Ser Leu Gln Ser Cys Thr Gln His Gln Pro Tyr Val
20 25 30

Val Asp Asp Pro Cys Pro Ile His Phe Tyr Ser Lys Trp Tyr Ile Arg
35 40 45

Val Gly Ala Arg Lys Ser Ala Pro Leu Ile Glu Leu Cys Val Asp Glu
50 55 60

Ala Gly Ser Lys Ser Pro Ile Gln Tyr Ile Asp Ile Gly Asn Tyr Thr
65 70 75 80

Val Ser Cys Leu Pro Phe Thr Ile Asn Cys Gln Glu Pro Lys Leu Gly
85 90 95

Ser Leu Val Val Arg Cys Ser Phe Tyr Glu Asp Phe Leu Glu Tyr His
100 105 110

Asp Val Arg Val Val Leu Asp Phe Ile
115 120

<210> SEQ ID NO 26
<211> LENGTH: 38
<212> TYPE: PRT
<213> ORGANISM: Severe acute respiratory syndrome coronavirus 2

<400> SEQUENCE: 26

Met Gly Tyr Ile Asn Val Phe Ala Phe Pro Phe Thr Ile Tyr Ser Leu
1 5 10 15

Leu Leu Cys Arg Met Asn Ser Arg Asn Tyr Ile Ala Gln Val Asp Val
20 25 30

Val Asn Phe Asn Leu Thr
35

<210> SEQ ID NO 27
<211> LENGTH: 4
<212> TYPE: PRT
<213> ORGANISM: Artificial Sequence
<220> FEATURE:
<223> OTHER INFORMATION: a linker peptide

<400> SEQUENCE: 27

Asn Lys Arg Lys
1

<210> SEQ ID NO 28
<211> LENGTH: 22
<212> TYPE: DNA
<213> ORGANISM: Artificial Sequence
<220> FEATURE:
<223> OTHER INFORMATION: a PCR primer for the TCR analysis

<400> SEQUENCE: 28
gtctaccagg cattcgcttc at 22

<210> SEQ ID NO 29
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 29
tcagctggac cacagccgca gcgt 24

<210> SEQ ID NO 30
<211> LENGTH: 21
<212> TYPE: DNA
<213> ORGANISM: Artificial Sequence
<220> FEATURE:
<223> OTHER INFORMATION: a PCR primer for the TCR analysis

<400> SEQUENCE: 30
tcagaaatcc tttctcttga c 21

<210> SEQ ID NO 31
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 31
ctagcctctg gaatcctttc tctt 24

<210> SEQ ID NO 32
<211> LENGTH: 16
<212> TYPE: PRT
<213> ORGANISM: Homo sapiens

<400> SEQUENCE: 32

Cys Ala Val Arg Gly Ser Gly Gly Gly Ala Thr Asn Lys Leu Ile Phe
1 5 10 15

<210> SEQ ID NO 33
<211> LENGTH: 14
<212> TYPE: PRT
<213> ORGANISM: Homo sapiens

<400> SEQUENCE: 33

Cys Ala Ser Ser Pro Ser Gly Pro Asn Tyr Glu Gln Tyr Phe
1 5 10

<210> SEQ ID NO 34
<211> LENGTH: 11
<212> TYPE: PRT
<213> ORGANISM: Homo sapiens

<400> SEQUENCE: 34

Cys Ala Val Phe Asn Asp Tyr Lys Leu Ser Phe
1 5 10

<210> SEQ ID NO 35
<211> LENGTH: 17
<212> TYPE: PRT
<213> ORGANISM: Homo sapiens

<400> SEQUENCE: 35

Cys Ala Ser Ser Ser Arg Thr Ser Gly Arg Ser Ser Tyr Glu Gln Tyr
1 5 10 15

Phe

<210> SEQ ID NO 36
<211> LENGTH: 12
<212> TYPE: PRT
<213> ORGANISM: Homo sapiens

<400> SEQUENCE: 36

Cys Val Val Ser Ala Leu Asn Ala Arg Leu Met Phe
1 5 10

<210> SEQ ID NO 37
<211> LENGTH: 15
<212> TYPE: PRT
<213> ORGANISM: Homo sapiens

<400> SEQUENCE: 37

Cys Ser Ala Arg Asp Tyr Thr Ser Ser Tyr Asn Glu Gln Phe Phe
1 5 10 15

<210> SEQ ID NO 38
<211> LENGTH: 14
<212> TYPE: PRT
<213> ORGANISM: Homo sapiens

<400> SEQUENCE: 38

Cys Ala Val His Phe Phe Pro Gly Tyr Ser Thr Leu Thr Phe
1 5 10

<210> SEQ ID NO 39
<211> LENGTH: 12
<212> TYPE: PRT
<213> ORGANISM: Homo sapiens

<400> SEQUENCE: 39

Cys Ala Gly Ala Gly Arg Gly Tyr Glu Gln Tyr Phe
1 5 10

<210> SEQ ID NO 40
<211> LENGTH: 13
<212> TYPE: PRT
<213> ORGANISM: Homo sapiens

<400> SEQUENCE: 40

Cys Ile Val Ser Asp Met Gly Arg Arg Ala Leu Thr Phe
1 5 10

<210> SEQ ID NO 41
<211> LENGTH: 17
<212> TYPE: PRT
<213> ORGANISM: Homo sapiens

<400> SEQUENCE: 41

Cys Ala Ser Ser Phe Thr Gly Thr Ser Gly Ser Leu Gly Glu Gln Phe
1 5 10 15

Phe

<210> SEQ ID NO 42
<211> LENGTH: 19

<212> TYPE: DNA
<213> ORGANISM: Artificial Sequence
<220> FEATURE:
<223> OTHER INFORMATION: a PCR primer for the TCR analysis

<400> SEQUENCE: 42
tgtaaaacga cggccagtg 19

<210> SEQ ID NO 43
<211> LENGTH: 16
<212> TYPE: DNA
<213> ORGANISM: Artificial Sequence
<220> FEATURE:
<223> OTHER INFORMATION: a PCR primer for the TCR analysis

<400> SEQUENCE: 43
ctggccgtcg ttttac 16

<210> SEQ ID NO 44
<211> LENGTH: 20
<212> TYPE: DNA
<213> ORGANISM: Artificial Sequence
<220> FEATURE:
<223> OTHER INFORMATION: a PCR primer for the TCR analysis

<400> SEQUENCE: 44
caggaaacag ctatgaccat 20

<210> SEQ ID NO 45
<211> LENGTH: 17
<212> TYPE: DNA
<213> ORGANISM: Artificial Sequence
<220> FEATURE:
<223> OTHER INFORMATION: a PCR primer for the TCR analysis

<400> SEQUENCE: 45
caggaaacag ctatgac 17

<210> SEQ ID NO 46
<211> LENGTH: 54
<212> TYPE: DNA
<213> ORGANISM: Artificial Sequence
<220> FEATURE:
<223> OTHER INFORMATION: a PCR primer for the TCR analysis

<400> SEQUENCE: 46
gtctcgtggg ctcggagatg tgtataagag acagtatcaa cgcagagtgg ccat 54

<210> SEQ ID NO 47
<211> LENGTH: 58
<212> TYPE: DNA
<213> ORGANISM: Artificial Sequence
<220> FEATURE:
<223> OTHER INFORMATION: a PCR primer for the TCR analysis

<400> SEQUENCE: 47
tcgtcggcag cgtcagatgt gtataagaga cagdvhdvtc tgatggctca aacacagc 58

<210> SEQ ID NO 48
<211> LENGTH: 58
<212> TYPE: DNA
<213> ORGANISM: Artificial Sequence
<220> FEATURE:
<223> OTHER INFORMATION: a PCR primer for the TCR analysis

<400> SEQUENCE: 48
tcgtcggcag cgtcagatgt gtataagaga cagdbdhhca gggtcagggt tctggata 58